(12) United States Patent
Wille et al.

(10) Patent No.: US 9,307,708 B2
(45) Date of Patent: *Apr. 12, 2016

(54) SYSTEMS FOR EXTRACTING MONOCOT EMBRYOS

(71) Applicants: PIONEER HI-BRED INTERNATIONAL, INC., Johnston, IA (US); E. I. du Pont de Nemours and Company, Wilmington, DE (US)

(72) Inventors: Jeffrey Dale Wille, Ankeny, IA (US); Donald H. Brunk, Boothwyn, PA (US); Mark William Deaver, Ridley Park, PA (US); Christopher Allen Janssen, Johnston, IA (US); Joshua Luke Mongan, St. Charles, IA (US); Patrick Ryan Mullins, Wilmington, DE (US); Larry Charles Mosher, Bondurant, IA (US); Jacob Patrick Suther, Waukee, IA (US)

(73) Assignees: PIONEER HI-BRED INTERNATIONAL INC, Johnston, IA (US); E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,518

(22) Filed: Mar. 6, 2015

(65) Prior Publication Data

US 2015/0252316 A1    Sep. 10, 2015

Related U.S. Application Data

(60) Provisional application No. 61/949,819, filed on Mar. 7, 2014.

(51) Int. Cl.
*C12N 15/82* (2006.01)
*A01H 4/00* (2006.01)

(52) U.S. Cl.
CPC ............... *A01H 4/003* (2013.01); *A01H 4/006* (2013.01)

(58) Field of Classification Search
CPC ........... A01H 4/00; A01H 5/00; A01H 4/006; B02B 3/12; C12M 45/02; C12M 45/06
See application file for complete search history.

(56) References Cited

U.S. PATENT DOCUMENTS

| | | | |
|---|---|---|---|
| 19,253 A | 2/1858 | Linder | 460/46 |
| 85,590 A | 1/1869 | Hawley | 460/45 |
| 247,718 A | 9/1881 | Warfield | 460/51 |
| 258,174 A | 5/1882 | Warfield | 460/51 |
| 276,054 A | 4/1883 | Longsdorf | 460/51 |
| 346,585 A | 8/1886 | Davidson | 460/51 |
| 464,764 A | 12/1891 | Ritty | 460/17 |
| 1,282,788 A | 10/1918 | Fenn | 460/17 |
| 1,651,591 A | 12/1927 | Foster | 460/54 |
| 1,744,954 A | 1/1930 | Douthhitt | 460/54 |
| 2,063,483 A | 12/1936 | Bulmer | 460/51 |
| 2,169,963 A | 8/1939 | Kerr | 460/17 |
| 2,424,241 A | 7/1947 | Kerr | 460/17 |
| 2,566,568 A | 9/1951 | Ives | 460/17 |
| 4,044,776 A | 8/1977 | Moore | 460/51 |
| 5,030,572 A | 7/1991 | Power et al. | 435/428 |
| 5,097,758 A | 3/1992 | Fresh | 99/590 |
| 5,284,765 A | 2/1994 | Bryan et al. | 435/420 |
| 5,589,617 A | 12/1996 | Nehra et al. | 800/278 |
| 6,463,845 B1 | 10/2002 | Thomas | 99/514 |
| 6,627,441 B1 | 9/2003 | Attree | 435/422 |
| 6,872,136 B1 | 3/2005 | Bennett | 460/51 |
| 7,150,993 B2 | 12/2006 | Davis et al. | 435/424 |
| 7,402,734 B2 | 7/2008 | Martinell et al. | 800/287 |
| 7,553,507 B2 | 6/2009 | Matthews | 426/481 |
| 7,560,611 B2 | 7/2009 | Adams et al. | 800/278 |
| 7,658,033 B2 | 2/2010 | Martinell et al. | 47/58.1 SE |
| 7,694,457 B2 | 4/2010 | Martinell et al. | 47/58.1 SE |
| 7,935,529 B2 | 5/2011 | Davis et al. | 435/424 |
| 7,937,890 B2 | 5/2011 | Adams et al. | 47/58.1 SE |
| 7,939,325 B2 | 5/2011 | Adams, Jr. et al. | 435/440 |
| 7,998,669 B2 | 8/2011 | Deppermann et al. | 435/6.1 |
| 8,245,439 B2 | 8/2012 | Deppermann et al. | 47/58.1 SE |
| 8,323,974 B2 | 12/2012 | Davis et al. | 435/424 |
| 8,434,259 B2 | 5/2013 | Deppermann | 47/58.1 SE |
| 2002/0042929 A1 | 4/2002 | Brar et al. | |
| 2005/0246786 A1 | 11/2005 | Adams et al. | |
| 2005/0246802 A1 | 11/2005 | Attree et al. | |
| 2007/0207485 A1* | 9/2007 | Deppermann et al. | 435/6 |
| 2008/0229447 A1 | 9/2008 | Hwang et al. | |
| 2011/0054969 A1 | 3/2011 | Barreiro et al. | |
| 2011/0078819 A1* | 3/2011 | Bullock | 800/278 |
| 2011/0212525 A1 | 9/2011 | Adams, Jr. et al. | |
| 2011/0271410 A1 | 11/2011 | Adams et al. | |

(Continued)

FOREIGN PATENT DOCUMENTS

| | | |
|---|---|---|
| CA | 2092588 | 9/1994 |
| CA | 2575863 | 3/2006 |

(Continued)

OTHER PUBLICATIONS

Smith, J., et al. (1985). Rapid isolation and purification of immature zygotic embryos. *Maize Genetics Cooperation Newsletter*, 59, 30-31.

(Continued)

*Primary Examiner* — Anne Kubelik
*Assistant Examiner* — Karen Redden
(74) *Attorney, Agent, or Firm* — Pioneer Hi-Bred Int'l, Inc.

(57) ABSTRACT

Methods and systems are provided which permit extraction of a monocot embryo (e.g., a corn embryo) of a monocot seed (e.g., a corn kernel) without damage to the monocot embryo. Methods disclosed herein provide embryos for uses in plant breeding and research procedures.

13 Claims, 46 Drawing Sheets

(56) References Cited

U.S. PATENT DOCUMENTS

2012/0124696 A1    5/2012   Ishida et al.
2012/0180166 A1    7/2012   Akula et al.
2013/0295674 A1   11/2013   Becker et al.

FOREIGN PATENT DOCUMENTS

| | | |
|---|---|---|
| CN | 102124956 | 7/2011 |
| CN | 102286526 | 12/2011 |
| CN | 102334448 | 2/2012 |
| DE | 69410247 | 9/1998 |
| EP | 674715 B2 | 10/1995 |
| EP | 2118289 * | 3/2008   ............... A01H 5/00 |
| WO | WO 94/13822 | 6/1994 |
| WO | WO 2006/022958 * | 3/2006   ............... A01H 4/00 |
| WO | WO 2006/022958 A1 * | 3/2006   ............... A02H 4/00 |
| WO | WO2008061095 | 5/2008 |
| WO | WO 2008112267 | 9/2008 |
| ZA | 200701638 | 11/2008 |

OTHER PUBLICATIONS

International Search Report for application No. PCT/US2015/019145 completed on May 8, 2015.

* cited by examiner

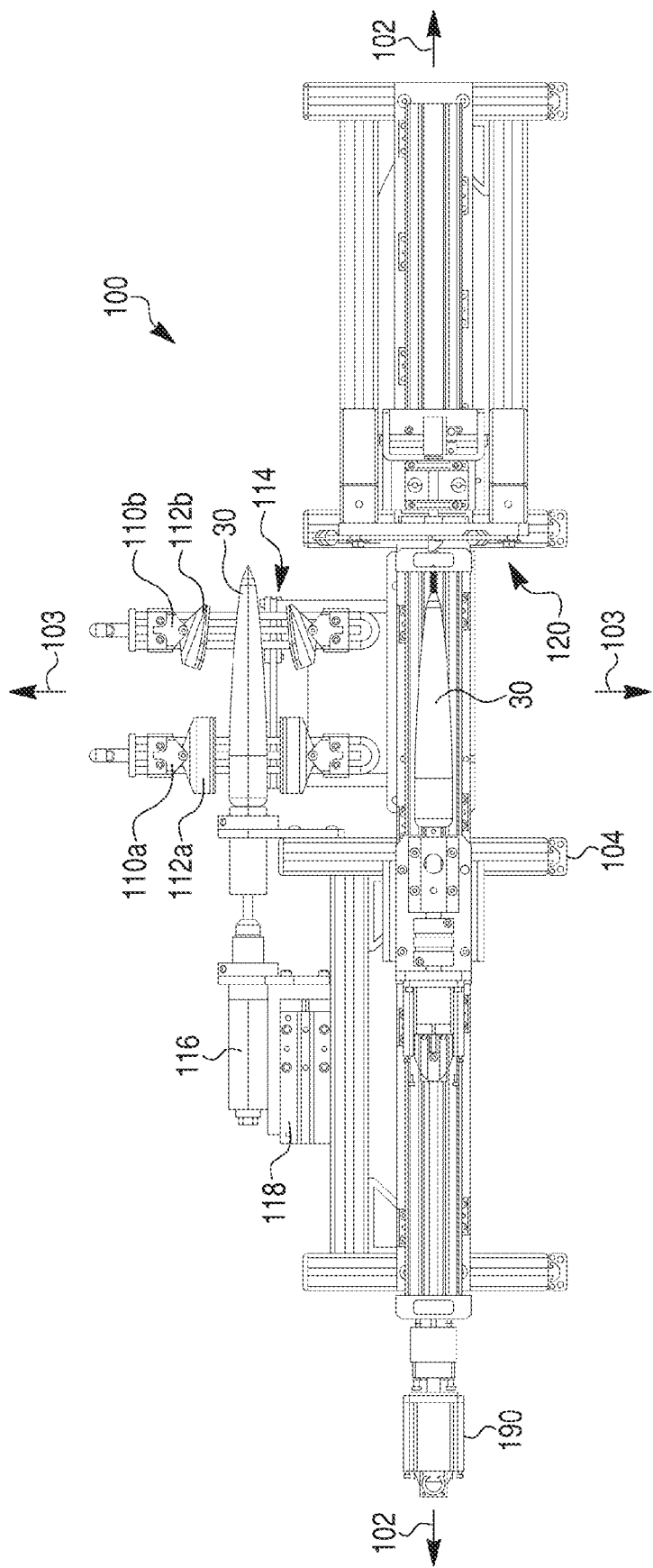

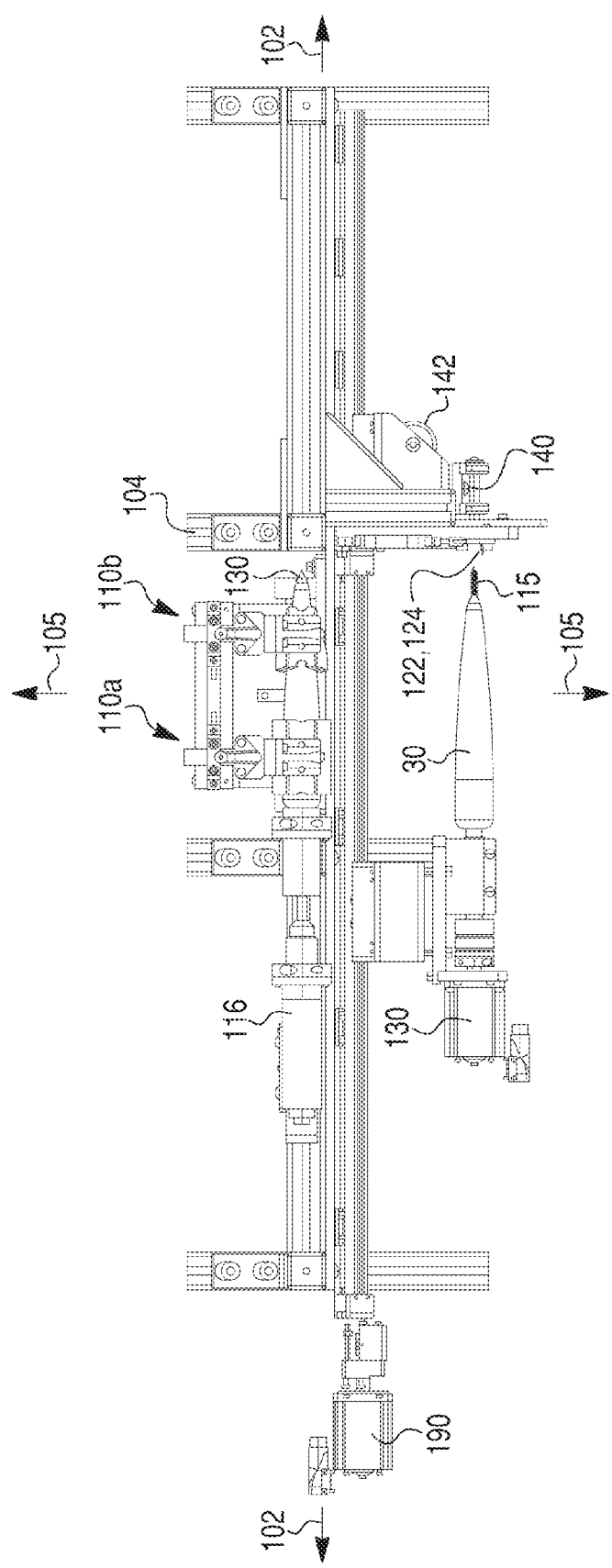

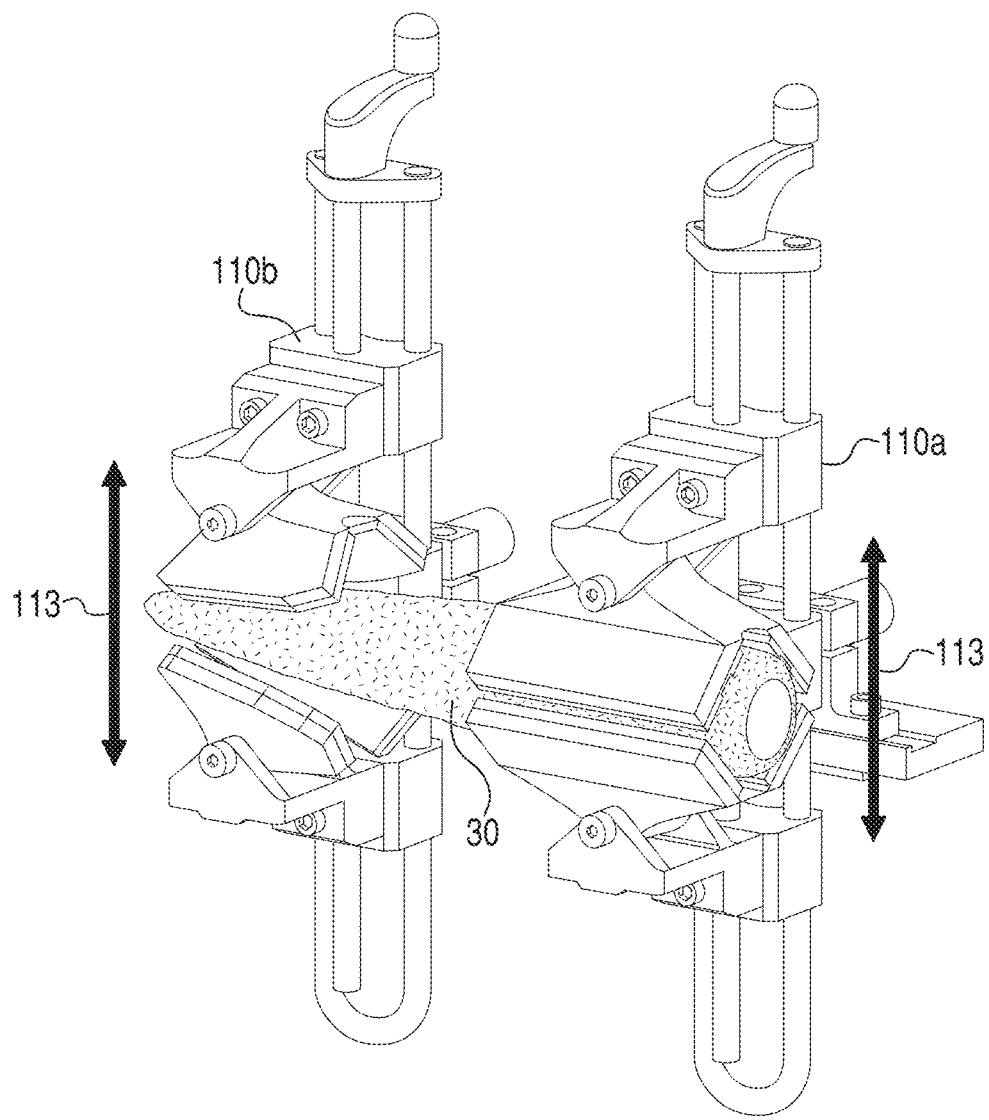

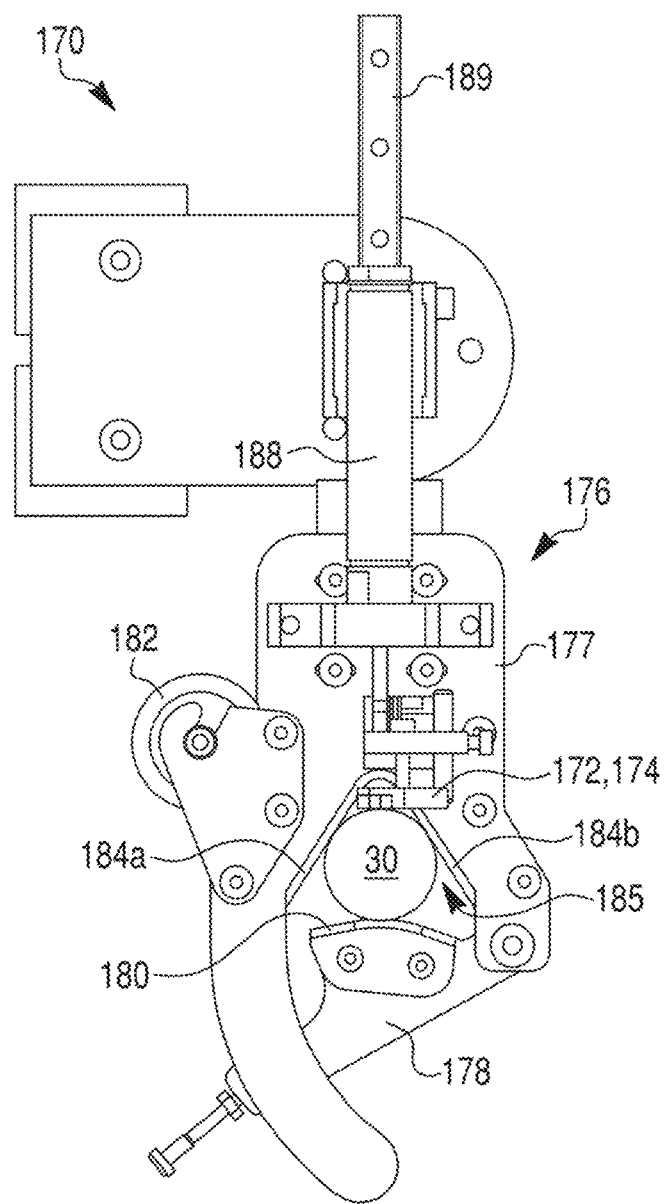

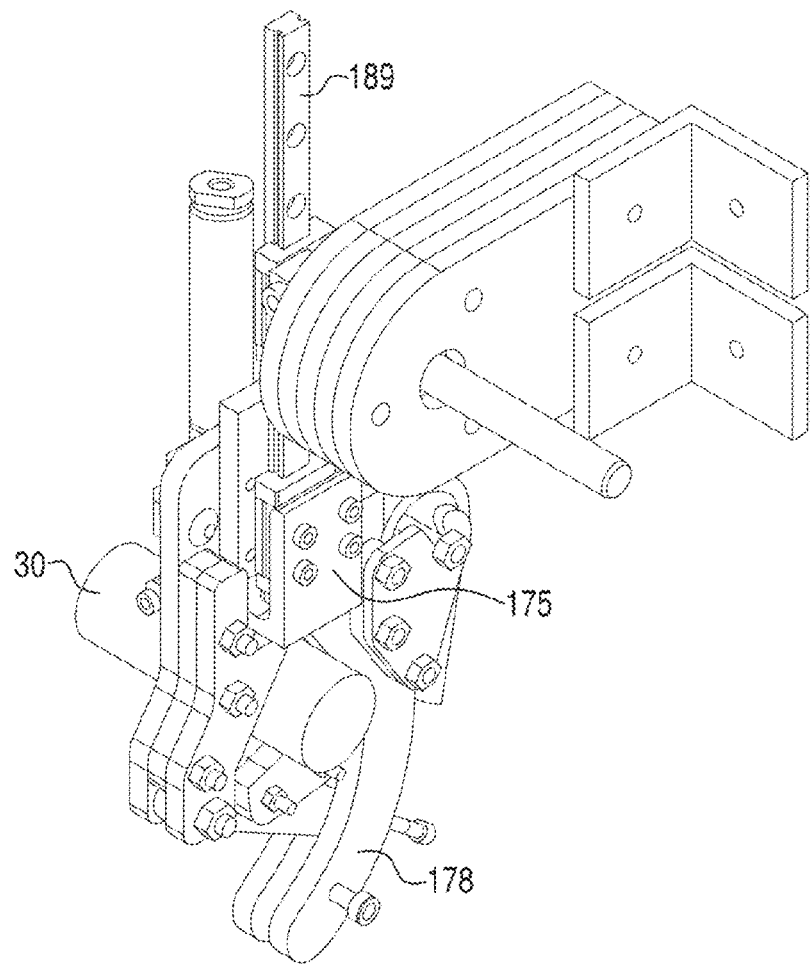

Fig. 13A

Position an Ear of Corn Within a Receiving Space Defined Between Opposed Engagement Elements of at Least One Clamp Assembly

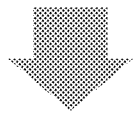

Selectively Adjust a Position of the Opposed Engagement Elements Relative to a Translation Axis that to Securely Engage the Ear in an Orientation that is Substantially Perpendicular to the Translation Axis

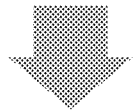

Insert a Threaded Portion of a Spindle Through at Least a Portion of the Pith of the Cob of the Ear, the Spindle Extending Substantially Perpendicularly to the Translation Axis and Having a Base Portion that Abuts a Proximal End of the Ear

Fig. 13B

Position at Least One Corn Kernel within an Inlet Portion of a Receiving Channel Defined by a Plate Assembly having at Least One Guide Plate and a Perforated Plate

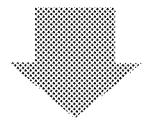

Effect Selective Oscillating Movement of a Perforated Plate of the Plate Assembly

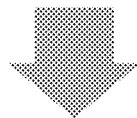

Selectively Activate a Pulley Assembly to Engage and Effect Movement of at Least One Corn Kernel from an Inlet Portion of the Receiving Channel of the Plate Assembly to an Outlet Portion of the Receiving Channel of the Plate Assembly, wherein the Perforated Plate Pulls Chaff Away from the at Least One Immature Corn Kernel During Movement of the Corn Kernel within the Receiving Channel

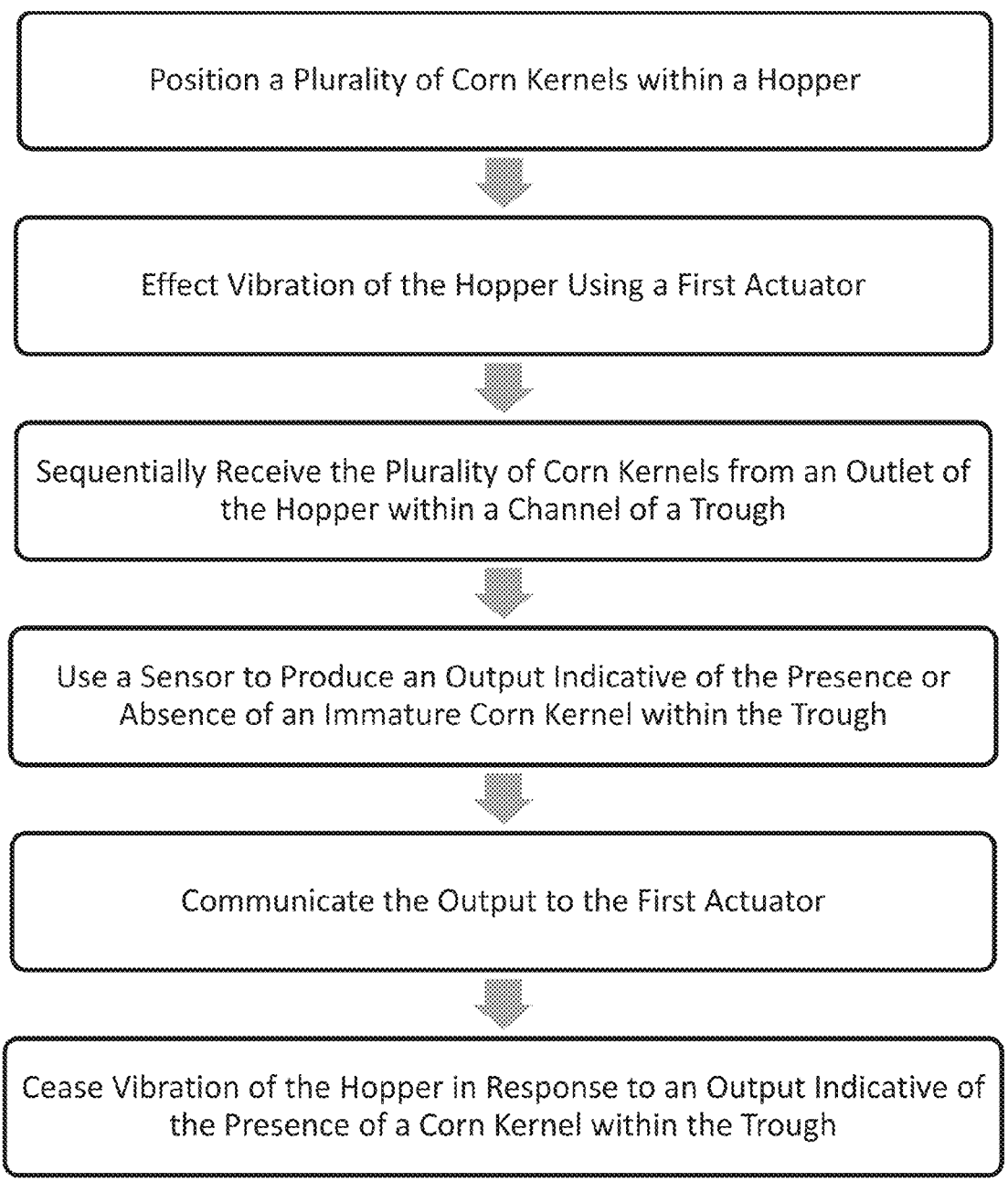

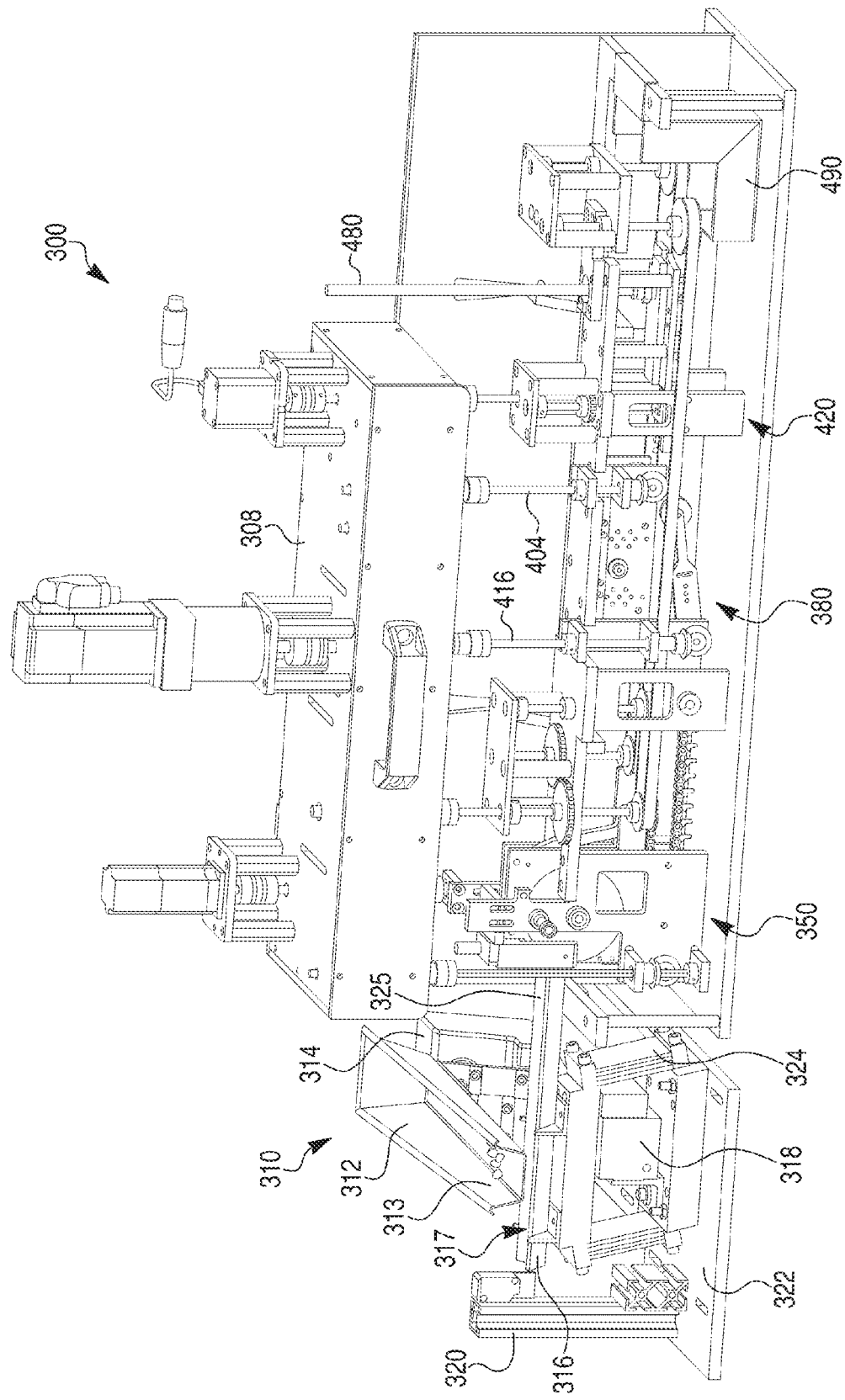

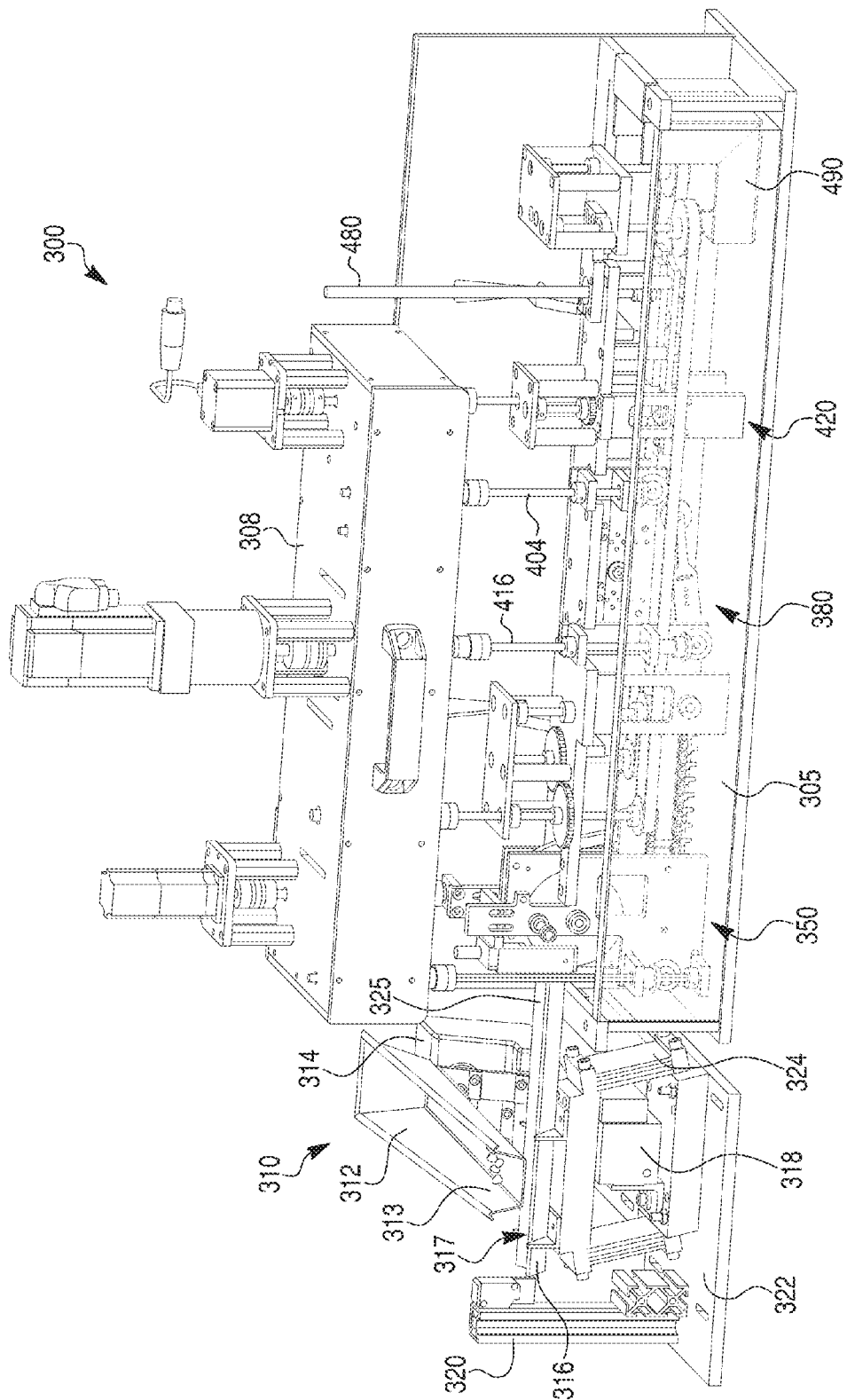

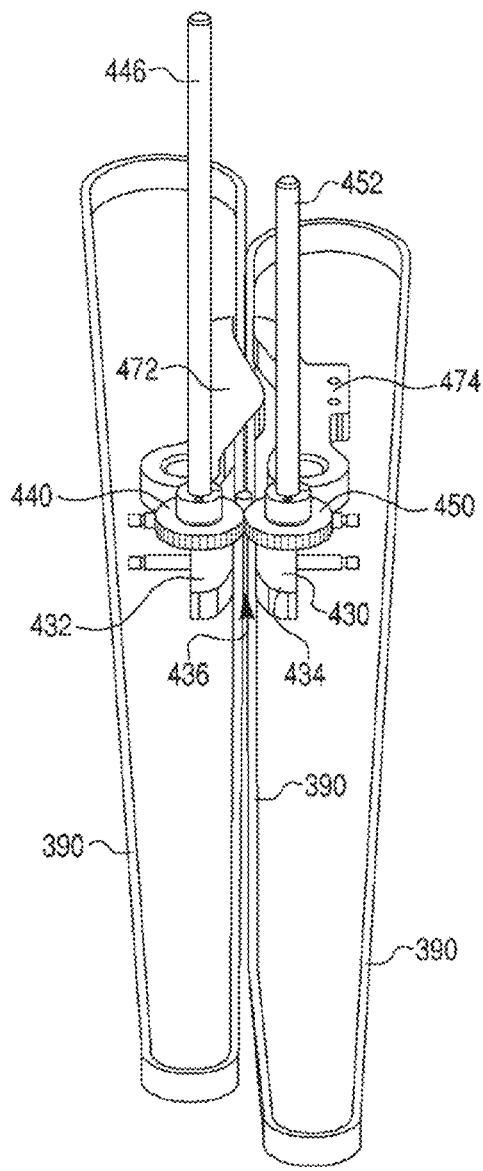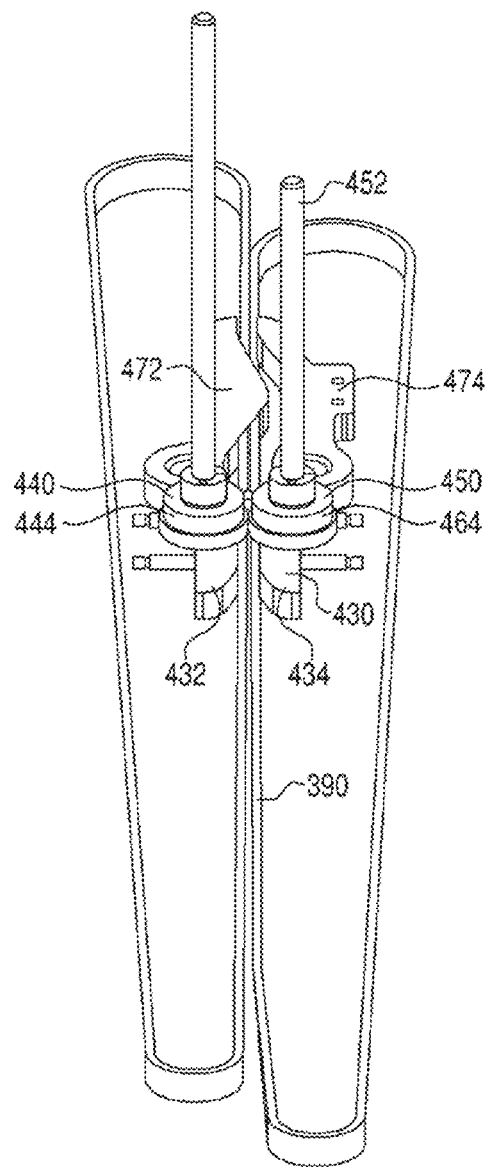

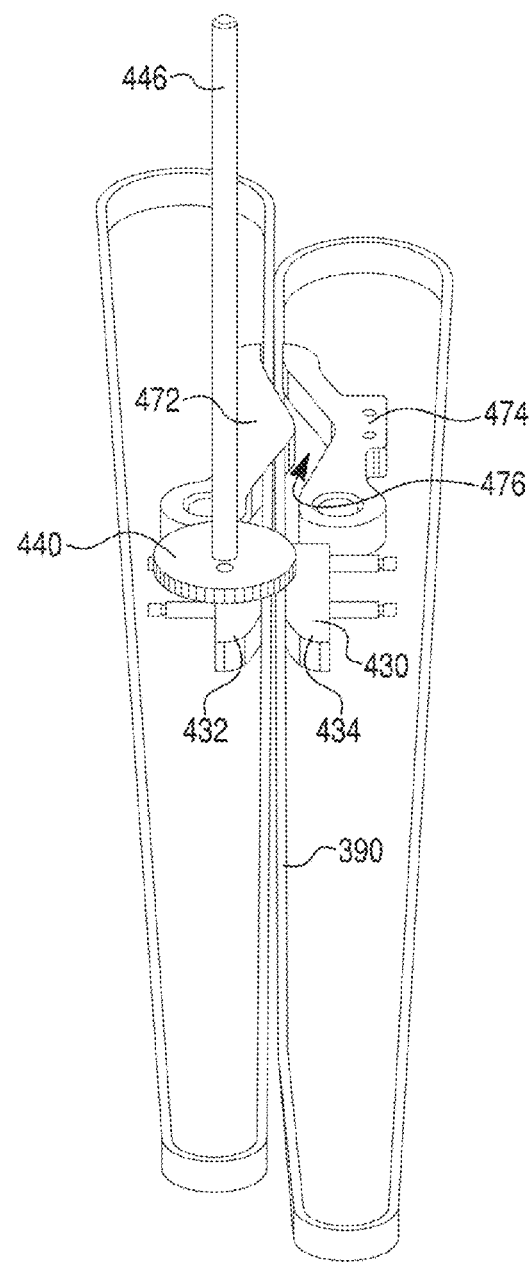

Fig. 24A
Automatically Extract a Monocot Embryo from an Immature Monocot Seed
Automatically Remove a Sample Portion of the Scutellum Section of the Monocot Embryo Without Damage to the Monocot Embryo
Genetically Analyze the Sample Portion of the Scutellum Section of the Monocot Embryo
Regenerate a Plant from the Remaining Portions of the Monocot Embryo

FIG. 25A

Position an Immature Corn Kernel within a Receptacle Defined about a Circumference of a Wheel

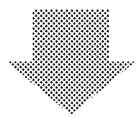

Rotate the Wheel About its Rotational Axis to Position the Immature Corn Kernel in a Second Rotational Position at which the Corn Kernel Exits the Receptacle into a Liquid Bath

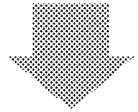

Receive the Corn Kernel Within a Receptacle Defined by a Feed Chain Positioned Within the Liquid Bath

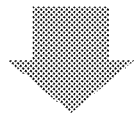

Effect Axial Movement of the Feed Chain to Transport the Corn Kernel

Position an Individual Corn Kernel within a Receiving Channel Defined by a Kernel Stabilizing Portion, which Supports the Corn Kernel in a Desired Position Rotate at Least One Wheel to Apply a Force to the Proximal End of the Corn Kernel as the Corn Kernel is Advanced Through the Receiving Channel

FIG. 25C

Deliver an Immature Corn Kernel from a Kernel Stabilizing Portion to a Channel Defined by Opposed Squeeze Bars

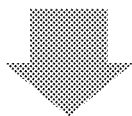

Use the Opposed Squeeze Bars to Apply a Radial Squeezing Force to the Immature Corn Kernel as it Moves through the Channel

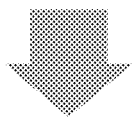

Position an Embryo Collection Tube in Fluid Communication with the Liquid Bath

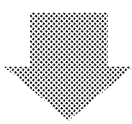

Following Extraction of the Embryo of the Immature Corn Kernel, Use Liquid Flow to Transport the Embryo Through the Embryo Collection Tube

FIG. 26

SYSTEMS FOR EXTRACTING MONOCOT EMBRYOS

CROSS-REFERENCE TO RELATED APPLICATIONS

This application claims priority to and the benefit of the filing date of U.S. Provisional Patent Application No. 61/949,819, entitled "Methods and Systems for Extracting Monocot Embryos," filed Mar. 7, 2014, which is incorporated herein by reference in its entirety.

FIELD

The present invention relates generally to systems and methods for extracting monocot embryos from monocot seeds and, more particularly, to systems and methods for extracting monocot embryos from monocot seeds without damaging the monocot embryos.

BACKGROUND

Various large-scale systems have been proposed for extracting monocot embryos; however, these systems have generally been designed to perform in a manner that damages the monocot embryos during extraction and extracts portions of the monocot seed other than the monocot embryo. Current systems and methods for extracting monocot embryos typically extract the embryos through a distal end (crown) of the seeds while the seeds are still on their carrier. For example, a corn embryo is typically extracted by forcing the embryo through the crown of a kernel while the kernel is attached to a cob. The anatomy of corn kernels and other monocot seeds generally requires application of significant forces to extract embryos through the distal end (crown) of the seeds. These significant forces create undesirable stress on the embryo. Typically, current monocot embryo extraction methods also require sieving of the extracted material to ensure separation of the embryo from other materials. The sieving step requires application of further force to the embryos, thereby resulting in further stress on the embryos. Additionally, systems for extracting dicot embryos are not particularly suitable for extracting monocot embryos. Thus, there is a need for alternative methods to extract isolated, undamaged monocot embryos from monocot seeds.

SUMMARY

Disclosed herein are methods and systems which extract a monocot embryo from a singulated monocot seed that generally has been removed from its biological carrier, which as is known to those of skill in the art, may be a pod, a cob, or other plant structure associated with a seed. Herein, it may be referred to as a biological carrier to distinguish it from a part of a device that may carry objects. Those of skill in the art can distinguish the usage of the term. A monocot seed can be obtained and then placed in a liquid bath to achieve a desired orientation. In general, methods may comprise a three applied to the monocot seed to extract the monocot embryo. Optionally, the monocot embryo may be released into the liquid bath. In exemplary aspects, the monocot seed can be an immature monocot seed.

Methods and systems disclosed herein may comprise automatically isolating a monocot embryo from a monocot seed having a proximal end and an opposed distal end. For orientation and understanding, prior to removal of the monocot seed from a biological carrier, the proximal end of the monocot seed is attached to the biological carrier and the distal end of the monocot seed is spaced from the biological carrier. An isolated monocot seed having an opening in the proximal end of the monocot seed can be provided following removal of the monocot seed from the biological carrier. At least a portion of the proximal end of the monocot seed may be removed to form the opening in the proximal end of the monocot seed without damage to the monocot embryo. The monocot embryo can be extracted through the opening in the proximal end of the monocot seed, and the monocot embryo is generally undamaged following extraction. Following extraction of the monocot embryo, the undamaged monocot embryo may retain an ability to grow with full viability and vigor. In exemplary aspects, the monocot seed can be an immature monocot seed.

Methods and systems disclosed herein may comprise regenerating a plant from a monocot embryo of a monocot seed. In exemplary aspects, the monocot seed can be an immature monocot seed. The monocot embryo can be automatically extracted from the monocot seed without damage to the monocot embryo. The monocot embryo can have a meristematic section and a scutellum section. A sample portion of the scutellum section of the monocot embryo can be removed without damage to the extracted monocot embryo. The sample portion and the viable embryo can be tracked and identified in a 1 to 1 relationship. The sample portion of the scutellum section of the monocot embryo can be genetically analyzed, and a plant can be regenerated from the remaining portion of the monocot embryo (including the meristematic section). Methods and systems disclosed herein may permit individual analysis of each of a plurality of monocot seeds. A monocot embryo from each respective monocot seed of a plurality of monocot seeds can be automatically extracted, and a sample portion of the scutellum section of the monocot embryo of each respective monocot seed can be removed without damage to the monocot embryo. A sample portion of the embryo, such as a scutellum section of a monocot embryo, of each respective monocot seed can be analyzed, for example, genetically analyzed, and the remaining portions of the monocot embryo of each respective monocot seed can be selected or discarded on the basis of the genetic analysis of the sample portion of the scutellum section of the monocot embryo of each respective monocot seed. For example, a sample may be obtained from a portion of the embryo, and may comprise one or more cells. It is contemplated that the sample from the embryo can be as small as a single nucleus. The remaining portions of the monocot embryo(s) of at least one monocot seed of the plurality of monocot seeds can be selected, and at least one plant can be regenerated from the remaining portions of each respective selected monocot embryo.

Disclosed herein, in one aspect, is a system for removing chaff from a corn kernel. The system can have a plate assembly and a pulley assembly. The plate assembly can have at least one guide plate and a perforated plate. The perforated plate can have a first surface and an opposed second surface and define a plurality of bores that extend from the first surface to the second surface relative to a first axis. The at least one guide plate and the first surface of the perforated plate can cooperate to define a receiving channel that extends parallel to a second axis and has an inlet portion and an outlet portion, with the second axis being substantially perpendicular to the first axis. The inlet portion of the receiving channel can be configured to receive at least one corn kernel. The perforated plate can be configured for selective oscillating movement relative to a third axis that is substantially perpendicular to both the first and second axes. The first surface of the perforated plate can have a desired surface roughness. The pulley assembly can be configured to effect movement of the at least one seed relative to the second axis from the inlet portion of the receiving channel of the plate assembly to the outlet portion of the receiving channel of the plate assembly. The at least one guide plate of the plate assembly can be configured to restrict movement of the at least one corn kernel relative to the third axis. During oscillating movement of the perforated plate, the perforated plate can be configured to pull chaff away from the at least one corn kernel as the corn kernel moves relative to the second axis within the receiving channel of the plate assembly.

In a further aspect, disclosed herein is a system for extracting an embryo from a corn kernel. The system can have a longitudinal axis, a liquid bath, a belt assembly, a force application assembly, and an embryo collection tube. The belt assembly can be positioned within the liquid bath and be configured to sequentially advance a plurality of corn kernels relative to the longitudinal axis of the system. Optionally, the force application assembly can be positioned within the liquid bath. The three application assembly can include a kernel stabilizing portion, at least one wheel, and a squeezing portion. The kernel stabilizing portion can define a receiving channel that is configured to receive and support an individual corn kernel in a desired position as the corn kernel is advanced relative to the longitudinal axis of the system. In the desired position, at least a portion of a proximal end of the corn kernel can extend upwardly from the kernel stabilizing portion relative to a vertical axis that is substantially perpendicular to the longitudinal axis of the system. The at least one wheel can be operatively positioned relative to the kernel stabilizing portion. The at least one wheel can be selectively rotatable to apply a force to the proximal end of the corn kernel as the corn kernel is advanced through the receiving channel of the kernel stabilizing portion relative to the longitudinal axis of the system. The force applied by the at least one wheel can be sufficient to form a hole or opening in the proximal end of the corn kernel. The squeezing portion can have first and second opposed squeeze bars that are spaced apart relative to a transverse axis that is substantially perpendicular to the vertical axis and the longitudinal axis of the system. The opposed squeeze bars can cooperate to define a channel that is configured to receive a corn kernel from the kernel stabilizing portion as the corn kernel is advanced relative to the longitudinal axis of the system. At least one of the opposed squeeze bars can be biased toward the other squeeze bar relative to the transverse axis. The opposed squeeze bars can be configured to apply a radial squeezing force to the corn kernel as it moves through the channel of the squeezing portion relative to the longitudinal axis. The embryo collection tube can be positioned in fluid communication with the liquid bath and configured to receive liquid containing an embryo extracted from a corn kernel in response to application of the radial squeezing force by the squeezing portion of the system.

Optionally, the system for extracting an embryo from a corn kernel can include a singulation assembly configured to receive a plurality of corn kernels and separate a single corn kernel from the remaining corn kernels of the plurality of corn kernels. Optionally, the system for extracting an embryo from a corn kernel can also include an indexing assembly configured to receive a single corn kernel from the singulation assembly and to transport the single corn kernel to the belt assembly in a desired orientation. In exemplary aspects, the indexing assembly can be at least partially positioned within the liquid bath. The singulation assembly can have an outlet, and the indexing assembly can have an inlet. The outlet of the singulation assembly can be positioned in communication with the inlet of the indexing assembly.

Also disclosed herein, in various aspects, are methods of using one or more of the disclosed systems to singulate a kernel, remove chaff from a kernel, and/or extract a corn embryo from a kernel.

BRIEF DESCRIPTION OF THE FIGURES

FIG. 3A is a side perspective view of an exemplary seed removal system as disclosed herein. FIG. 3B is a top perspective view of the seed removal system of FIG. 3A.

FIG. 4A is a perspective view of clamp assemblies of an exemplary seed removal system, as disclosed herein.

FIG. 10B is an end perspective view of the cob-following cutting assembly of FIG. 10A. FIG. 10D is a rear perspective view of the cob-following cutting assembly of FIG. 10A.

FIG. 13A is a flowchart depicting an exemplary method of obtaining an isolated corn kernel. FIG. 13B is a flowchart depicting an exemplary method of removing chaff from a corn kernel. FIG. 13C is a flowchart depicting an exemplary method of singulating a corn kernel as disclosed herein.

FIG. 14A is a perspective view of an exemplary embryo extraction system as disclosed herein, shown with its water trough removed for clarity. FIG. 14B is a perspective view of the embryo extraction system of FIG. 14A, shown with its water trough in place.

FIG. 18B is an isolated top perspective view of an exemplary force application assembly of the embryo extraction system of FIG. 14A. FIG. 18C is an isolated top perspective view of another exemplary force application assembly of the embryo extraction system of FIG. 14A. FIG. 18E is an isolated top perpective view of another exemplary force application assembly of the embryo extraction system of FIG. 14A.

FIG. 24A is a flow chart depicting an exemplary method of regenerating a plant from portions of a monocot embryo following extraction from a monocot seed.

FIG. 25A is a flowchart depicting an exemplary method of placing a corn kernel in a liquid bath as disclosed herein. FIG. 25C is a flowchart depicting an exemplary method of applying a force to extract a corn embryo through an opening of a corn kernel as disclosed herein.

FIG. 26 is a table showing a comparison of the condition of corn embryos extracted using various experimental methods, as further described herein.

DETAILED DESCRIPTION

Figure 1:
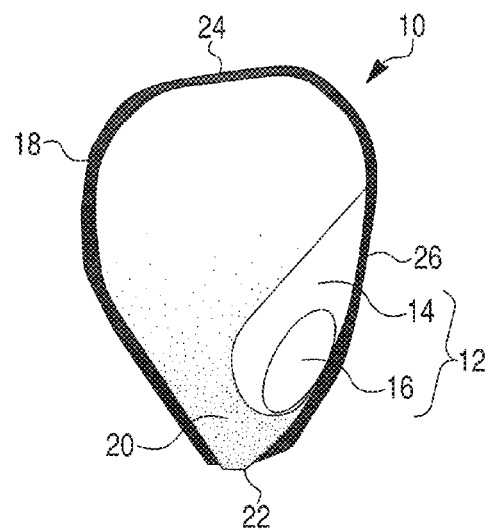
FIG. 1 is a schematic diagram of an immature maize seed. The pericarp, endosperm, and embryo of the immature maize seed are labeled. As shown, the embryo comprises scutellum tissue and meristematic tissue.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a", "an", and "the" include plural referents unless the context clearly dictates otherwise. Thus, for example, reference to "a sample portion" can include a plurality of such sample portions, and so forth. All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

I. Overview

The present invention comprises methods and systems for extracting the monocot embryos of isolated monocot seeds, such as, for example, isolated immature monocot seeds. It is contemplated that disclosed methods and systems can be used to extract the monocot embryo of an individual monocot seed without damaging the monocot embryo. In exemplary aspects, it is contemplated that systems and methods disclosed herein can accomplish extraction of corn embryos using about 20% of the force required to extract corn embryos through the crown of a kernel. It is further contemplated that the embryos extracted using the systems and methods disclosed herein can be sufficiently separated from other materials that sieving and other mechanical embryo separation steps are not required.

In operation, the systems and methods disclosed herein can permit extraction of embryos from monocot seeds on a seed-by-seed basis. It is contemplated that the seed-by-seed approaches disclosed herein can advantageously permit improved cleaning and sterilization of individual seeds, for example, allowing sterilization of the entire surface of the seed, compared to batch processes. It is contemplated that disclosed methods and systems can permit tracking and/or analysis of individual monocot embryos following extraction of the monocot embryos from respective monocot seeds. It is contemplated that disclosed methods and systems can permit the regeneration of a plant using an individual extracted monocot embryo.

Exemplary methods of extracting a monocot embryo after orienting a monocot seed within a liquid bath, automatically extracting monocot embryos, and regenerating a plant from a monocot seed (e.g., an immature monocot seed) are disclosed. Unless otherwise stated, it is contemplated that, although these exemplary methods are described separately, the steps of any one of the disclosed methods can be used in combination with the steps of any of the other disclosed method to arrive at a method of extracting a monocot embryo from a monocot seed. Thus, it is contemplated that one or more steps of a disclosed method of extracting a monocot embryo after orienting a monocot seed within a liquid bath can be used in combination with one or more steps of the disclosed methods of automatically extracting monocot embryos and/or regenerating a plant from a monocot seed. Similarly, it is contemplated that one or more steps of disclosed methods of automatically extracting monocot embryos can be used in combination with one or more steps of disclosed methods of extracting a monocot embryo after orienting a monocot seed within a liquid bath and/or regenerating a plant from a monocot seed. It is further contemplated that one or more steps of disclosed methods of regenerating a plant can be used in combination with one or more steps of disclosed methods of extracting a monocot embryo after orienting a monocot seed within a liquid bath and/or automatically isolating monocot embryos. It is further contemplated that, unless otherwise stated, any of the steps of disclosed embryo extraction methods can be performed in an automated fashion.

FIG. 1 depicts various components of a corn (e.g., maize) seed 10 (corn kernel), including the endosperm 20 and the embryo 12. As shown in FIG. 1, the endosperm 20 borders the embryo 12, and the embryo and endosperm are encased by the pericarp 18. Depending on the age of the seed 10, the endosperm 20 may be starchier toward the distal end 24 of the seed and more gel-like toward the proximal end 22 of the seed. The seed 10 has side portions 26 extending between the proximal end 22 and the distal end 24.

Figure 2A:
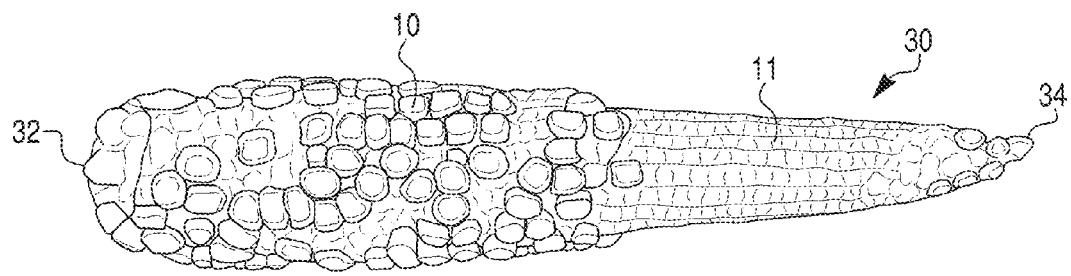
FIG. 2A depicts an exemplary biological carrier (e.g., cob) for carrying monocot seeds.

FIG. 2A depicts an ear 30 of corn. As shown, the ear 30 has a proximal end 32 (where the stalk is/was attached) and an opposed distal end 34. As shown, the ear has fertilized corn seeds (kernels) 10. However, it is understood that at least the distal portion of some ears (near the distal end 34) can have unfertilized corn seeds (kernels) 11.

Figure 2B:
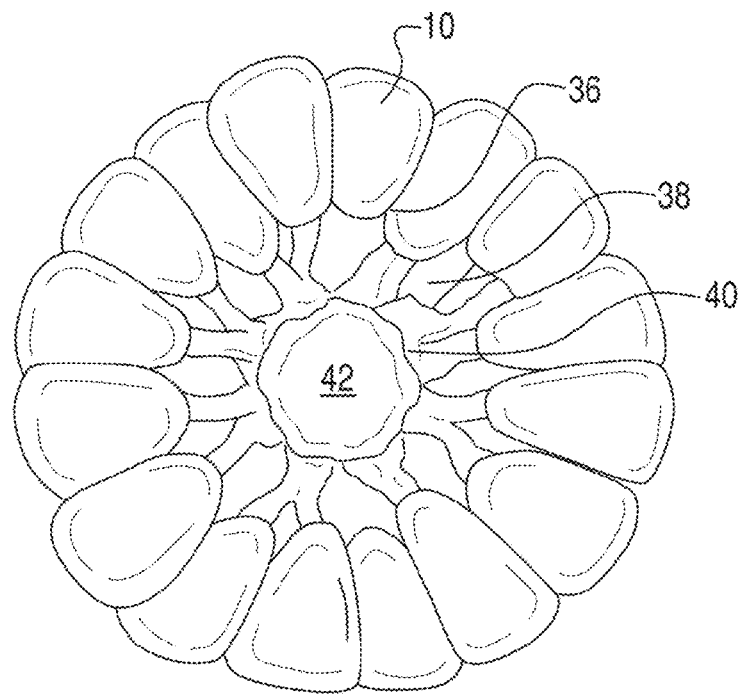
FIG. 2B is a cross-sectional view of the biological carrier of FIG. 2A.
Figure 4C:
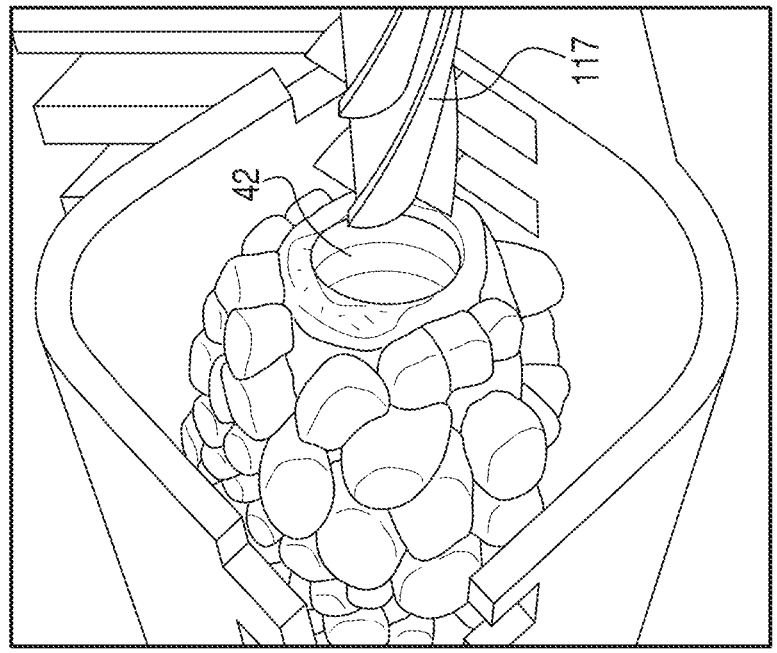
FIG. 4C is a close-up end perspective view of the biological carrier of FIG. 4B, following removal of the stalk with a stalk removal tool.
Figure 4B:
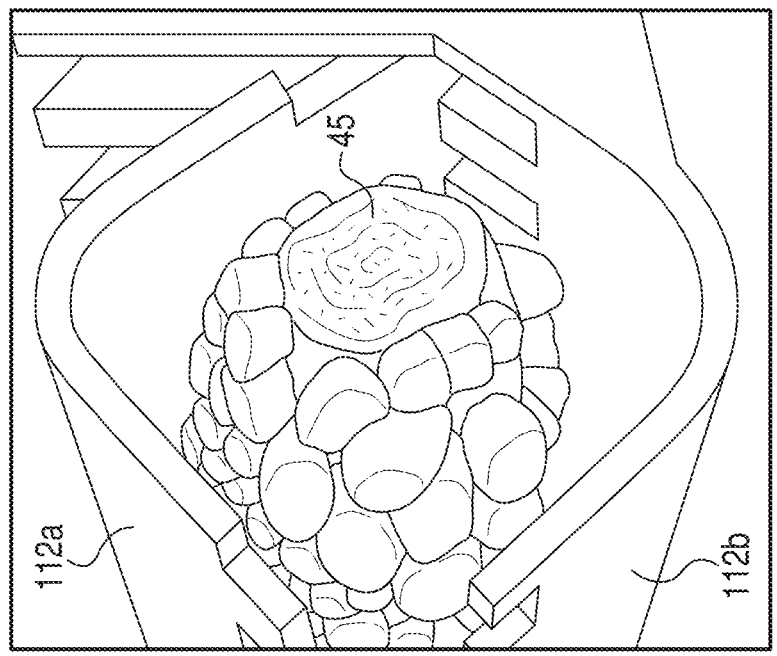
FIG. 4B is a close-up end perspective view of a biological carrier positioned within clamp assemblies of an exemplary seed removal system, as disclosed herein. As shown, the biological carrier is attached to a portion of its stalk.

FIG. 2B is a cross section of an ear 30 of corn. As shown the corn kernels 10 can define the outer circumference of the ear 30. Moving radially inwardly from the corn seeds (kernels) 10, the ear 30 can include bees' wings 36, chaff 38, a woody ring 40, and a pith 42.

As used herein, the term "cob" refers to the biological carrier for corn, not including the corn seeds (kernels).

As used herein, the term "ear" refers to a cob with attached corn seeds (kernels) and may or may not be wrapped in husk.

As used herein, and as shown in FIG. 1, "embryo" or "monocot embryo" 12 consists of a meristematic section 16 and scutellum section 14.

As used herein, the "meristematic section" of the monocot embryo refers to the essential genetic information and embryonic structures required for the monocot embryo to grow into a plant.

As used herein, the "scutellum section" of the monocot embryo refers to the tissue that generally surrounds the meristematic section within the monocot embryo and stores nutrients mobilized during germination of a monocot seed. The scutellum section generally functions as a barrier between the endosperm of a monocot seed and the meristematic tissue of a monocot embryo. As used herein, an "immature" monocot seed refers to a monocot seed harvested within a selected number of days after pollination. As used herein, an "immature" monocot seed refers to a monocot seed harvested after fertilization but prior to physiological maturity and, except in the case of hard coat seeds, does not germinate in water without external nutrients. In some examples, the harvest is contemplated to occur between 200 and 750 Growth Degree Units (GDUs) after pollination.

As used herein, an "undamaged" embryo or an embryo "without damage" refers to an embryo that does not exhibit substantial bruising after being extracted and retains an ability to grow with full viability and vigor. For example, a monocot embryo is "undamaged" following extraction if the viability and vigor of the monocot embryo is substantially unchanged following extraction. In exemplary aspects, it is contemplated that a monocot embryo is "undamaged" following extraction if the viability and vigor of the monocot embryo are at least 50% of the viability and vigor of monocot embryos extracted using conventional hand extraction methods. In one exemplary aspect, a monocot embryo is "undamaged" following extraction if the viability and vigor of the monocot embryo are at least 60% of the viability and vigor of monocot embryos extracted using conventional hand extraction methods. In another exemplary aspect, a monocot embryo is "undamaged" following extraction if the viability and vigor of the monocot embryo are at least 70% of the viability and vigor of monocot embryos extracted using conventional hand extraction methods. In another exemplary aspect, a monocot embryo is "undamaged" following extraction if the viability and vigor of the monocot embryo are at least 80% of the viability and vigor of monocot embryos extracted using conventional hand extraction methods. In still another exemplary aspect, a monocot embryo is "undamaged" following extraction if the viability and vigor of the monocot embryo are at least 90% of the viability and vigor of monocot embryos extracted using conventional hand extraction methods. In a further exemplary aspect, a monocot embryo is "undamaged" following extraction if the viability and vigor of the monocot embryo are at least 95% of the viability and vigor of monocot embryos extracted using conventional hand extraction methods. In general, viability refers to the ability of the embryo to germinate and develop into a plantlet under tissue culture or growth medium conditions known to those skilled in the art. In general, vigor refers to the growth and development of the resultant plantlet, up to and including male and female flowering, kernel development, reached kernel physiological maturity.

In other exemplary aspects, it is contemplated that a monocot embryo is "undamaged" following extraction if the germination of the monocot embryo generates a viable plantlet.

As used herein, the term "automatic" or "automatically" refers to the use of mechanical, electrical, software, imaging, vision-based and/or other known automation-based technologies to augment processes typically performed by human interaction.

II. Methods of Extracting Monocot Embryos from Immature Monocot Seeds

Figure 22:
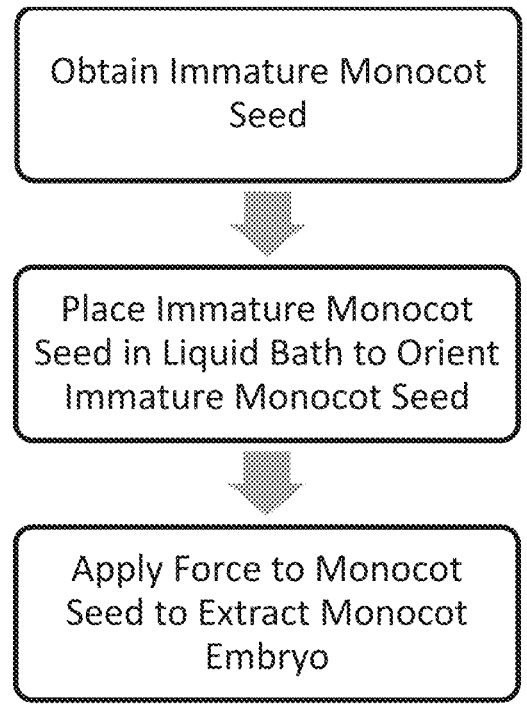
FIG. 22 is a flow chart depicting an exemplary method of extracting a monocot embryo from a monocot seed as disclosed herein.

In various aspects, and with reference to FIG. 22, a method of extracting a monocot embryo from a monocot seed is provided. In these aspects, a method can comprise obtaining a monocot seed, for example, an immature monocot seed. Optionally, in one aspect, a method can further comprise placing the monocot seed in a liquid bath. In an aspect, it is contemplated that placement of the monocot seed in the liquid bath can cause the monocot seed to orient itself in a desired orientation. For example, it is contemplated that positioning of a corn kernel within a liquid bath can cause the corn kernel to orient itself with a distal end (crown) of the kernel facing away from a surface of the liquid bath and a proximal end of the kernel facing toward the surface of the liquid bath. Alternatively, the method can comprise placing the monocot seed in the desired orientation using other means, including, for example and without limitation, manually positioning the crown of the monocot seed (e.g., corn kernel) onto a vacuum cup that holds the monocot seed in the desired orientation, or using conventional machine vision techniques to locate and then automatically (e.g., robotically) pick and place monocot seeds (e.g., corn kernels) in the desired orientation as needed. In an aspect, a method can further comprise applying force to extract the monocot embryo from the monocot seed. Optionally, when the immature monocot seed is positioned in a liquid bath, the force can be applied such that the monocot embryo is released into the liquid bath. In an aspect, it is contemplated that the monocot seed can optionally be wholly submerged in the liquid bath during the step of applying force to the monocot embryo. Alternatively, it is contemplated that the distal end of the monocot seed can be submerged in the liquid bath while at least a portion of the proximal end is positioned above the surface of the liquid bath. Optionally, it is contemplated that the entire monocot seed can be positioned above the surface of the liquid bath such that the monocot embryo is released into the liquid bath upon extraction. Optionally, in an aspect, it is contemplated that a monocot seed can be a corn seed (kernel) or a sorghum seed or a wheat seed or a rice seed. In this aspect, the monocot seed can optionally be an immature monocot seed.

In further aspects, it is contemplated that a monocot embryo can be undamaged following extraction from the monocot seed. In these aspects, it is contemplated that, following extraction of a monocot embryo from the monocot seed, the monocot embryo can retain an ability to grow with full viability and vigor. More generally, it is contemplated that the monocot embryo can retain the ability to germinate following extraction from the monocot seed. Optionally, in additional aspects, it is contemplated that a monocot embryo of the monocot seed can be extracted such that the endosperm of a monocot seed is not substantially extracted from the monocot seed. It is still further contemplated that an extracted monocot embryo of a monocot seed can be sufficiently separated from other material following extraction such that sieving of the extracted monocot embryo is not required.

In an aspect, the monocot seed can have a proximal end and an opposed distal end. In an aspect, it is contemplated that, prior to removal of the immature monocot seed from a biological carrier, the proximal end of the monocot seed can be attached to the biological carrier and the distal end of the monocot seed can be spaced from the biological carrier. In exemplary aspects, when the monocot seed is a corn kernel, the proximal end of the corn kernel can comprise a tip cap of the corn kernel and the distal end of the corn kernel can comprise a crown of the corn kernel.

Optionally, in some aspects, it is contemplated that an opening or hole can be formed in the proximal end of the monocot seed. In an aspect, an opening or hole in the proximal end of the monocot seed can optionally be formed before force is applied to the monocot seed. In an aspect, it is contemplated that the monocot seed can be positioned in any location permitting application of force to the monocot seed as disclosed herein. In aspects, it is contemplated that an opening or hole in the proximal end of the monocot seed can optionally be formed before the monocot seed is obtained. Alternatively, in other optional aspects, it is contemplated that an opening or hole in the proximal end of the monocot seed can be made after the monocot seed has been obtained. Optionally, in some aspects, it is contemplated that the method can further comprise cleaning at least the proximal end of the monocot seed. In aspects, a step of cleaning at least the proximal end of the monocot seed can comprise sterilizing the surface of the monocot seed. In other exemplary aspects, it is contemplated that a monocot seed can be cleaned before the monocot seed is obtained. Optionally, in aspects, the surface of the monocot seed can be sterilized before the monocot seed is obtained.

Optionally, in other aspects, it is contemplated that the monocot embryo can be extracted from the monocot seed without the need for forming an opening or hole in the monocot seed. In these aspects, it is contemplated that at least a portion of the monocot seed can be placed in the liquid bath. Optionally, it is contemplated that the monocot seed can optionally be wholly submerged in the liquid bath prior to the application of force to the monocot seed. Alternatively, it is contemplated that the distal end of the monocot seed can optionally be submerged in the liquid bath while at least a portion of the proximal end is positioned above the surface of the liquid bath. It is further contemplated that the entire monocot seed can be positioned above the surface of the liquid bath prior to and during the application of force to the monocot seed.

In exemplary aspects, when an opening or hole is formed in the monocot seed, it is contemplated that the step of applying force to extract the monocot embryo can comprise applying pressure to at least one side portion of the monocot seed to force the monocot embryo through the opening or hole in the proximal end of the monocot seed. In these aspects, the monocot seed comprises side portions extending from the proximal end to the distal end of the seed. It is contemplated that the step of applying pressure to at least one side portion of the monocot seed can comprise supporting the monocot seed in a selected orientation while pressure is applied to the at least one side portion of the monocot seed. In an exemplary aspect, the step of applying pressure to at least one side portion of the monocot seed can comprise applying a rolling force to the at least one side portion moving in a direction from the distal end of the seed toward the proximal end of the seed. In other exemplary aspects, when an opening or hole is not formed in the monocot seed, it is contemplated that the step of applying force to extract the monocot embryo can comprise applying pressure to the at least one side portion of the monocot seed to split a portion of the proximal end of the monocot seed and to force the monocot embryo through an opening or hole defined by the split portion of the monocot seed. In these aspects, it is contemplated that the step of applying pressure to the at least one side portion of the monocot seed can comprise supporting the monocot seed in a selected orientation while pressure is applied to the at least one side portion of the monocot seed.

Optionally, in some aspects, the monocot seed can be wholly submerged in the liquid bath when the force is applied to the monocot seed. In these aspects, it is contemplated that the selected orientation of the monocot seed can correspond to the proximal end of the monocot seed being pointed toward the surface of the liquid bath. In other aspects, it is contemplated that the monocot seed can be only partially submerged in the liquid bath when the force is applied to the monocot seed. In these aspects, it is contemplated that the selected orientation of the monocot seed can correspond to the distal end of the monocot seed being submerged in the liquid bath while at least a portion of the proximal end of the monocot seed is positioned above the surface of the liquid bath. In still other aspects, the entire monocot seed can be positioned above the liquid bath.

In exemplary aspects, it is contemplated that a monocot seed can be positioned in the selected orientation by positioning the monocot seed in the liquid bath and permitting the monocot seed to orient in the liquid bath such that the proximal end of the monocot seed points upwardly (toward the surface of the liquid bath). In these aspects, it is contemplated that monocot seeds having excess material (e.g., "bee's wings" or cob material), impurities, or trapped air may not orient as desired. In order to address the issue of trapped air, it is contemplated that the methods as disclosed herein can optionally comprise agitating the liquid bath to cause the trapped air to escape from the monocot seeds. It is contemplated that optional steps of cleaning and/or sterilizing the monocot seed such as those as disclosed herein can address the issues of excess material or other impurities. In other exemplary aspects, it is contemplated that a monocot seed can be positioned in the selected orientation using conventional means, including, for example and without limitation, at least one of machine visualization with robotic sorting and manipulation, vibratory orientation and feeding, roller sorting and feeding, and manual orientation.

It is contemplated that an opening or hole in the proximal end of the monocot seed can be formed by any conventional means, such as, for example, conventional force application means, including conventional cutting means, conventional ripping means, conventional tearing means, conventional squeezing means, conventional crushing means, and the like. In exemplary aspects, an opening or hole in the proximal end of the monocot seed can be formed by a conventional knife blade. Optionally, in further exemplary aspects, force can be applied to the proximal end of the monocot seed at a location between the tip cap (most proximal tip) of the monocot seed and the monocot embryo within the seed to form the hole. In these aspects, force can be applied to the proximal end of the monocot seed at a location spaced a selected distance from the tip cap to form an opening or hole. It is contemplated that the selected distance from the tip cap can optionally range from about 0.1 mm to about 3 mm. It is further contemplated that the selected distance from the tip cap can optionally range from about 0.25 mm to about 1.5 mm.

Optionally, in exemplary aspects, it is contemplated that the step of forming the hole in the proximal end of the monocot seed can be an iterative process in which force is applied at multiple locations until a desired location for the hole is identified. In these aspects, it is contemplated that a first force can be applied proximate the tip cap of the monocot seed. If the location of the first force is not a desired location for an opening or hole as disclosed herein, then a second force can be applied at a second location positioned closer to the monocot embryo. It is contemplated that this process can be repeated as needed with subsequent forces until a desired location for an opening or hole is reached.

In additional aspects, a portion of the scutellum section of the monocot embryo can be cut to extract a sample portion of the scutellum section. Optionally, in one aspect, the scutellum tissue can be cut by a laser, such as, for example and without limitation, a cold cutting laser, a Q-switched $CO_2$ laser, a femtosecond laser, a picosecond laser, and a nanosecond laser as are known in the art. However, it is contemplated that any known means for scutellum removal can be used in conjunction with the systems and methods disclosed herein. For example, in other exemplary aspects, it is contemplated that the scutellum tissue can be cut using wire poke methods, core sample methods, cell sloughing methods, wire scrape methods, or combinations thereof.

In other aspects, the monocot embryo (e.g., corn embryo) can be genotyped. In another aspect, the monocot embryo can be selected or discarded on the basis of the genotyping. In another aspect, remaining portions of the selected monocot embryo can be germinated.

In further aspects, the sample portion of the scutellum section of the monocot embryo can be analyzed. In these aspects, the analysis can comprise at least one of genetic, chemical, and spectral analysis of the sample portion. In additional aspects, the method can further comprise selecting or discarding the remaining portions of the monocot embryo on the basis of the analysis (e.g., genetic analysis) of the sample portion of the scutellum section. When the monocot embryo is selected on the basis of the analysis (e.g., genetic analysis) of the sample portion of the scutellum section, it is contemplated that the method can further comprise germinating the remaining portions of the monocot embryo (including the meristematic section of the monocot embryo).

Following extraction of the monocot embryo from the monocot seed, the method can further comprise collecting the monocot embryo. It is contemplated that the monocot embryo can be collected by mechanical means. In exemplary aspects, the monocot embryo can be extracted such that the extracted monocot embryo is received within a liquid bath as disclosed herein. In these aspects, it is contemplated that the monocot embryo can be collected through a tube positioned in fluid communication with the liquid bath. In these aspects, it is contemplated that the tube can be configured to sequentially receive individual monocot embryos and transport the monocot embryos to at least one selected receptacle. Optionally, it is contemplated that each sequential monocot embryo can be transported to and received within its own respective receptacle. Alternatively, it is contemplated that a plurality of monocot embryos can be sequentially delivered into a single receptacle. In additional exemplary aspects, it is contemplated that the tube and the at least one selected receptacle can be operatively coupled to a positive pressure source or a negative pressure source, such as, for example and without limitation, a suction pump as is known in the art.

In exemplary aspects, the liquid bath can optionally be filled with at least one of water, solution, buffer, or liquid gel.

In further exemplary aspects, the monocot seed can optionally be an immature maize seed obtained between 8 and 20 days after pollination. In still further exemplary aspects, the monocot seed can optionally be an immature maize seed obtained between 9 and 18 days after pollination. In still further exemplary aspects, the monocot seed can optionally be an immature maize seed obtained between 10 and 15 days after pollination.

III. Methods of Auto Extracting Monocot Embryos from Immature Monocot Seeds

In various aspects, a method is provided for automatically extracting a monocot embryo from a monocot seed such that the monocot embryo is undamaged following extraction. The monocot seed can have a proximal end and an opposed distal end. Prior to removal of the monocot seed from a biological carrier, the proximal end of the monocot seed can be attached to the biological carrier and the distal end of the monocot seed can be spaced from the biological carrier. In various exemplary aspects, the monocot seed can be an immature monocot seed as disclosed herein.

Figure 23:
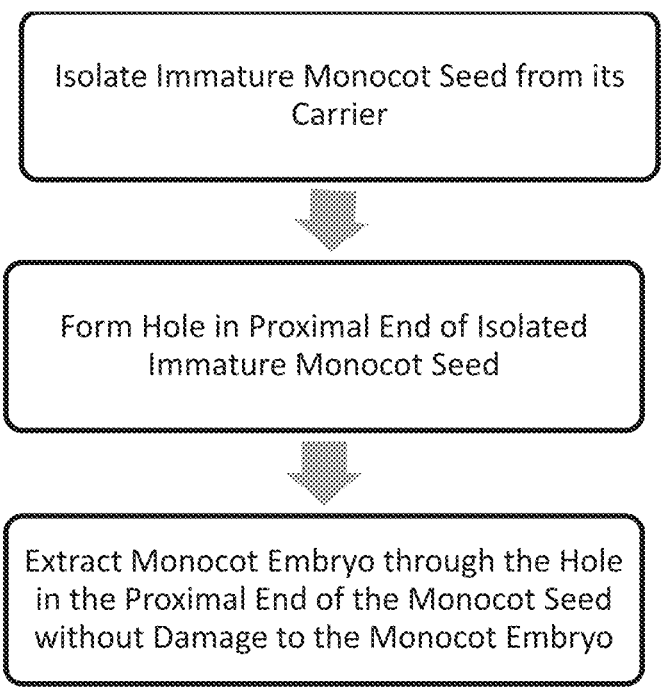
FIG. 23 is a flow chart depicting another exemplary method of extracting a monocot embryo from a monocot seed as disclosed herein.

In one aspect, and with reference to FIG. 23, the method can comprise providing an isolated monocot seed. Optionally, in an exemplary aspect, the monocot seed can have an opening or hole in the proximal end of the monocot seed. In this aspect, the isolated monocot seed can be provided following removal of the monocot seed from the biological carrier. In another aspect, when the proximal end of the monocot seed has an opening or hole as described herein, the method can comprise automatically extracting the monocot embryo through an opening or hole in the proximal end of the monocot seed. Optionally, it is contemplated that the monocot embryo of the monocot seed can be extracted such that the endosperm of the monocot seed is not extracted. When the monocot seed has an opening or hole as described herein, it is contemplated that the monocot embryo of the monocot seed can be extracted such that the endosperm of the monocot seed is not extracted through an opening or hole of the monocot seed. It is still further contemplated that the extracted monocot embryo of the monocot seed can be sufficiently separated from other materials following extraction such that sieving of the extracted monocot embryo is not required. In additional aspects, it is further contemplated that the step of providing the monocot seed can comprise automatically removing at least a portion of the proximal end of the monocot seed to form an opening or hole without damage to the monocot embryo. Optionally, in some aspects, it is contemplated that the monocot embryo can be extracted within a liquid bath as further disclosed herein. In these aspects, it is further contemplated that the extracted monocot embryo can be transported to a selected receptacle as further disclosed herein.

In exemplary aspects, it is contemplated that the monocot seed can be selected from the group consisting of a corn seed (kernel) and a sorghum seed. Optionally, the monocot seed can be selected from the group consisting of an immature corn kernel (e.g., an immature maize seed) and an immature sorghum seed.

In an additional aspect, it is contemplated that the step of automatically extracting the monocot embryo can comprise automatically applying pressure to at least one side portion of the monocot seed to force the monocot embryo through an opening or hole in the proximal end of the monocot seed. Alternatively, when an opening or hole is not formed in the monocot seed, it is contemplated that the step of automatically extracting the monocot embryo can comprise automatically applying pressure to at least one side portion of the monocot seed to split a portion of the proximal end of the monocot seed and to force the monocot embryo through an opening or hole defined by the split portion of the monocot seed. In a further aspect, it is contemplated that the method can further comprise forming an opening or hole in the proximal end of the monocot seed. In this aspect, it is contemplated that an opening or hole can optionally be made automatically in the proximal end of the monocot seed. As further described herein, it is contemplated that the step of forming an opening or hole within the proximal end of the monocot seed can be an iterative process. Optionally, in further exemplary aspects, force can be applied to the proximal end of the monocot seed at a location between the tip cap (most proximal tip) of the monocot seed and the monocot embryo within the seed to form an opening or hole. In these aspects, force can be applied to the proximal end of the monocot seed at a location spaced a selected distance from the tip cap to form an opening or hole. It is contemplated that the selected distance from the tip cap can optionally range from about 0.1 mm to about 3 mm. It is further contemplated that the selected distance from the tip cap can optionally range from about 0.25 mm to about 1.5 mm. In various exemplary aspects, it is contemplated that the method can further comprise using an imaging system to automatically image the monocot embryo to permit identification of the scutellum and meristematic sections of the extracted monocot embryo.

Optionally, in some aspects, the outer surface of the isolated monocot seed can be cleaned and/or sterilized before it is provided. Alternatively, in other optional aspects, it is contemplated that the method can further comprise cleaning at least the proximal end of the monocot seed prior to making the opening in the proximal end of the monocot seed and/or applying pressure to the at least one side portion of the monocot seed. It is further contemplated that the method can comprise sterilizing the monocot seed prior to forming an opening or hole in the proximal end of the monocot seed and/or applying pressure to the at least one side portion of the monocot seed. In exemplary aspects, the method can optionally comprise positioning the monocot seed in a selected orientation as further disclosed herein, such as, for example, prior to forming an opening or hole in the monocot seed and/or prior to extracting the monocot embryo. In these aspects, the step of positioning the monocot seed in a selected orientation can optionally comprise placing the monocot seed in a liquid bath as further disclosed herein.

Optionally, in another aspect, the extracted monocot embryo can be released from an opening or hole of the monocot seed into a liquid bath. In this aspect, the liquid bath can optionally be filled with at least one of water, solution, buffer, and liquid gel. Optionally, in some aspects, it is contemplated that the steps of forming an opening or hole in the monocot seed and/or extracting the monocot embryo from the monocot seed can occur with the monocot seed at least partially submerged within a liquid bath as further disclosed herein.

In other aspects, the monocot embryo (e.g., corn embryo) can be genotyped. In another aspect, the monocot embryo can be selected or discarded on the basis of the genotyping. In another aspect, remaining portions of the selected monocot embryo can be germinated.

In a further optional aspect, the method can further comprise automatically removing a sample portion of the scutellum tissue of the extracted monocot embryo without damage to the extracted monocot embryo. Optionally, it is further contemplated that the sample portion of the scutellum tissue can be removed by laser, such as, for example and without limitation, a cold cutting laser, a Q-switched $CO_2$ laser, a femtosecond laser, a picosecond laser, and a nanosecond laser as are known in the art. However, it is contemplated that any known means for scutellum removal can be used in conjunction with the systems and methods disclosed herein. For example, in other exemplary aspects, it is contemplated that the scutellum tissue can be cut using wire poke methods, core sample methods, cell sloughing methods, wire scrape methods, or combinations thereof.

In aspects, the sample portion of the scutellum tissue can be analyzed. In these aspects, the analysis can comprise at least one of genetic, chemical, and spectral analysis of the sample portion. In additional aspects, the method can further comprise selecting or discarding the meristematic tissue of the monocot embryo on the basis of the analysis (e.g., genetic analysis) of the sample portion of the scutellum tissue. When the meristematic tissue of the monocot embryo is selected on the basis of the molecular analysis (e.g., genetic analysis) of the sample portion of the scutellum tissue, it is contemplated that the method can further comprise germinating the remaining portion of the monocot embryo comprising the selected meristematic tissue.

In exemplary aspects, the monocot seed can optionally be an immature maize seed obtained between 8 and 20 days after pollination. An immature seed may be a monocot seed harvested after fertilization but prior to physiological maturity and, except in the case of hard coat seeds, does not germinate in water without external nutrients. For example, harvest may occur between 200 and 750 Growth Degree Units (GDUs) after pollination. In exemplary aspects, the monocot seed can optionally be an immature maize seed obtained between 9 and 18 days after pollination. In exemplary aspects, the monocot seed can optionally be an immature maize seed obtained between 10 and 15 days after pollination.

IV. Methods of Regenerating Plants from Immature Monocot Seeds

In various aspects, and with reference to FIG. 24A, a method of regenerating a plant from a monocot seed is provided. In these aspects, the method can comprise automatically extracting a monocot embryo from the monocot seed. Optionally, the monocot seed can be an immature monocot seed. As further disclosed herein, the monocot embryo comprises a meristematic section and a scutellum section. It is contemplated that the monocot embryo can optionally be extracted without damaging the monocot embryo. It is further contemplated that the monocot embryo of the monocot seed can be automatically extracted such that most of the endosperm of the monocot seed is not extracted. It is still further contemplated that the extracted monocot embryo of the monocot seed can be sufficiently separated from other materials following extraction such that sieving of the extracted monocot embryo is not required.

Optionally, in some aspects, it is contemplated that a method can comprise the step of forming an opening or hole in the monocot seed prior to extracting the monocot embryo, as further disclosed herein. As used herein, the terms "opening" and "hole" are used interchangeably and refer to any opening, hole, aperture, or tear through the seed pericarp that exposes a portion of the interior of the seed to the external environment, and may include making a weakened site, such as a scratched or etched site, on a seed, which when pressure is applied to the seed or is created in the interior of the seed, the weakened site splits to form a hole or opening. As further described herein, it is contemplated that the step of forming an opening or hole within the proximal end of the monocot seed can be an iterative process. Optionally, in exemplary aspects, force can be applied to the proximal end of the monocot seed at a location between the tip cap (most proximal tip) of the monocot seed and the monocot embryo within the seed to form the opening or hole. In these aspects, force can be applied to the proximal end of the monocot seed at a location spaced a selected distance from the tip cap to form the hole. It is contemplated that the selected distance from the tip cap can optionally range from about 0.1 mm to about 3 mm. It is contemplated that the selected distance from the tip cap can optionally range from about 0.25 mm to about 1.5 mm. In an aspect, it is contemplated that the monocot seed can have a proximal end and a distal end, with the proximal end being closer to the monocot embryo than the distal end. In an aspect, it is contemplated that an opening or hole in the proximal end of the monocot seed can be formed without damage to the monocot embryo. In exemplary aspects and as further disclosed herein, it is contemplated that an opening or hole in the proximal end of the immature monocot seed can be formed using conventional means, such as, for example and without limitation, a cutting blade, a laser, squeezing means, crushing means, ripping means, tearing means, and the like. In exemplary aspects, it is contemplated that the opening or hole can also be formed by the application of pressure to and/or within the seed as further described herein. For example, it is contemplated that the opening or hole can be formed at a weakened portion of the proximal end of the seed. In exemplary aspects, the weakened portion of the proximal end of the seed can be formed by weakening the outer surface of the seed, such as by scratching, etching or chemically degrading, a portion of the proximal end. After the weakened portion has been formed, it is contemplated that the opening or hole can be formed by pressure applied to the seed or a portion of the seed, or pinching, tearing, poking, scraping, and/or further chemically degrading the weakened portion of the proximal end of the seed.

In exemplary aspects, a method can optionally comprise positioning the monocot seed in a selected orientation as further disclosed herein, such as, for example, prior to forming the hole in the monocot seed and/or prior to extracting the monocot embryo. Optionally, in some aspects, the step of positioning the monocot seed in the selected orientation can comprise placing the monocot seed within a liquid bath as further disclosed herein. In these aspects, the liquid bath can optionally be filled with at least one of water, solution, buffer, and liquid gel. In these aspects, it is contemplated that the step of automatically extracting the monocot embryo from the monocot seed can optionally occur with the monocot seed at least partially submerged within a liquid bath as further disclosed herein.

In still further exemplary aspects, it is contemplated that at least a portion of the outer surface of the monocot seed can be cleaned and/or sterilized as further disclosed herein.

In additional aspects, it is contemplated that the extracted monocot embryo can be transported to a selected receptacle as further disclosed herein.

In another aspect, the method can comprise automatically removing a sample portion of the scutellum section of the monocot embryo without damage to the monocot embryo. In other exemplary aspects, it is further contemplated that the sample portion of the scutellum tissue can be removed by a laser, such as, for example and without limitation, a cold cutting laser, a Q-switched $CO_2$, laser, a femtosecond laser, a picosecond laser, and a nanosecond laser as are known in the art. However, it is contemplated that any known means for scutellum removal can be used in conjunction with the systems and methods disclosed herein. For example, in some aspects, it is contemplated that the sample portion of the scutellum tissue can be removed by poking, scraping, and/or sloughing as are known in the art. In various exemplary aspects, it is contemplated that the method can further comprise using an imaging system to automatically image the monocot embryo to permit identification of the scutellum and meristematic sections of the extracted monocot embryo.

In still another aspect, the method can comprise analyzing (e.g., genetically analyzing) the sample portion of the scutellum section of the monocot embryo. In this aspect, it is contemplated that the analysis of the sample portion can comprise at least one of genetic, chemical, and spectral analysis. In a further aspect, the method can comprise regenerating a plant from the remaining portions of the monocot embryo (including the meristematic section of the monocot embryo). In this aspect, it is contemplated that the monocot embryo can be undamaged following extraction.

In further aspects, it is contemplated that the step of automatically extracting the monocot embryo can comprise automatically applying force to extract the monocot embryo. In these aspects, it is further contemplated that the step of applying force to extract the monocot embryo can comprise applying pressure to at least one side portion of the monocot seed to force the monocot embryo through the hole in the proximal end of the monocot seed.

In aspects, the monocot seed can be an immature monocot seed including but not limited to, an immature corn kernel (e.g., an immature maize seed), an immature sorghum seed, an immature wheat seed or an immature rice seed.

In aspects, the monocot seed can optionally be an immature maize seed obtained between 8 and 20 days after pollination. In still further exemplary aspects, the monocot seed can optionally be an immature maize seed obtained between 9 and 18 days after pollination. In still further exemplary aspects, the monocot seed can optionally be an immature maize seed obtained between 10 and 15 days after pollination.

Figure 24B:
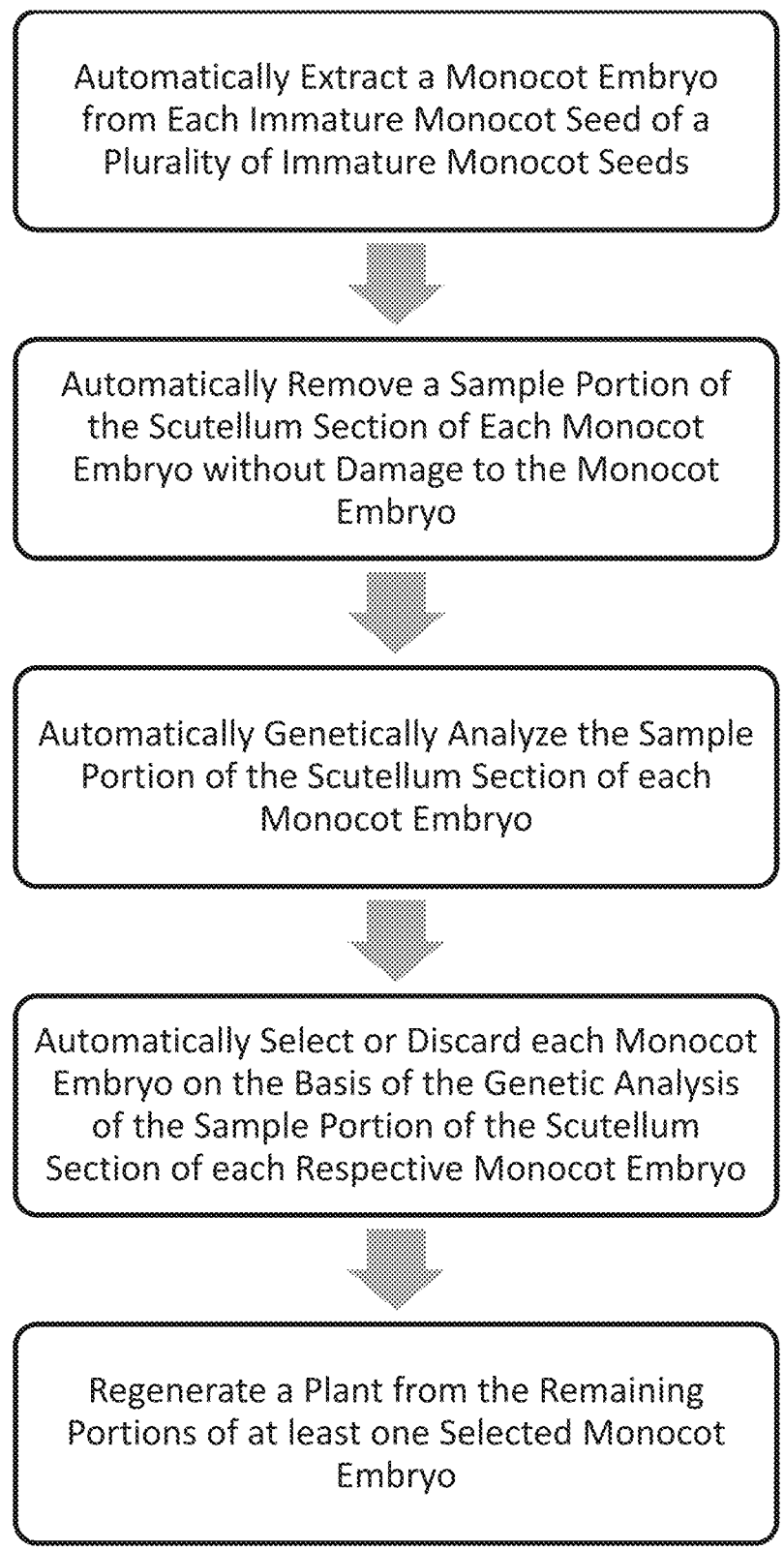
FIG. 24B is a flow chart depicting an exemplary method of regenerating a plant from portions of at least one monocot embryo selected among a plurality of monocot embryos following extraction of the monocot embryos from monocot seeds.

It is contemplated that a method of regenerating a plant from selected meristematic tissue of a monocot seed can be modified to permit analysis of a plurality of monocot seeds. In exemplary aspects, and as shown in FIG. 24B, such a method can comprise automatically extracting a monocot embryo from each respective monocot seed of a plurality of monocot seeds.

In some aspects, the extracted monocot embryo (e.g., corn embryo) can be genotyped. In another aspect, the monocot embryo can be selected or discarded on the basis of the genotyping. In another aspect, remaining portions of the selected monocot embryo can be germinated.

In further aspects, the method can further comprise automatically removing a sample portion of the scutellum section of the monocot embryo of each respective monocot seed without damage to the monocot embryo. Optionally, the monocot embryo of each respective monocot seed can be extracted such that the endosperm of the monocot seed is not extracted through the hole of the proximal end of the monocot seed. The method can further comprise automatically analyzing (e.g., genetically, chemically, and/or spectrally analyzing) the sample portion of the scutellum section of the monocot embryo of each respective monocot seed. The method can still further comprise automatically selecting or discarding the remaining portions of the monocot embryo of each respective monocot seed on the basis of the analysis of the sample portion of the scutellum section of the monocot embryo of each respective monocot seed. In exemplary aspects, the meristematic tissue of the monocot embryo of at least one monocot seed of the plurality of monocot seeds can be selected. In further aspects, the method can comprise regenerating a plant from the remaining portions of each respective monocot embryo (including the meristematic section).

Optionally, in exemplary aspects, it is contemplated that at least one of the following steps can be performed in an automatic manner: removing a sample portion of the scutellum section of the monocot embryo of each respective monocot seed; genetically analyzing the sample portion of the scutellum section of the monocot embryo of each respective monocot seed; selecting or discarding remaining portions of the monocot embryo of each respective monocot seed on the basis of the genetic analysis of the sample portion of the scutellum section of the monocot embryo of each respective monocot seed; and regenerating a plant from the remaining portions of the monocot embryo of each respective selected monocot seed.

V. Exemplary Uses of the Extracted Monocot Embryos

Figure 24C:
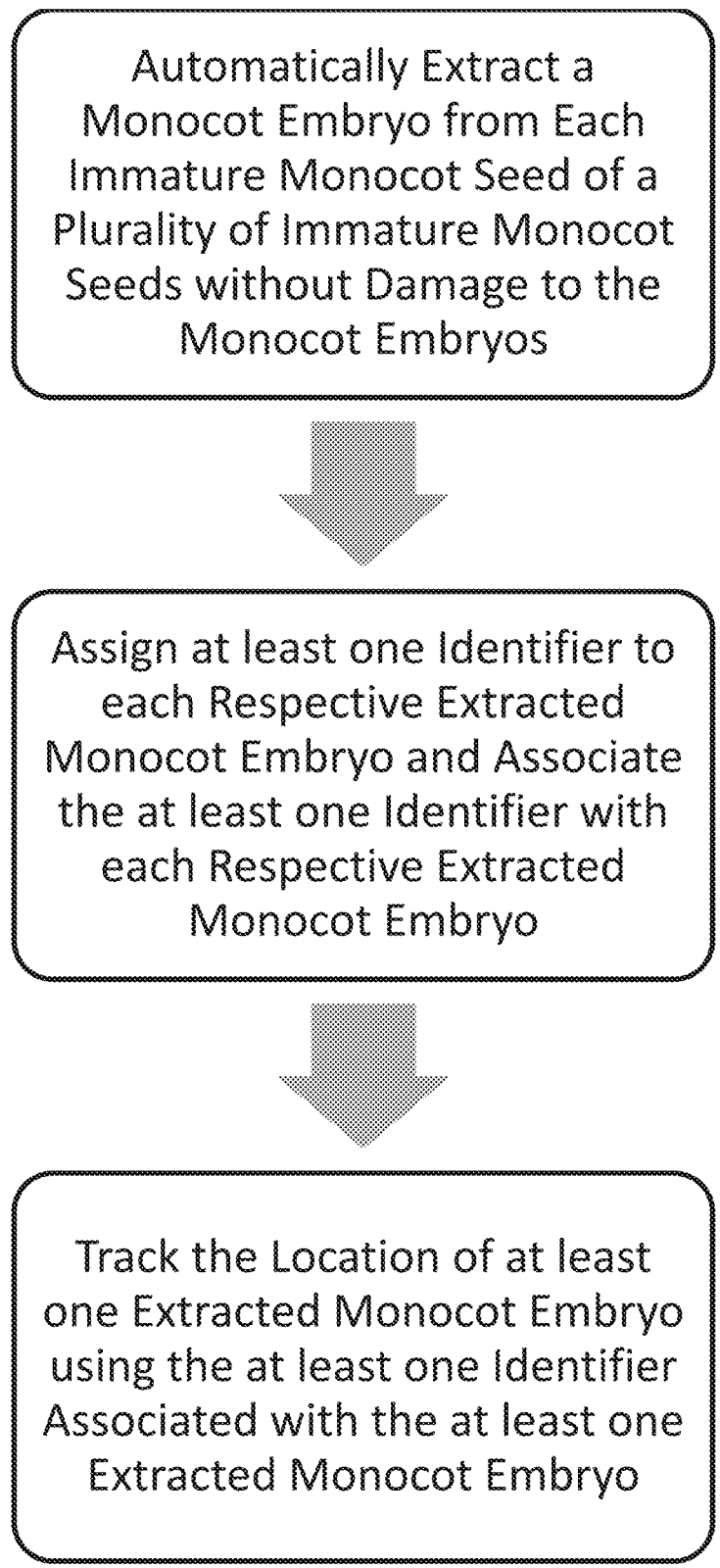
FIG. 24C is a flow chart depicting an exemplary method of tracking the location of at least one extracted monocot embryo during the method depicted in FIG. 24B. Tracking may comprise identifying and relating an embryo, a sample of a particular embryo or portion of a seed to the original seed. In general, the identity and relation of a seed to its geographic location of growth or genetic sources (parentage) are known or tracked.

In various aspects, and with reference to FIG. 24C, it is contemplated the the monocot embryo extraction methods and systems disclosed herein can permit one-to-one tracking of individual monocot embryos by a large-scale tracking system. In these aspects, it is contemplated that the receptacle containing each respective monocot embryo (or group of monocot embryos from a selected batch) can be assigned at least one unique identifier (e.g., a barcoded batch indentification number) that is entered into a database and tracked using conventional automated and/or computerized methods. It is further contemplated that each unique receptacle identifier can be linked with information about the one or more monocot embryos contained within the receptacle, such as, for example and without limitation, the variety of the monocot seed, the specific location (within the field) of the plant from which the monocot embryo was obtained, the location of the monocot seed on its biological carrier (e.g., the location of a corn kernel on an ear), and the like. Thus, it is contemplated that each receptacle can be assigned at least one unique identifier that is read and entered into a database of the tracking system. Similarly, it is contemplated that a given batch of monocot embryos can be assigned a unique batch identifier that can be scanned by the tracking system before the extraction process begins. When one or more monocot embryos from a given batch are received within the receptacle, the database entry associated with the receptacle can be updated automatically to associate the receptacle with the batch identifier. Tracking may also comprise creating and using the same or a different unique identifier to associate the embryo of a seed with other portions of the embryo or seed, such as associating the embryo with a sample of that embryo or a sample of the seed from which the embryo was extracted, for example, the endosperm.

Some exemplary applications for the extracted monocot embryos are disclosed below.

a. Plant Breeding

In exemplary aspects, it is contemplated that a monocot embryo extracted as disclosed herein can be used in plant breeding as is known in the art. Generally, in aspects, it is contemplated that a plant can be regenerated from an undamaged monocot embryo extracted as disclosed herein. It is further contemplated that the regeneration of a plant using an extracted monocot embryo can be accomplished using conventional plant breeding methods.

In aspects, it is contemplated that a monocot embryo extracted as disclosed herein can be used for plant breeding purposes as are known in the art, for example for embryos comprising particular traits or genes, whether wild-type or transgenic. In aspects, one or more extracted monocot embryos can be placed in a growth medium with one or more selective agent to assess the resistance of the monocot embryos to one or more selective agents. It is contemplated that monocot embryos with resistance to one or more selective agents will grow while the monocot embryos with insufficient resistance to one or more selective agents will die.

In aspects, it is contemplated that a sample of the scutellum section of an extracted monocot embryo can be obtained before placement of the monocot embryo in a selective or growth medium. In aspects, it is contemplated that a variety of techniques can be used to remove the sample portion of the scutellum section of the monocot embryo. In exemplary aspects, it is contemplated that the process of removing the sample portion of the scutellum section can comprise identifying the orientation and location of an extracted monocot embryo by automated detection means, such as, for example and without limitation, machine vision, imaging systems, and sensing means as are known in the art. The process of removing the sample can further comprise picking up the monocot embryo using automated means (e.g., robotic means). The monocot embryo can then be aligned with a cutting device, such as, for example and without limitation, a tissue-cutting laser. The cutting device can be applied to the scutellum section of the monocot embryo to retrieve the sample in a manner that preserves the viability and vigor of the monocot embryo as disclosed herein. The sample can then be received within a selected receptacle, such as, for example and without limitation, a bullet tube, a field plate, and the like. Following removal of the sample, the process can further comprise positioning the monocot embryo onto a growth medium, such as, for example and without limitation, a Phyta-tray or other container as is known in the art. Following positioning of the monocot embryo into or onto the selective or growth medium, it is contemplated that the resulting cultured tissue can be used in plant breeding applications as are known in the art.

In exemplary aspects, it is contemplated that a monocot embryo extracted as disclosed herein can be used in a doubled haploid process as is known in the art. In these aspects, it is contemplated that the double haploid process can optionally be used in conjunction with plant breeding process as are known in the art. In some aspects, one or more extracted monocot embryos can be placed in a media containing an antimitotic or chromosome doubling agent (e.g., colchicine, oryzalin, or trifluralin) as is known in the art. In these aspects, it is contemplated that the placement of the extracted monocot embryo in the doubling media can cause the doubling of the chromosomes of each monocot embryo. It is further contemplated that the extracted monocot embryos could be selected based upon characteristics, e.g. characteristics revealed through chemical and/or spectral analysis. In additional aspects, after identification of the doubled haploids, the doubled haploids can be placed onto a growth medium, and germination can begin. Optionally, it is contemplated that a sample of the scutellum section of an extracted monocot embryo can be obtained before placement of the monocot embryo in the growth medium.

Exemplary Systems for Extracting and/or Isolating Monocot Embryos

Various systems are contemplated for performing one or more of the method steps disclosed herein. Although many of the systems and assemblies disclosed herein are described with reference to corn kernels, it is contemplated that the systems and assemblies can also be used to process and extract embryos from other monocot seeds, such as those disclosed herein. Similarly, it is contemplated that the systems and assemblies disclosed herein as being used to process and extract embryos from immature monocot seeds (e.g., immature corn kernels) may also be used to process and extract embryos from more mature monocot seeds.

The systems and assemblies disclosed herein are described as having various actuators that effect movement of components of the systems and assemblies in a desired manner. In exemplary aspects, it is contemplated that the actuators of the disclosed systems and assemblies can be positioned in operative communication with a processor, such as, for example and without limitation, a programmable logic controller (PLC) or a processor of a computer as is known in the art. In these aspects, it is contemplated that the processor can be configured to activate the actuators of the disclosed systems and assemblies in an automated manner.

a. Intact Seed Removal Systems and Methods

When the monocot seed is a corn (e.g., maize) kernel (e.g., an immature corn kernel), it is contemplated that the corn kernel can be provided for use in the disclosed methods following removal of the corn kernel from its cob. In aspects, it is contemplated that the corn kernels can be manually removed without rupturing of the kernels. In other exemplary aspects, it is contemplated that the corn kernels can be removed by an apparatus configured to cut sufficiently close to the cob to avoid damage to the embryos of the corn kernels. In further exemplary aspects, it is contemplated that the corn kernels can be removed by an apparatus that is configured to remove the corn kernels from a cob while leaving the corn kernels substantially intact.

i. Ear Preparation

In exemplary aspects, it is contemplated that ears of corn can be harvested from the field using conventional methods. Optionally, the ears can be manually harvested from the field. Optionally, following harvesting, the ears can then be placed in mesh bags inside a refrigerated chamber for approximately two (2) days. Following refrigeration, the ears can optionally be husked. It is contemplated that the ears can be husked manually. After the ears are husked, the ears can optionally be cleaned with a selected cleaning solution, such as, for example and without limitation, a mixture of water, 10% bleach, and a few drops of Tween™ 20 (Polysorbate 20).

ii. Support and Cutting Systems and Methods

In exemplary aspects, methods for removing corn kernels from a cob are provided. In these aspects, cutting assemblies can be provided for removing the corn kernels while leaving the kernels substantially intact. During cutting of the corn kernels, the ear of corn can be externally supported or supported within the cob of the ear.

1. Cutting Systems and Methods with External Cob Support

Figure 11A:
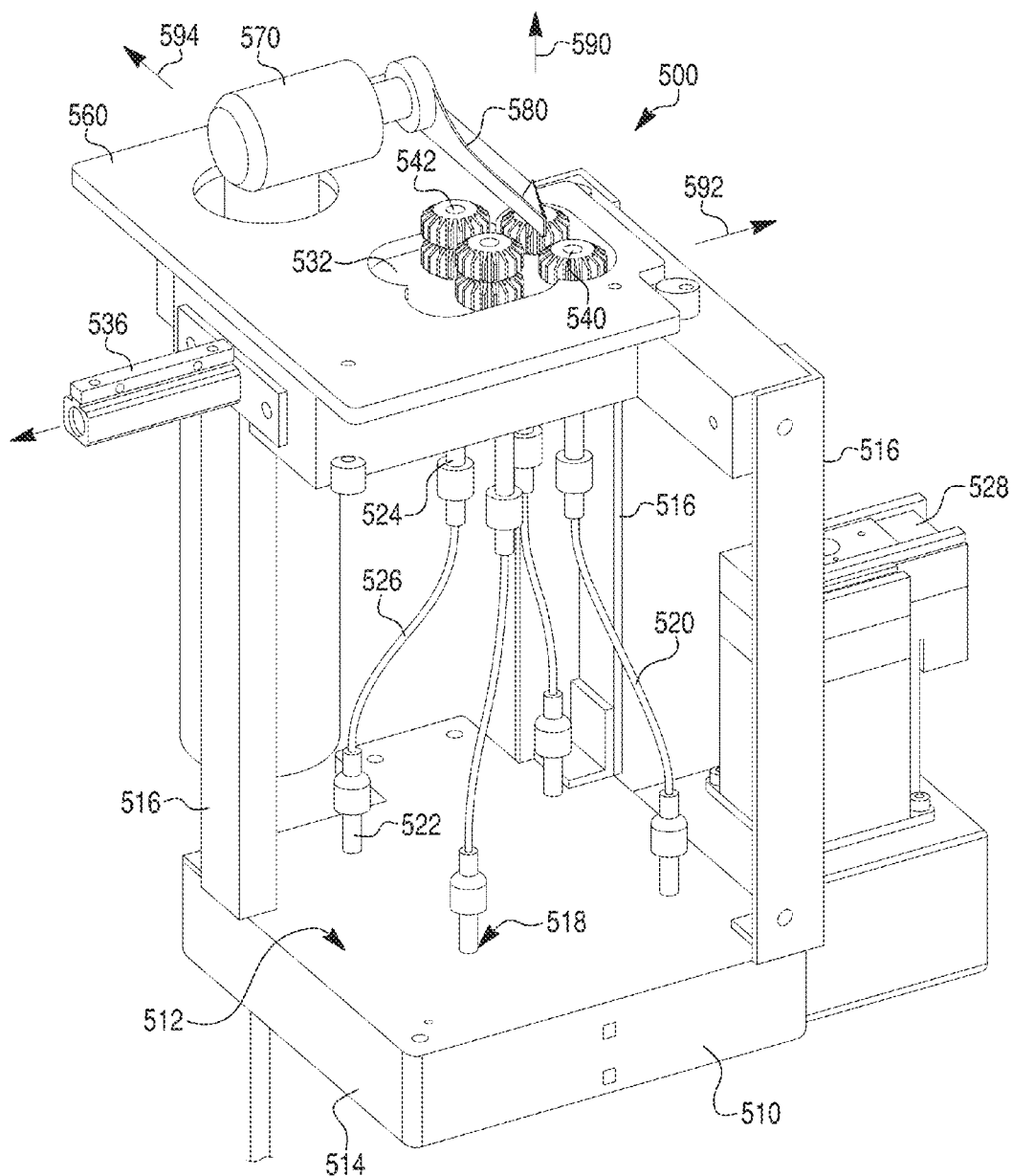
FIG. 11A is a perspective view of an exemplary external cutting assembly of a seed removal system as disclosed herein. As shown, the external cutting assembly has a plurality of feed wheels.
Figure 11B:
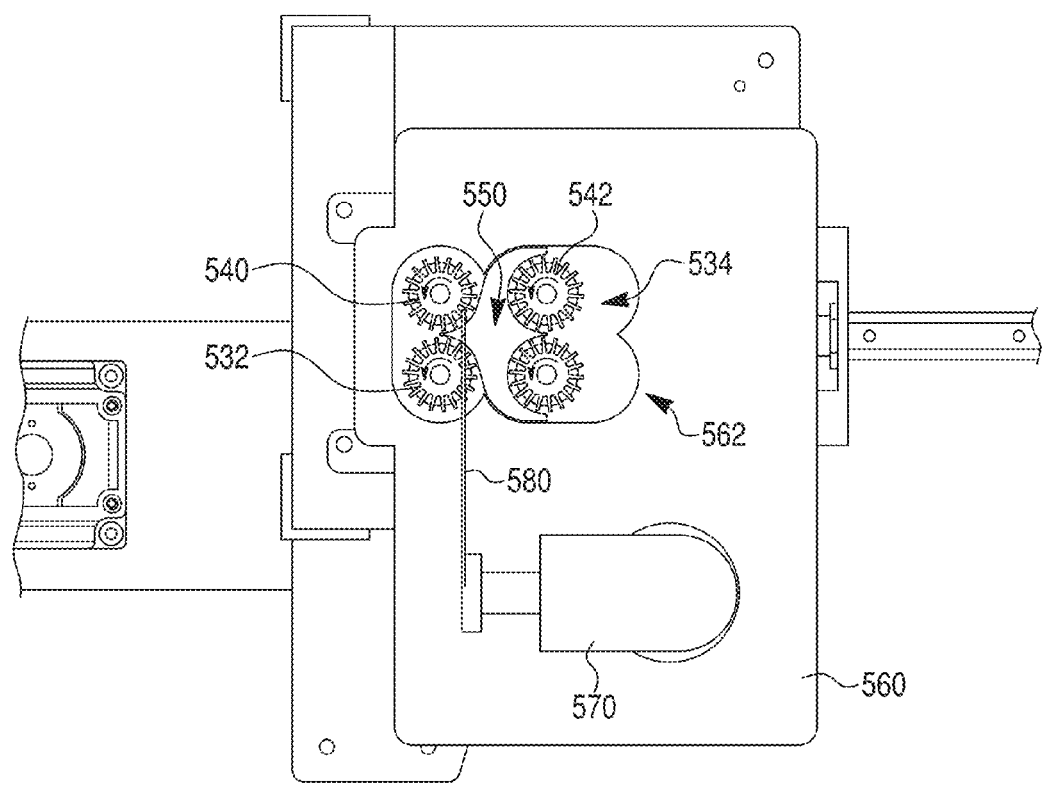
FIG. 11B is a top view of the cutting assembly of FIG. 11A.
Figure 11C:
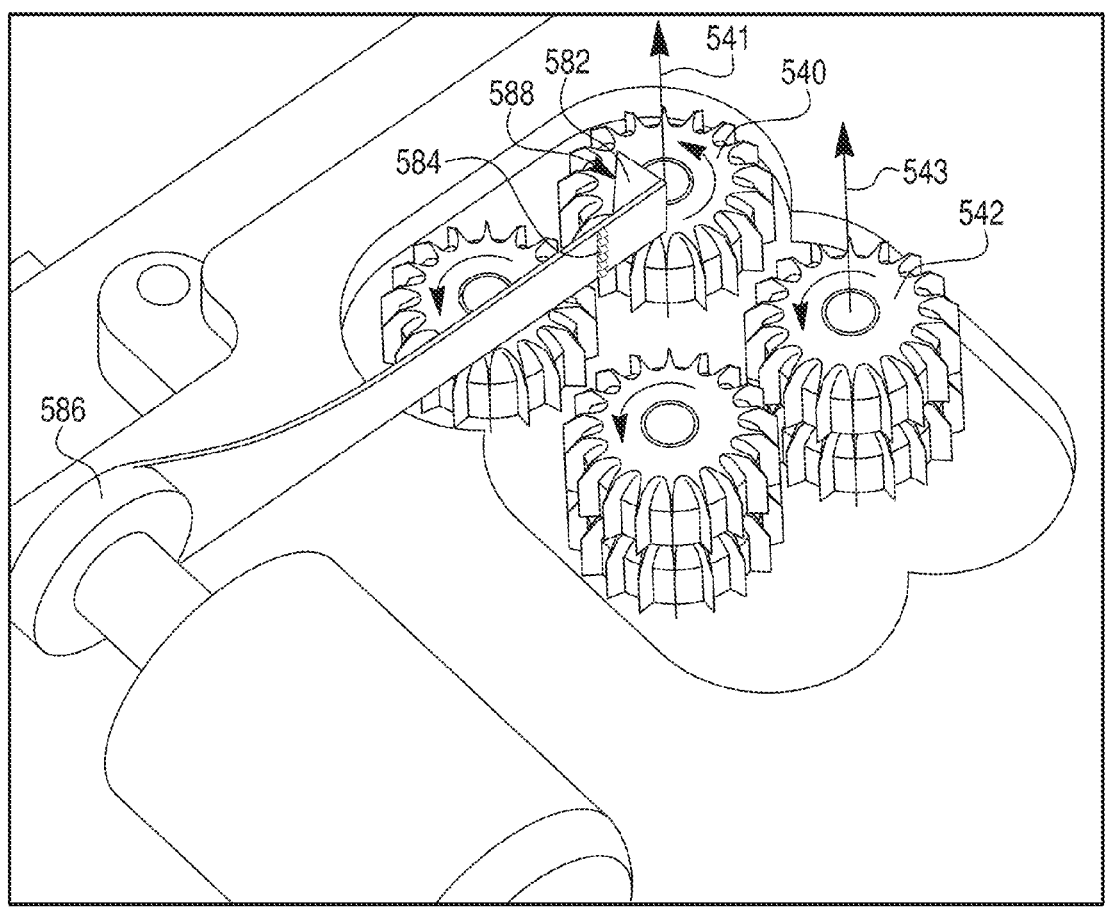
FIG. 11C is a close-up perspective view of a cutting arm and a plurality of feed wheels of the cutting assembly of FIG. 11A.

In one aspect, and with reference to FIGS. 11A-11C, disclosed is a system 500 for removing corn kernels from a cob while externally supporting the cob.

In another aspect, the system 500 can comprise a base portion 510 having an upper surface 512 and an interior space 514. In this aspect, the upper surface 512 can define a plurality of bores 518 that extend from the upper surface to the interior space 514 of the base portion 510.

In an additional aspect, the system 500 can comprise a feed block assembly 532 axially spaced from the base portion 510 relative to a vertical axis 590. In this aspect, the feed block assembly 532 can define an opening 550 configured to receive an ear of corn positioned substantially parallel to the vertical axis 590. In exemplary aspects, the feed block assembly 532 can be supported by at least one support 516 that extends upwardly from the base portion 510 relative to the vertical axis 590.

In a further aspect, the system 500 can comprise a plurality of feed wheels. In this aspect, it is contemplated that the plurality of feed wheels can comprise at least one feed wheel 540 positioned on a first side of the opening 550 of the feed block assembly and at least one feed wheel 542 positioned on a second side of the opening of the feed block assembly. It is further contemplated that the feed wheels 540 positioned on the first side of the opening 550 can be spaced apart from the feed wheels 542 positioned on the second side of the opening relative to a first axis 592 that is substantially perpendicular to the vertical axis 590. Optionally, in exemplary aspects, the at least one feed wheel 540 positioned on the first side of the opening 550 can comprise at least two feed wheels that are spaced apart relative to a second axis 594 that is substantially perpendicular to the vertical axis 590 and the first axis 592. Optionally, in other exemplary aspects, the at least one feed wheel 542 positioned on the second side of the opening 550 can comprise at least two feed wheels that are spaced apart relative to the second axis 594.

In exemplary aspects, each feed wheel 540 can be configured for rotation relative to a respective rotational axis 541. Optionally, in these aspects, the rotational axes 541 of the feed wheels 540 can be angled inwardly toward opening 550 at a selected acute angle relative to the vertical axis 590. In further exemplary aspects, each feed wheel 542 can be configured for rotation relative to a respective rotational axis 543. Optionally, in these aspects, the rotational axes 543 of the feed wheels 542 can be angled inwardly toward opening 550 at a selected acute angle relative to the vertical axis 590. Thus, it is contemplated that the feed wheels 540, 542 can be angled inwardly toward each other. In exemplary aspects, the selected acute angle can range from about 1 degree to about 5 degrees and, more preferably, can be about 3 degrees.

In an additional aspect, the system 500 can comprise a cutting arm 580 having a proximal portion 586 and a distal portion 588. In this aspect, the distal portion 588 can define a cutting element 582 and a grinding element 584. In another aspect, the cutting arm 580 can extend substantially parallel to the second axis 594, and the distal portion 588 of the cutting arm can be positioned over the opening 550 of the feed block assembly relative to the vertical axis 590. In exemplary aspects, the cutting element 582 can be offset from the grinding element 584. For example, in these aspects, the cutting element 582 can be offset from the grinding element 584 by a distance ranging from about 0.5 mm to about 2.0 mm relative to the first axis 592. In further exemplary aspects, the cutting element 582 can project upwardly from the distal portion 588 of the cutting arm 580 (and from the grinding element 584) relative to the vertical axis 590, thereby providing a hook-style arrangement that imparts stability to the system 500. Optionally, the cutting element 582 can be generally oriented in an upward direction that is angularly offset from the orientation of the grinding element 584. In operation, the cutting element 582 can be configured to undercut kernels that are rotating about the vertical axis 590, while the grinding element 584 can be configured to grind down the denser woody ring of the cob. In exemplary aspects, the cutting element 582 can be shaped such that, during rotation of the ear about the vertical axis 590, the kernels approach the cutting element moving from the proximal portion 586 of the cutting arm 580 moving toward the distal portion 588 of the cutting arm.

In another aspect, the system 500 can comprise an oscillation assembly 570 that is operatively coupled to the proximal portion 586 of the cutting arm 580 and configured to effect oscillating movement of at least the distal portion 588 of the cutting arm relative to the vertical axis 590. In exemplary aspects, the oscillation assembly 570 can comprise a conventional actuator, such as, for example and without limitation, a motor.

In a further aspect, the system 500 can comprise a plurality of shafts 520. In this aspect, each shaft 520 can have a proximal portion 522 positioned within a corresponding bore 518 of the upper surface 512 of the base portion 510 and a distal portion 524 operatively coupled to at least one feed wheel 540, 542 of the plurality of feed wheels.

In yet another aspect, the system 500 can comprise at least one motor 528 operatively coupled to the proximal portions 522 of the plurality of shafts. In this aspect, the at least one motor 528 can be configured to effect selective rotational movement of the plurality of shafts and the plurality of feed wheels. Thus, it is contemplated that the at least one motor 528 can be configured to effect selective rotational movement of the plurality of feed wheels relative to their respective rotational axes.

Optionally, in one exemplary aspect, the feed block assembly 530 can comprise a fixed portion 532 and a moveable portion 534 that cooperate to define the opening 550 of the feed block assembly. In this aspect, the at least one feed wheel 540 positioned on the first side of the opening 550 can be coupled to the fixed portion 532, and the at least one feed wheel 542 positioned on the second side of the opening 550 can be coupled to the moveable portion 534. In another aspect, the moveable portion 534 can be selectively axially moveable relative to the first axis 592 to selectively adjust a diameter of the opening 550 of the feed block assembly. In exemplary aspects, the system 500 can comprise at least one actuator 536 that is operatively coupled to the moveable portion 534 and configured to effect selective axial movement of the moveable portion. In one exemplary aspect, the at least one feed wheel 540 positioned on the first side of the opening 550 and coupled to the fixed portion 532 can comprise at least two fixed feed wheels, and the at least one feed wheel 542 positioned on the second side of the opening 550 and coupled to the moveable portion 534 can comprise a single feed wheel.

Optionally, in a further exemplary aspect, it is contemplated that at least a portion of at least one shaft 520 of the plurality of shafts can be flexible. For example, in one optional aspect, at least a portion of the shafts 520 that are operatively coupled to the feed wheels 542 positioned on the second side of the opening 550 of the feed block assembly can be flexible. In exemplary aspects, the proximal and distal portions 522, 524 of each shaft 520 can be substantially rigid, and an intermediate flexible portion 526 can extend between the proximal and distal portions of the shaft. In use, it is contemplated that the flexible portions of the shafts 520 can accommodate movement of the moveable portion 534 of the feed block assembly and the angular orientation of the feed wheels as disclosed herein.

In a further optional aspect, it is contemplated that at least the feed wheels 542 positioned on the second side of the opening 550 can comprise a plurality of stacked wheel assemblies, with each wheel assembly having two feed wheels positioned in alignment relative to their rotational axes. In one exemplary aspect, the at least one feed wheel 540 positioned on the first side of the opening 550 and coupled to the fixed portion 532 can comprise at least two fixed feed wheels, and the at least one feed wheel 542 positioned on the second side of the opening 550 and coupled to the moveable portion 534 can comprise at least two stacked wheel assemblies.

In exemplary aspects, the system 500 can further comprise a cover plate 560 that is positioned above a top surface of the feed block assembly 530 relative to the vertical axis. In these aspects, it is contemplated that the cover plate 560 can define an opening 562 that receives at least a top portion of the feed wheels 542 positioned on the second side of the opening 550. It is further contemplated that, as the moveable portion 534 of the feed block assembly is moved to expand the size of the opening 550, surfaces of the cover plate 560 that define opening 562 can be configured to contact the feed wheels 542 and restrict further movement of the moveable portion 534. Thus, it is contemplated that the cover plate 560 can be selectively positioned relative to the feed block assembly 530 to effectively set a maximum diameter of the opening 550.

In one aspect, it is contemplated that an ear of corn can be placed, distal end first, into the opening defined by the feed block assembly. It is further contemplated that the feed block assembly can be configured to close (via selective movement of the moveable portion 534) to maintain substantially constant force against the ear of corn. With the ear of corn maintained in the opening, the cutting arm can begin to oscillate relative to the vertical axis, and the feed wheels can begin to rotate about their rotational axes. In this aspect, the grinding element can grind away cob material until it encounters denser cob material. The cob can then be rotated and pulled through the feed block by the feed wheels as the feed wheels rotate. With the grinding element maintaining a position against the woody ring of the ear, the cutting element is able to undercut the kernels at a position immediate proximal to the cob from the kernels.

In use, it is contemplated that the cutting and grinding elements can continue to remove corn kernels based on the depth of the woody ring of the ear of corn. After the corn kernels have been removed, it is contemplated that the removed corn kernels can be collected by positive or negative air pressure, gravity, or other conventional means. The cob can then be disposed of after all the corn kernels have been removed.

2. Cutting Systems and Methods with Internal Cob Support

In exemplary aspects, and with reference to FIGS. 3A-10D, disclosed herein is a system 100 for removing immature corn kernels from a cob. In these aspects, the system 100 can have a longitudinal axis 102 and a transverse axis 105.

In one aspect, the system 100 can comprise at least one clamp assembly 110a, 110b. In this aspect, each clamp assembly 110a, 110b, can comprise opposed first and second engagement elements 112a, 112b that are spaced apart relative to a translation axis 113. The first and second engagement elements 112a, 112b of the at least one clamp assembly 110a, 110b can cooperate to define a receiving space 114 configured to receive an ear of corn. In exemplary aspects, at least one of the first or second engagement elements 112a, 112b can be configured for selective axial movement relative to the translation axis 113. In these aspects, it is contemplated that the at least one clamp assembly 110a, 110b can be configured to securely engage an ear of corn within the receiving space 114 in a desired orientation that is substantially perpendicular to the translation axis 113.

In an additional aspect, the system 100 can further comprise a drilling assembly 116, a stalk removal tool 117, and a drill actuator 118. The drill actuator 118 can be operatively coupled to the drilling assembly 116, and the drilling assembly can be operatively coupled to the stalk removal tool 117. In this aspect, the drill actuator 118 is configured to advance drilling assembly 116 to thereby advance the stalk removal tool 117 to remove hard stalk material 45 from the proximal end of the ear in order to provide access to the softer pith 42 of the ear.

In exemplary aspects, the at least one clamp assembly 110a, 110b can be configured for movement between a first operative position (shown in FIGS. 3A-3B) and a second operative position. In the first operative position, the at least one clamp assembly 110a, 110b can be configured to support an ear of corn as the drilling assembly 116 is activated to remove stalk material and provide access to the pith 42 of the ear. After the drilling assembly has completed its removal of the stalk material, the drilling assembly 116 can be withdrawn from the ear, and the at least one clamp assembly 110a, 110b can be moved to the second operative position while maintaining its engagement of the ear. It is contemplated that the movement of the at least one clamp assembly 110a, 110b can occur manually or by using automated means, such as, for example and without limitation, an actuator. Optionally, the movement of the at least one clamp assembly 110a, 110b between the first and second operative positions can be rotational movement. Thus, in some aspects, a rotational actuator can be coupled to the at least one clamp assembly to effect movement of the clamp assemblies between the first and second operative positions. In the second operative position, the at least one clamp assembly 110a, 110b can be configured to position the ear in substantial alignment with an orientation axis along which a spindle 115 can be axially advanced, as further disclosed herein. After the spindle 115 is sufficiently inserted into the ear, the at least one clamp assembly 110a, 110b can be configured to release its engagement of the ear and then return to the first operative position.

Figure 5A:
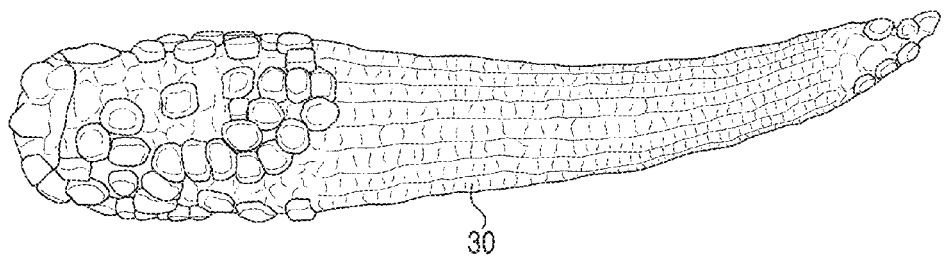
FIG. 5A is a top perspective view of an ear of corn having a curved profile.
Figure 5B:
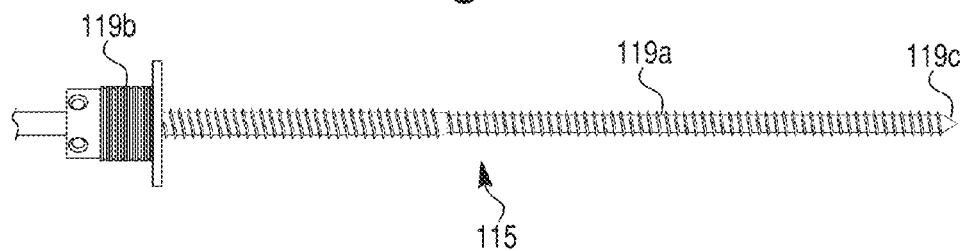
FIG. 5B is a top perspective view of an exemplary spindle as disclosed herein.
Figure 5C:
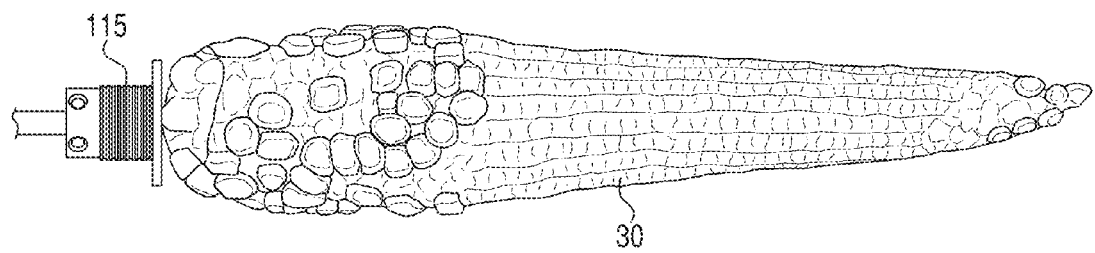
FIG. 5C is a top perspective view of the ear of corn of FIG. 5A, following insertion of the spindle within the ear and straightening of the ear.
Figure 6:
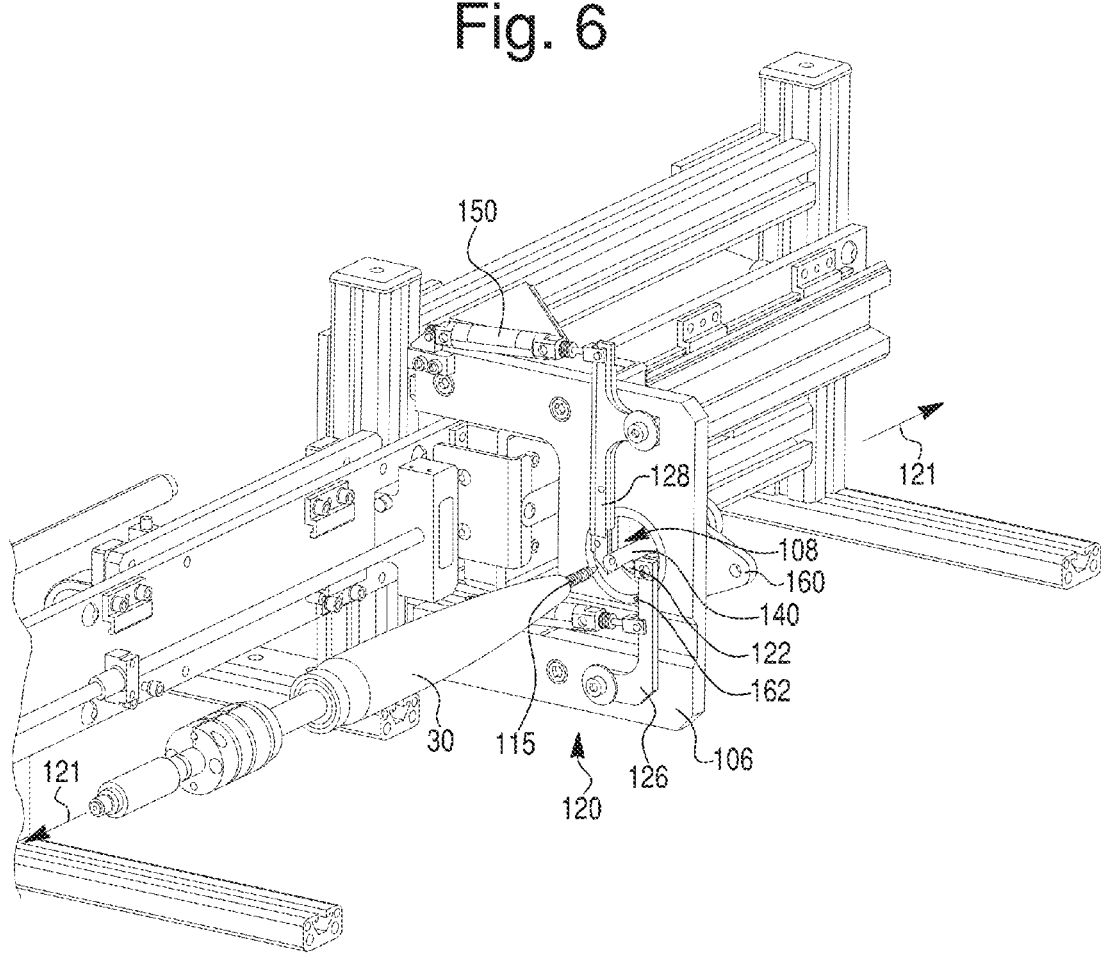
FIG. 6 is an isolated perspective view of an independent arm cutting assembly of an exemplary seed removal system as disclosed herein.
Figure 7:
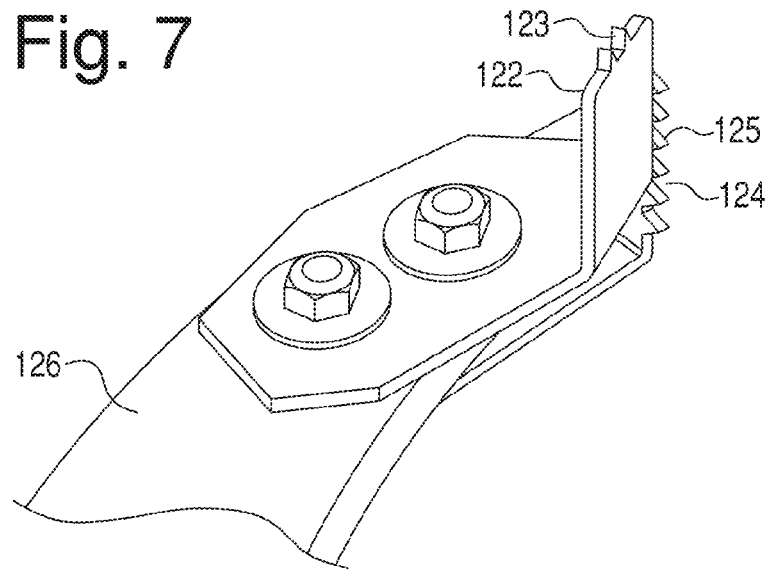
FIG. 7 is a close-up perspective view of an exemplary arm of the cutting assembly of a seed removal system as disclosed herein.

In further exemplary aspects, a spindle assembly having a spindle 115 can be provided. Optionally, in these aspects, and as shown in FIGS. 5A-5C, the spindle 115 can have a proximal base portion 119b and a threaded portion 119a extending from the base portion, with the threaded portion 119a defining a distal end 119c of the spindle. The spindle assembly can further comprise a spindle actuator 130 that is configured to operatively engage to the proximal base portion 119b of the spindle 115 and configured to rotate the spindle. The spindle actuator 130 can be operatively coupled to the proximal base portion 119b using any conventional means, including, for example and without limitation, a mechanical arm. Optionally, the spindle actuator 130 can be configured to rotate the spindle 115 at a pitch substantially equal to the pitch of the threaded portion 119a of the spindle. In one aspect, the spindle assembly can be operatively coupled to a linear actuator 190 that is configured to effect axial movement of the spindle assembly (and spindle 115). In this aspect, the linear actuator 190 can be configured to axially advance the spindle 115 into a cob portion of an ear of corn positioned in the desired orientation. In this aspect, the spindle 115 can be advanced relative to an axis (not shown) that is substantially perpendicular to the translation axis 113 of the at least one clamp assembly 110a, 110b (and substantially parallel to the longitudinal axis of the system 100). Thus, in combination, the spindle actuator 130 and the linear actuator 190 can be configured to effect linear and rotational motion of the spindle 115. In a further aspect, the at least one clamp assembly 110a, 110b can be configured to disengage the ear of corn following positioning of the spindle 115 within the cob portion of the ear. As shown in FIGS. 5A and 5C, the insertion of a spindle 115 as disclosed herein can straighten the ear, thereby reducing the variations in the shape and profile of the ear relative to the longitudinal axis 102 of the system 100.

Thus, in use, and with reference to FIG. 13A, the disclosed system 100 can be used in a method for obtaining an isolated corn kernel. In one aspect, the method can comprise positioning an ear of immature corn within the receiving space defined between the opposed engagement elements of the at least one clamp assembly. In this aspect, the ear can be removed from a stalk and having a proximal end, a distal end, a cob having a pith, and at least one immature corn kernel attached to the cob, wherein, prior to removal of the ear from the stalk, the proximal end of the ear is attached to the stalk. In another aspect, the method can comprise selectively adjusting a position of the opposed engagements elements relative to the translation axis to securely engage the ear in an orientation that is substantially perpendicular to the translation axis. Optionally, with the engagement elements maintaining their engagement of the ear, the method can comprise positioning the ear in alignment with a spindle assembly as disclosed herein. In a further aspect, the method can comprise inserting the threaded portion of the spindle through at least a portion of the pith of the cob of the ear. In this aspect, the spindle can extend substantially perpendicularly to the translation axis, and the spindle can have a base portion that abuts a proximal end of the ear. In exemplary aspects, the insertion of the threaded portion of the spindle through at least a portion of the pith of the cob of the ear can straighten the ear as further disclosed herein.

In a further aspect, the system 100 can comprise a cutting assembly 120, 170 that is configured to remove corn kernels from the cob portion of the ear.

One exemplary independent-arm cutting assembly 120 is depicted in FIGS. 3A-3B and 6-9B. In one aspect, the cutting assembly 120 can comprise at least one cutting arm 126 having a cutting portion 122. In one aspect, the linear actuator 190 can be configured to effect selective axial movement of the spindle assembly (and the spindle 115) relative to an orientation axis 121, and the spindle actuator 130 can be configured to effect selective rotation of the spindle 115 relative to the orientation axis. In exemplary aspects, the at least one cutting arm 126 can be operatively positioned relative to the spindle actuator 130 relative to the orientation axis 121. In further exemplary aspects, the at least one cutting arm 126 can be biased for pivotal movement to move the cutting portion 122 of each respective cutting arm relative to a desired arcuate profile that intersects the orientation axis 121. In use, it is contemplated that the cutting portions 122 of the at least one cutting arm 126 can be configured to remove intact corn kernels from the cob of an ear positioned on the spindle 115.

Although the spindle 115 is described above as being operatively coupled to separate linear and rotational actuators, it is contemplated that the spindle can alternatively be operatively coupled to a single actuator that is capable of effecting both linear and rotational movement of the spindle.

Figure 8:
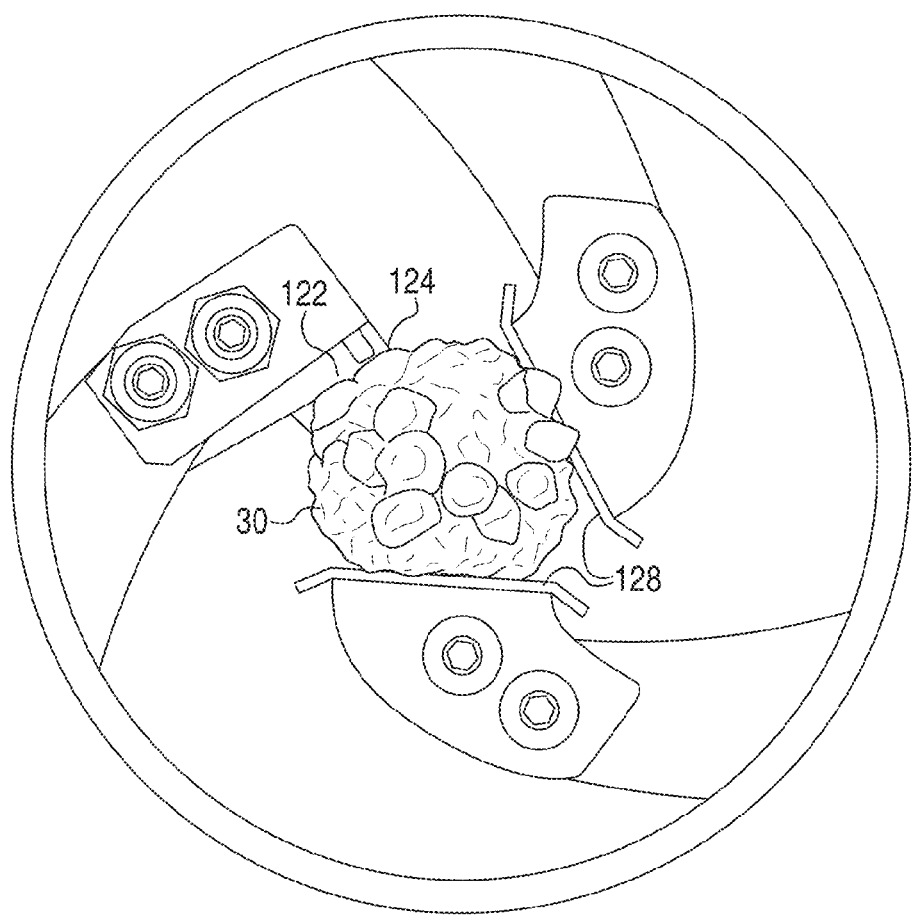
FIG. 8 is a side perspective view of an exemplary cutting assembly of a seed removal system as disclosed herein. As shown, the cutting assembly has a plurality of arms that can support an ear of corn during a cutting operation.

Optionally, in exemplary aspects, the at least one cutting arm 126 can comprise a plurality of cutting arms, as shown in FIG. 8. In this aspect, the plurality of cutting arms 126 can optionally comprise three cutting arms. However, it is contemplated that any desired number of cutting arms can be used.

Figure 9A:
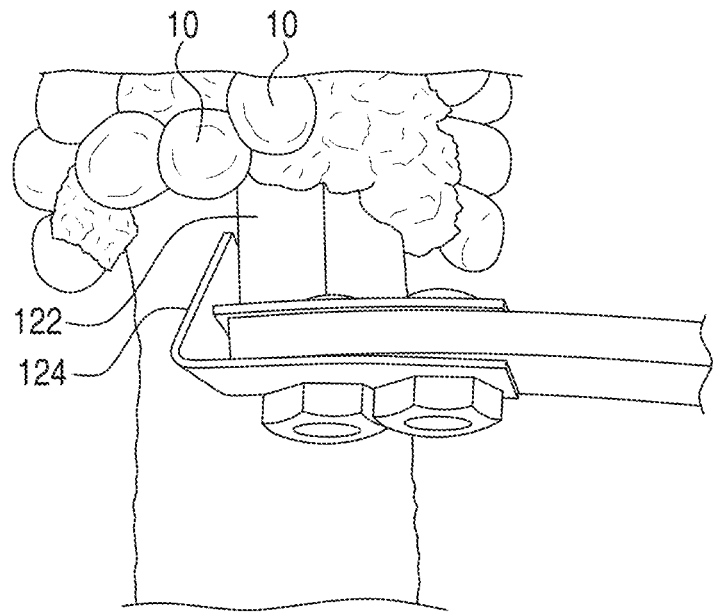
FIG. 9A is a top perspective view of an arm of an exemplary cutting assembly of a seed removal system as disclosed herein, showing the cutting and grinding portions of the arm engaging the kernels of an ear of corn.
Figure 9B:
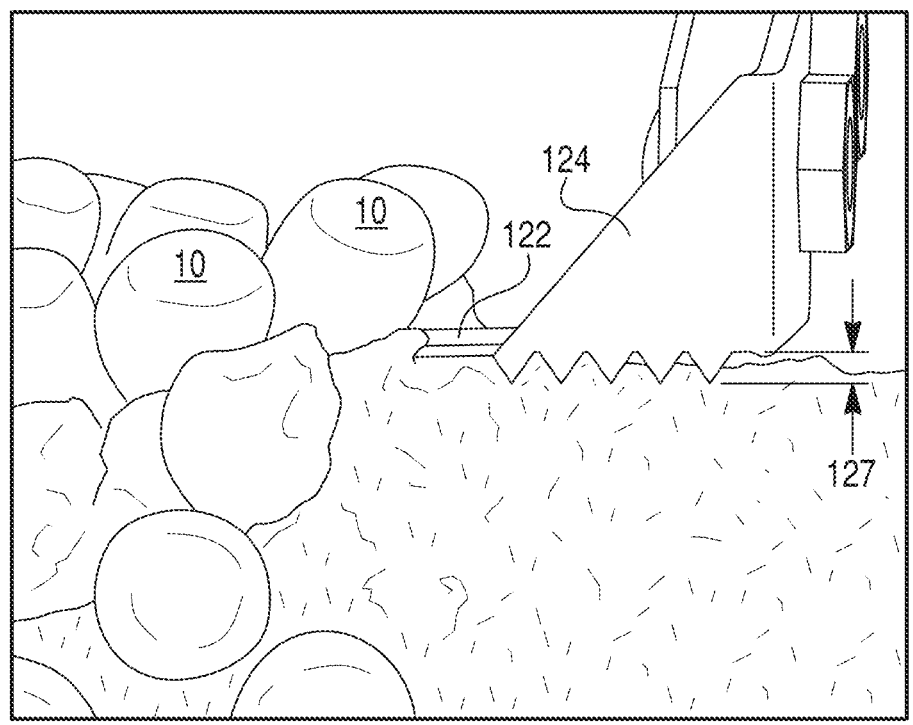
FIG. 9B is a close-up side perspective view of the arm of FIG. 9A.
Figure 10A:
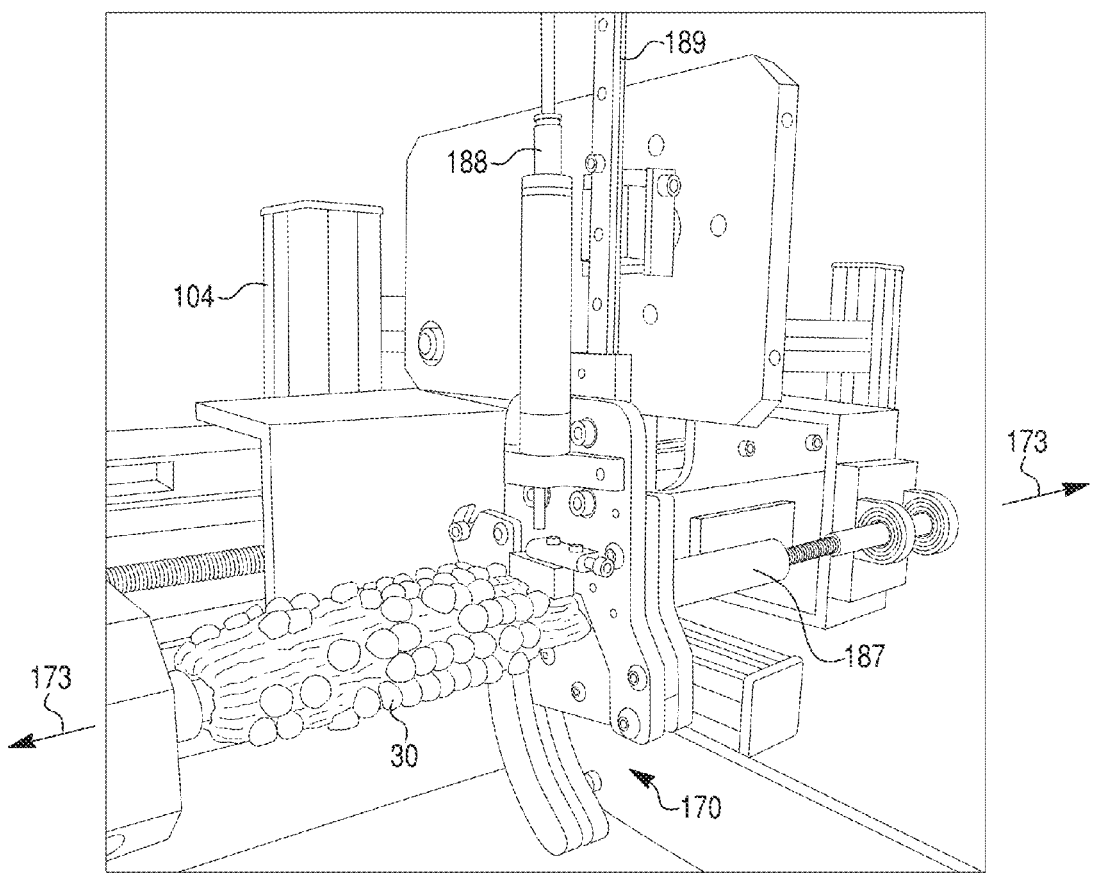
FIG. 10A is a perspective view of an exemplary cob-following cutting assembly of a seed removal system as disclosed herein.
Figure 10C:
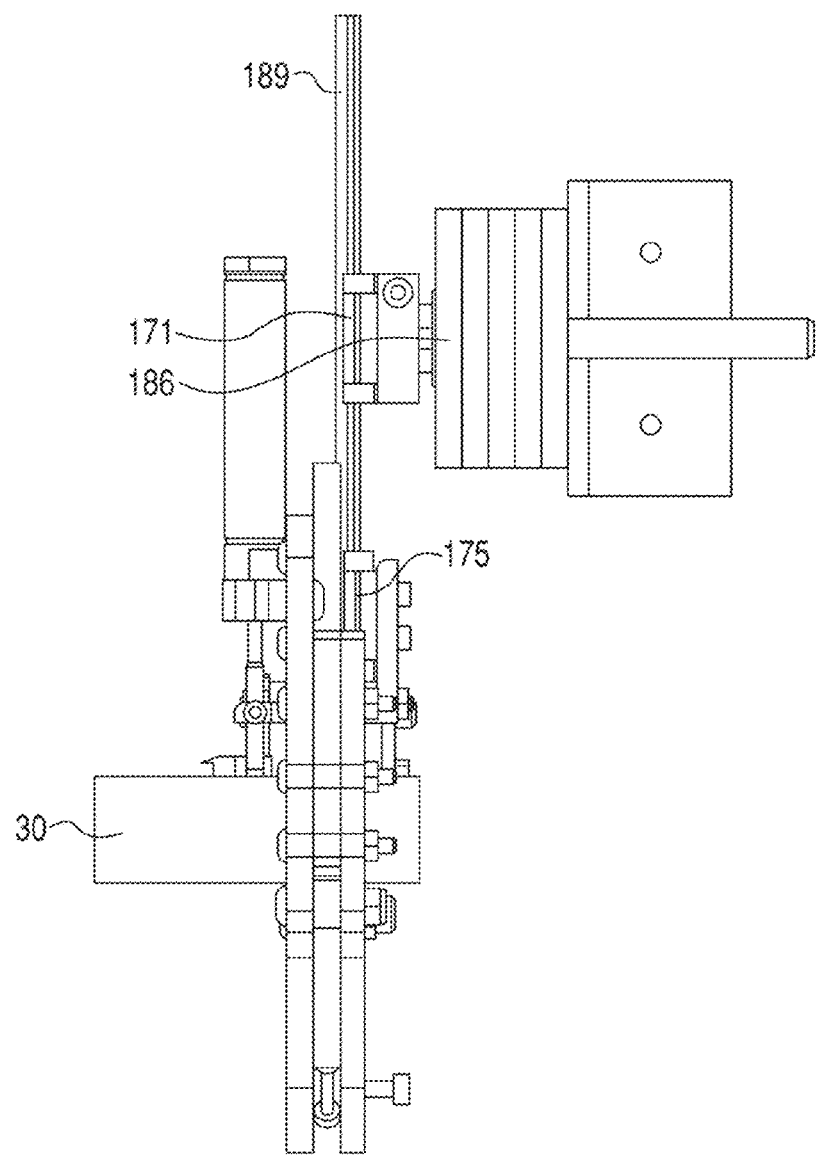
FIG. 10C is a side perspective view of the cob-following cutting assembly of FIG. 10A.

In another aspect, each cutting arm 126 of the at least one cutting arm of the cutting assembly 120 can further comprise a grinding portion 124. Optionally, in this aspect, the cutting portion 122 of each respective cutting arm 126 can be offset relative to the grinding portion 124 of the cutting arm by a distance 127 ranging from about 0.5 mm to about 2.0 mm, moving radially away from the orientation axis 121. In exemplary aspects, the grinding portion 124 can be generally oriented (e.g., face) toward the orientation axis 121 (and the ear), whereas the cutting portion 122 can be generally oriented (e.g., face) in a direction that is substantially parallel to the orientation axis. In further exemplary aspects, the cutting portion 122 and the grinding portion 124 of the cutting arm 126 can define respective teeth 123, 125 for improved cutting and grinding action. Optionally, in exemplary aspects, the teeth of the grinding portion 124 can be angularly oriented relative to the teeth of the cutting portion 122. As shown in FIG. 9B, in a cutting position, the cutting portion 122 of the cutting arm 126 can be radially spaced from the grinding portion 124 relative to the orientation axis 121; that is, the cutting portion 122 can be spaced farther away from the cob than the grinding portion 124. In operation, the cutting portion 122 can be configured to undercut kernels that are rotating about the orientation axis 121, while the grinding portion 124 can be configured to grind down the denser woody ring of the cob. With the grinding portion 124 maintaining a position against the woody ring of the ear, the cutting portion 122 is able to undercut the kernels at a position immediate proximal to the cob from the kernels.

In an additional aspect, the cutting assembly 120 can further comprise at least one air cylinder 150 that is operatively coupled to the at least one cutting arm 126 of the cutting assembly 120. In this aspect, the at least one air cylinder 150 can be configured to selectively apply pressure to the at least one cutting arm 126 to effect movement of at least the cutting portion 122 of each respective cutting arm toward the orientation axis 121. However, it is contemplated that any conventional means for effecting pivotal and/or rotational movement of the at least one cutting arm 126 can be used in place of the at least one air cylinder 150.

In a further aspect, the cutting assembly 120 can further comprise a support element 140 (e.g., tailstock). In this aspect, the at least one cutting arm 126 can be positioned between the spindle actuator 130 and the support element 140 relative to the orientation axis 121, and the support element 140 can be configured to securely engage a distal portion 119c of the spindle 115 that extends through an ear of corn to stabilize the ear of corn during operation of the at least one cutting arm 126. In use, the support element 140 can be configured to move axially with the spindle 115 (and ear of corn). In exemplary aspects, the system 100 can comprise a return element 142 (e.g., spring return) that is configured to return the support element 140 to an operative position following axial advancement of the support element with the spindle 115.

In exemplary aspects, the cutting assembly 120 can further comprise a mounting plate 106 that extends radially outwardly from a frame 104 relative to the longitudinal axis 102 of the system 100. In these aspects, the at least one cutting arm 126 can be pivotally mounted to the mounting plate 106. Optionally, it is contemplated that the at least one air cylinder 150 can have a distal end that is secured to the mounting plate 106. In further exemplary aspects, the mounting plate 106 can define an opening 108 that is configured to receive the spindle 115 and ear 30 as the spindle and ear are advanced relative to the orientation axis 121.

In further exemplary aspects, the at least one cutting arm 126 can define a cutting orifice, which corresponds to the smallest diameter which is cut by the at least one cutting arm when the cutting arms are at their innermost positions relative to the orientation axis 121. In these aspects, at least one orifice pin 162 can be operatively coupled to each cutting arm 126 and configured to lock each cutting arm in a position that defines an orifice of a desired size. In further aspects, each orifice pin 162 can be operatively coupled to an orifice adjustment mechanism 160, which can be selectively rotated to effect desired movement of the orifice pin 162, to thereby adjust the size of the orifice defined by the cutting arms 126.

In still further exemplar aspects, each cutting arm 126 can optionally be coupled to a scraping element 128. Optionally, in these aspects, each scraping element 128 can be mounted to a respective cutting arm 126. In operation, it is contemplated that the scraping elements 128 can be configured to glide with movement of the cutting arms 126 to stabilize the spindle 115 and ear 30 during a cutting operation.

A cob-following cutting assembly 170 is depicted in FIGS. 10A-10D. In one aspect, the system 100 can comprise a spindle actuator 130 and a linear actuator 190 as disclosed above with reference to cutting assembly 120. In operation, the spindle actuator 130 can be configured to operatively engage a proximal portion 119b of the spindle 115, and the spindle actuator 130 can be configured to rotate the spindle 115 relative to an orientation axis 173. Additionally, the linear actuator 190 can be configured to axially advance the spindle assembly, including the spindle 115, relative to the orientation axis 173.

In an additional aspect, the cutting assembly 170 can comprise a cutting head 176 that is axially spaced from the at least one spindle actuator 130 relative to the orientation axis 173. In this aspect, the cutting head 176 can comprise a body portion 177 that defines first and second engagement surfaces 184*a*, 184*b* that face the orientation axis 173. In another aspect, the cutting head 176 can comprise a support arm 178 that is pivotally coupled to the body portion 177 and biased radially inwardly toward the orientation axis 173. In this aspect, the support arm 178 can define a third engagement surface 180. In an additional aspect, the first, second, and third engagement surfaces 184*a*, 184*b*, 180 can cooperate with adjacent portions of the body portion 177 to define a receptacle 185 that surrounds the orientation axis 173. In this aspect, the receptacle 185 can be configured to receive at least a portion of an ear of corn positioned in alignment with the orientation axis 173. Optionally, the support arm 178 can be biased radially inwardly by a spring 182, which, in exemplary aspects, can be a constant force spring.

In a further aspect, the cutting assembly 170 can comprise a cutting member 172 that is secured to the body portion 177 and radially biased toward the orientation axis 173. In this aspect, the cutting member 172 of the cutting head 176 can be configured to remove intact immature corn kernels from the cob of an ear positioned on the spindle 115 as the ear is advanced relative to the orientation axis 173. Optionally, the cutting member 172 can comprise a cutting element and a grinding element 174. Optionally, it is contemplated that the cutting element and the grinding element 174 can have the same general arrangement as the cutting and grinding portions of cutting assembly 120, described above. In particular, it is contemplated that the cutting member 172 can be radially offset from the grinding element 174 relative to the orientation axis 173. It is further contemplated that the grinding element 174 can be generally oriented toward the orientation axis 173 (and the ear), whereas the cutting member can be generally oriented in a direction that is substantially parallel to the orientation axis 173.

In another aspect, the system 100 can comprise a support frame 104. In this aspect, the cutting head 176 can be pivotally coupled to the frame 104 such that the cutting head can freely pivot about the orientation axis 173. Optionally, the system 100 can further comprise a bearing block 186 that operatively couples the cutting head 176 to the frame 104.

In an additional aspect, a position of the cutting head 176 relative to a vertical axis 103 is selectively adjustable. In this aspect, the vertical axis 103 can be substantially perpendicular to the orientation axis 173. Optionally, it is contemplated that the system 100 can further comprise a slide mechanism 171 and a vertical support 189 operatively connected to the slide mechanism, with the slide mechanism 171 being coupled to the cutting head 176 and being configured to permit free movement of the cutting head relative to the vertical axis 103.

In a further aspect, a position of the cutting member 172 of the cutting head 176 relative to the vertical axis 103 (and the body portion 177) is selectively adjustable. Optionally, it is contemplated that the system 100 can further comprise a slide mechanism 175 operatively connected to the body portion 177 of the cutting head 176, with the slide mechanism 175 being coupled to the cutting member 172 and being configured to permit free movement of the cutting member relative to the vertical axis 103 and to the body portion 177 of the cutting head 176.

In still a further aspect, the system 100 can further comprise at least one air cylinder 188 coupled to the cutting member 172 of the cutting head 176. In this aspect, the at least one air cylinder 188 can be configured to selectively apply pressure to the cutting member 172 to effect movement of the cutting member toward the orientation axis 173.

In yet another aspect, the cutting assembly 170 can further comprise a support element 140 (e.g., tailstock) as disclosed with respect to cutting assembly 120. In this aspect, the cutting head 176 can be positioned between the spindle actuator 130 and the support element 140 relative to the orientation axis 173, and the support element 140 can be configured to securely engage a distal portion 119*c* of the spindle 115 that extends through an ear of corn to stabilize the ear of corn during operation of the cutting member 172 of the cutting head 176. In use, the support element 140 can be configured to move axially with the spindle 115 (and ear of corn). In exemplary aspects, the system 1100 can comprise a return element (e.g., spring return) that is configured to return the support element 140 to an operative position following axial advancement of the support element with the spindle 115.

In further optional aspects, the system 100 can further comprise a starting cylinder 187 that is configured to selectively adjust an operative position of the cutting head 176 (and cutting member 172) relative to a cob. In these aspects, the starting cylinder can be configured to lock the cutting head in an operative position in which the cutting head defines a cutting orifice, which corresponds to a smallest diameter which is cut by the cutting member 172 as the cob advances relative to the orientation axis 173. In these aspects, the starting cylinder 187 can be operatively coupled to the cutting head 176 and configured to lock the cutting had in a position that defines a cutting orifice of a desired size.

In exemplary aspects, it is contemplated that an ear of corn can be placed in a centering fixture, such as, for example, the at least one clamp assembly disclosed herein. It is further contemplated that stalk material covering the center of the ear, at the proximal end, can be removed to expose the pith. After the stalk material is removed from the ear, a spindle can be inserted into the center of the ear at the proximal end, as disclosed herein. As shown in FIGS. 5A-5C, it is contemplated that a rigid spindle can reduce ear curvature. Once the spindle is inserted into the ear, the ear can be released from the centering fixture (e.g., at least one clamp assembly). During rotation, the ear can be driven axially through a cutting assembly as disclosed herein, starting with the distal end of the ear.

Optionally, in one exemplary aspect, when an independent arm cutting assembly as disclosed herein is used to remove the corn kernels from a cob, the cutting mechanism can comprise a cutting portion and/or a grinding portion that can be mounted on one or more cutting arms that pivot at arcs intersecting the orientation axis. It is further contemplated that the grinding portion can be configured to rapidly advance radially towards the center of the ear by removing the softer outer structures of the ear. This radial removal of the material can greatly decrease when the grinding portion reaches the denser woody ring of the ear. In this aspect, it is contemplated that the cutting portion, which is positioned at a fixed offset from the grinding portion relative to the cob, can release intact corn kernels from the cob at a corresponding offset above the woody ring of the ear. The removed corn kernels can then fall away into a bin or other receptacle.

Optionally, in another exemplary aspect, when a cob-following cutting assembly as disclosed herein is used to remove the corn kernels from a cob, the cutting mechanism can comprise a v-shaped guide (defined by the first and second engagement surfaces) which can contact the ear and constantly positions the cutting member at a desired location relative to the ear. It is further contemplated that the support arm can be spring-loaded to maintain 3-point contact with the ear. The cutting member, which can have an integrated grinder or glider, can be mounted on a sliding mechanism designed to move the cutting edge of the blade perfectly radially toward the center of the ear while maintaining the depth of the cut. As the ear rotates, the cutting head can pivot and translate to maintain perfect radial alignment with the ear. In this aspect, it is contemplated that the cutting member can be forced radially toward the cob using an air cylinder 188, such as, for example and without limitation, a low-friction air cylinder. Initially, at the distal end of the ear where there are often unfertilized kernels and a softer woody ring, the air cylinder can be configured to apply radial minimal radial force (a "low force" operating condition). After reaching an area of the cob where kernels are present, the woody ring can be denser, and the air cylinder can be configured to apply greater radial force (a "high pressure" operating condition) to the cutting member, and this setting can be applied for the remaining length of the ear.

Following removal of the corn kernels as disclosed herein, the spindle can be withdrawn from the cob, and the cob can be discarded when the cutting assembly reaches the proximal end of the ear.

iii. Kernel Conditioning

In one aspect, it is contemplated that the intact corn kernels can be sorted to separate out any unfertilized corn kernels, debris, or damaged corn kernels. It is further contemplated that the intact corn kernels can be agitated in air and/or water to remove loose chaff and bees' wings. Any kernels with excess attached chaff can be run through a separate "de-chaffing" process to remove the excess chaff. The intact kernels can then be ready for further processing.

Figure 12A:
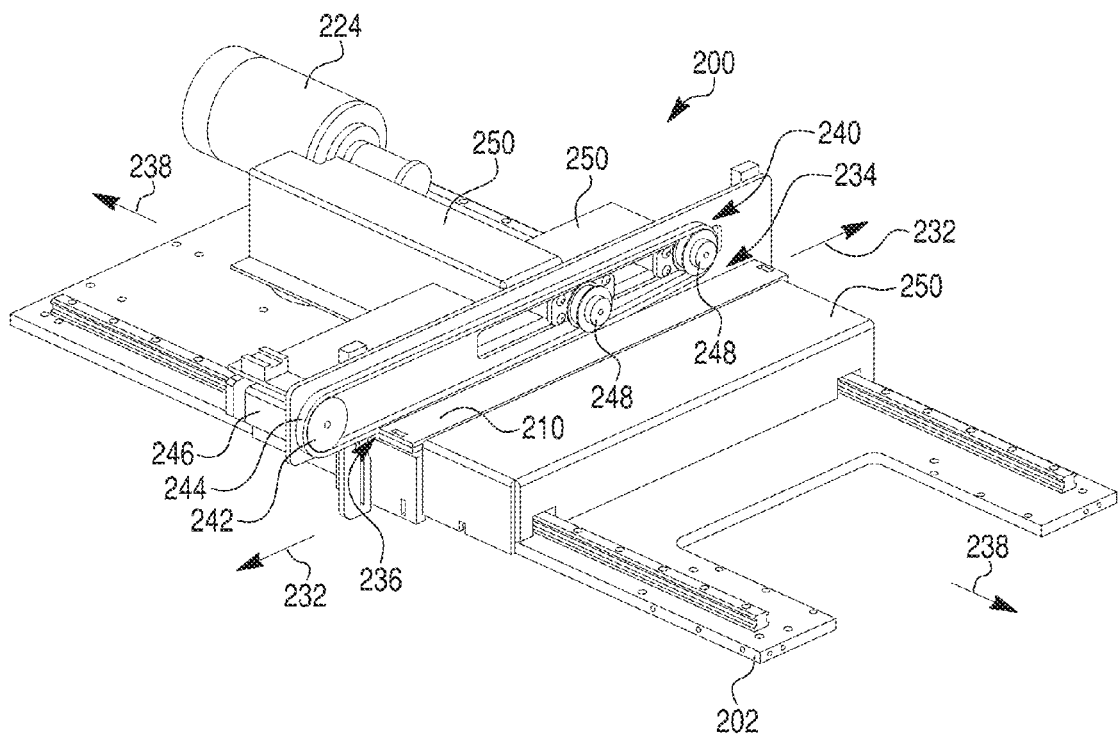
FIG. 12A is a perspective view of an exemplary chaff removal system as disclosed herein.
Figure 12B:
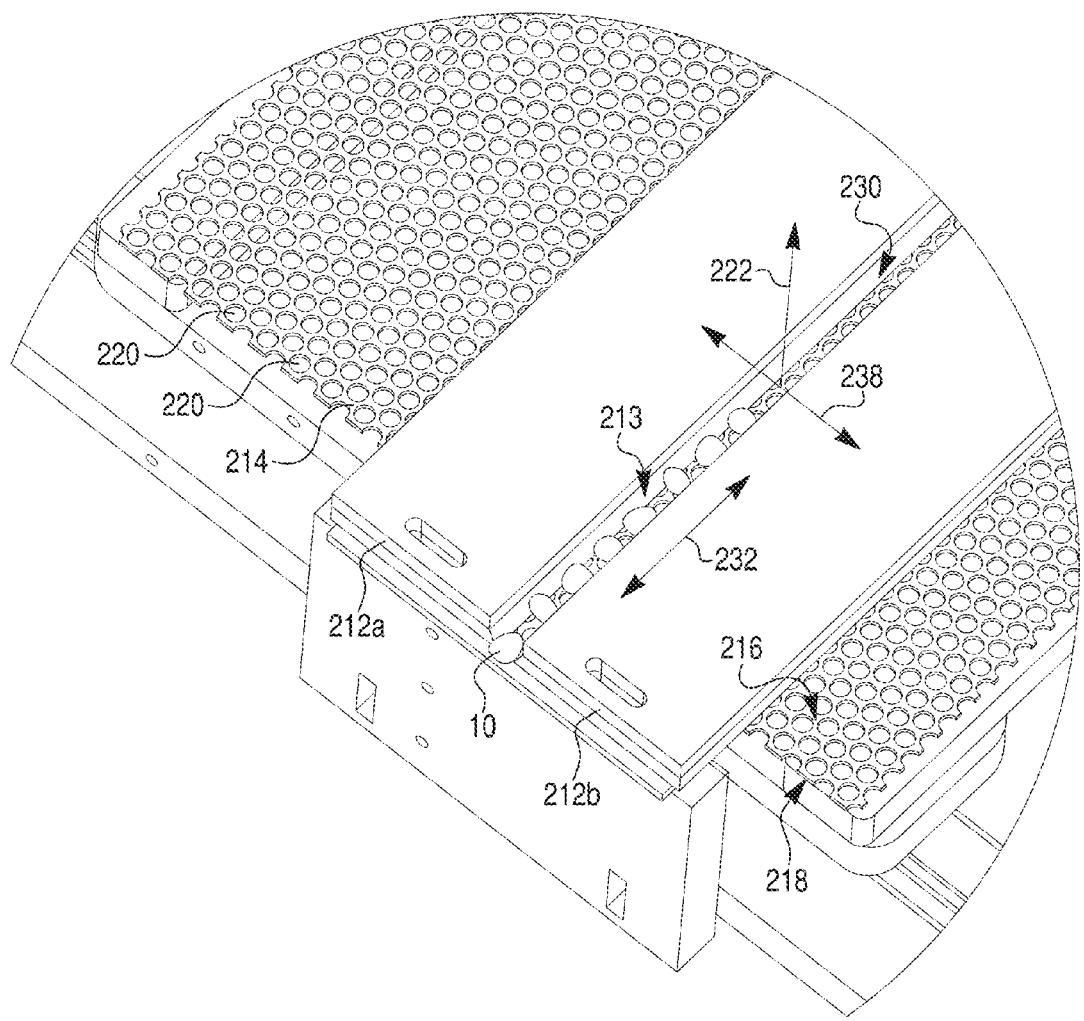
FIG. 12B is a close-up perspective view of an outlet portion of the chaff removal system of FIG. 12A.
Figure 12C:
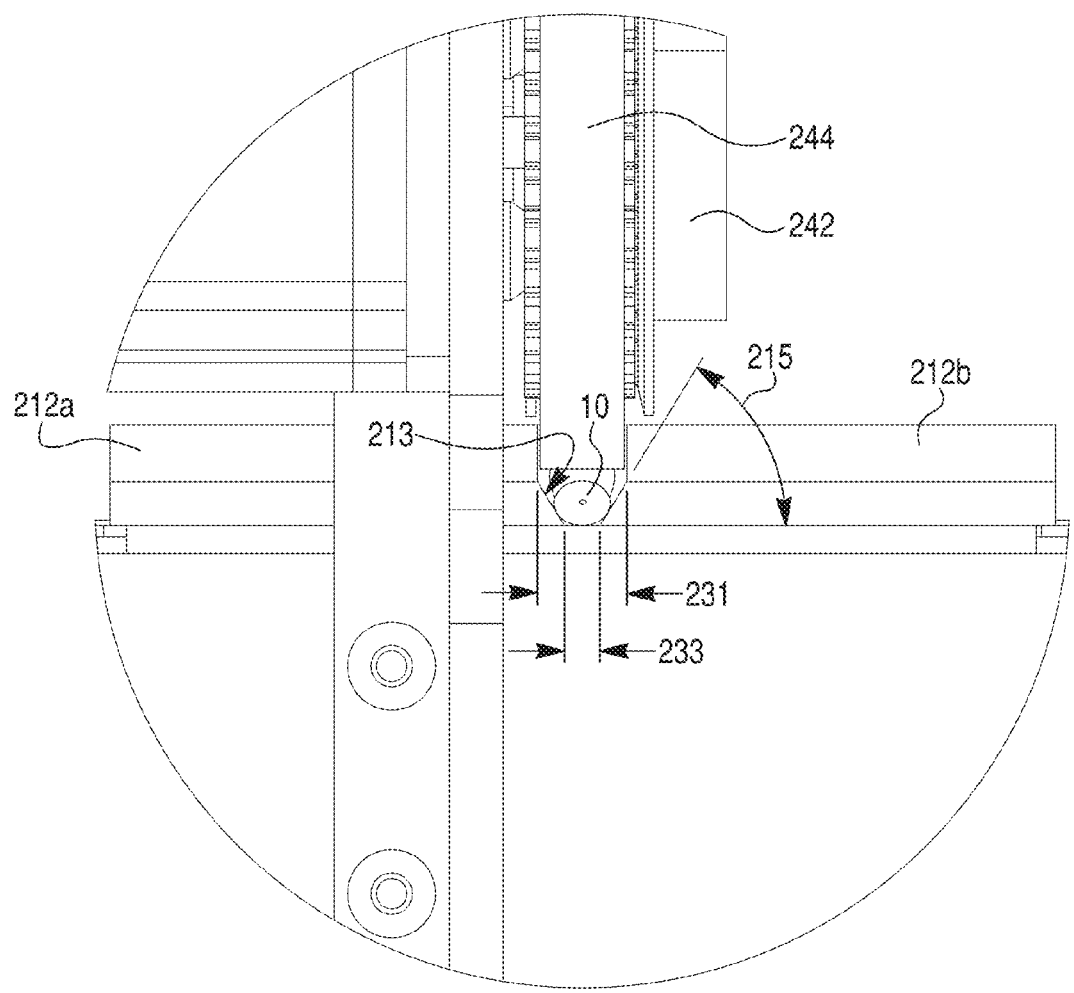
FIG. 12C is an end view of the outlet portion of the chaff removal system of FIG. 12A.

An exemplary system 200 for removing chaff from corn kernels is depicted in FIGS. 12A-12C. Optionally, the chaff removal system 200 can be provided as part of an overall embryo processing system 300 as further described herein. In one aspect, the system 200 can comprise a plate assembly 210 having at least one guide plate 212a, 212b and a perforated plate 214. In this aspect, the perforated plate 21 can have a first surface 216 and an opposed second surface 218 and define a plurality of bores 220 that extend from the first surface to the second surface relative to a first axis 222. In another aspect, inner surfaces 213 of the at least one guide plate 212a, 212b and the first surface 216 of the perforated plate 214 can cooperate to define a receiving channel 230 that extends parallel to a second axis 232 that is substantially perpendicular to the first axis 222. In exemplary aspects, the at least one guide plate 212a, 212b can comprise stacks of guide plates on opposing sides of the receiving channel 230 that cooperate to define the inner surfaces 213. The receiving channel 230 can have an inlet portion 234 and an outlet portion 236. The inlet portion 234 of the receiving channel 230 can be configured to receive at least one corn kernel, and the perforated plate 214 can be configured for selective oscillating movement relative to a third axis 238 that is substantially perpendicular to both the first and second axes 222, 232. In exemplary aspects, the first surface 216 of the perforated plate 214 can have a desired surface roughness. Optionally, in these aspects, the desired surface roughness can be provided by burrs defined in the first surface 216 of the perforated plate 214 as a result of a punching process. However, it is contemplated that the surface roughness can be provided in any conventional manner.

In another aspect, the system 200 can comprise a pulley assembly 240 configured to effect movement of the at least one seed relative to the second axis 232 from the inlet portion 234 of the receiving channel 230 of the plate assembly 210 to the outlet portion 236 of the receiving channel of the plate assembly. In use, the at least one guide plate 212a, 212b of the plate assembly 210 can be configured to restrict movement of the at least one corn kernel relative to the third axis 238. During oscillating movement of the perforated plate 214, the perforated plate can be configured to pull chaff away from the at least one corn kernel as the corn kernel moves relative to the second axis 232 within the receiving channel 230 of the plate assembly 210. As shown in FIG. 12C, the inner surfaces 213 of the guide plates can be positioned at a selected angle 215 relative to the third axis 238. In exemplary aspects, the selected angle 215 can optionally range from about 10 degrees to about 75 degrees. As further depicted in FIG. 12C, the receiving channel 230 can have a top portion with a maximum diameter 231 and a bottom portion (closest to the first surface of the perforated plate) with a minimum diameter 233, with the minimum diameter being smaller than the smaller dimension of the at least one corn kernel. Thus, when the kernel is positioned within the receiving channel 230, the kernel will not extend below the channel, but portions of any chaff attached to the kernel can extend below the channel and engage the perforated plate.

In an additional aspect, the system 200 can further comprise a motor 224 operatively coupled to the perforated plate 214. In this aspect, the motor 224 can be configured to effect selective oscillating movement of the perforated plate 214 relative to the third axis 238. In exemplary aspects, the motor 224 can be configured to effect selective oscillating movement of the perforated plate 214 relative to the third axis 238 at a selected oscillation rate. Optionally, in these aspects, the selected oscillation rate can range from about 20 strokes per minute to about 150 strokes per minute. In further aspects, it is contemplated that each stroke can correspond to a selected stroke distance relative to the third axis. In these aspects, the selected stroke distance can optionally range from about 1 inch to about 3 inches.

In a further aspect, the pulley assembly 240 of the system 200 can comprise a belt pulley 242 and a belt roll 244 that is operatively coupled to the belt pulley 242. In this aspect, the belt roll 244 can be configured for engagement with the at least one corn kernel within the receiving channel 230 of the plate assembly 210. In another aspect, the pulley assembly 240 can further comprise a belt motor 246 operatively coupled to the belt pulley 242 and configured to effect movement of the belt roll 244 at a selected belt speed. Optionally, in this aspect, the selected belt speed can range from about 50 inches per minute to about 200 inches per minute. In an additional aspect, the pulley assembly 240 can further comprise at least one idler pulley 248 that is axially spaced from the belt pulley 242 relative to the second axis 232. In exemplary aspects, the belt roll 244 can comprise soft foam (e.g., a soft foam cover) that is configured to effect a tumbling motion of the kernels to ensure that all sides of the kernels have an opportunity to be processed by the perforated plate 214.

Optionally, in another aspect, the system 200 can further comprise at least one safety guard 250 that at least partially surrounds the perforated plate 214 during oscillating movement of the perforated plate. In further optional aspects, the system 200 can comprise a frame 202 that is configured to support the plate assembly 210, the pulley assembly 240, and any safety guards 250 that enclose the perforated plate 214.

In exemplary aspects, and with reference to FIG. 13B, the system 200 can be used in a method of removing chaff from at least one corn kernel. In one aspect, the method can comprise positioning at least one immature corn kernel within an inlet portion of the receiving channel defined by the plate assembly. In another aspect, the method can comprise effecting selective oscillating movement of the perforated plate relative to the third axis, which is substantially perpendicular to both the first and second axes. In a further aspect, the method can comprise selectively activating the pulley assembly to engage and effect movement of the at least one immature corn kernel relative to the second axis from the inlet portion of the receiving channel of the plate assembly to the outlet portion of the receiving channel of the plate assembly. In operation, the at least one guide plate of the plate assembly can restrict movement of the at least one immature corn kernel relative to the third axis. During oscillating movement of the perforated plate, the perforated plate can pull chaff away from the at least one immature corn kernel as the corn kernel moves relative to the second axis within the receiving channel of the plate assembly.

b. Singulation Assembly

As further described herein, after the corn kernels of an ear have been removed, the corn kernels can be "singulated" to permit processing of individual seeds, one at a time.

i. Singulation Assembly (Dry)

Exemplary singulation assemblies that singulate seeds without the use of fluid flow are depicted in FIGS. 14A-16B. In one aspect, the singulation assembly 310 can be configured to receive a plurality of corn kernels and separate a single corn kernel from the remaining corn kernels of the plurality of corn kernels. In operation, the singulation assembly can be configured to deliver a single corn kernel to an indexing assembly as further disclosed herein. In one aspect, the singulation assembly 310 has an outlet 325 that is positioned in communication with the indexing assembly. Optionally, the singulation assembly 310 can be provided as part of an overall embryo processing system 300 as further described herein. In exemplary aspects, and as further described herein, the embryo processing system 300 can have a longitudinal axis 302, a transverse axis 304, and a vertical axis 306.

In another aspect, the singulation assembly 310 can comprise a hopper 312 configured to receive a plurality of corn kernels. In this aspect, the hopper 312 can have a longitudinal axis and define an outlet 313. The outlet can be any suitable shape, such as, for example and without limitation, side opening to a receptacle (FIGS. 14A-15B) or a bottom opening to a fimnel (FIGS. 16A-16B). In a further aspect, the singulation assembly 310 can comprise a trough 316 having a longitudinal axis 319 and being configured to sequentially receive the plurality of corn kernels from the outlet 313 of the hopper 312. In this aspect, the longitudinal axis 319 of the trough can be substantially parallel to the longitudinal axis 302 of the system 300. In another aspect, the trough 316 can define a channel 317 that extends substantially parallel to the longitudinal axis 319 of the trough. In this aspect, it is contemplated that the channel 317 can define the outlet 325 of the singulation assembly 310.

In a further aspect, the singulation assembly 310 can comprise a first actuator 314 operatively coupled to the hopper 312. In this aspect, the first actuator 314 can be configured to effect vibration of the hopper 312.

In an additional aspect, the singulation assembly 310 can further comprise a sensor 320 configured to produce an output indicative of the presence or absence of a corn kernels within the trough 316. In this aspect, the sensor 320 can be positioned in operative communication with the first actuator 314 and configured to communicate the output to the first actuator. In response to receiving an output indicative of the presence of an immature monocot seed within the trough 316, the first actuator 314 can be configured to cease vibration of the hopper 312. Optionally, in exemplary aspects, the sensor 320 can be an optical sensor.

Optionally, as shown in FIGS. 14A-15B, the longitudinal axis of the hopper 312 can be substantially perpendicular to the longitudinal axis 319 of the trough 316. Alternatively, as shown in FIGS. 16A-16B, the longitudinal axis of the hopper 312 can be substantially parallel to or in alignment with the longitudinal axis 319 of the trough 316.

Optionally, in a further exemplary aspect, the singulation assembly 310 can further comprise a second actuator 318 that is operatively coupled to the trough 316. In this aspect, the second actuator 318 can be configured to effect vibration of the trough 316.

Optionally, in a further aspect, the singulation assembly 310 can comprise a base 322 that is configured to stabilize the singulation assembly. In an additional optional aspect, the singulation assembly 310 can comprise a frame 324 that extends upwardly from the base and supports the hopper 312 and/or trough 316 at a desired vertical position relative to the base 322.

In exemplary aspects, and with reference to FIG. 13C, the disclosed singulation assemblies can be used in a method of obtaining an isolated corn kernel, in one aspect, the method can comprise positioning a plurality of corn kernels within a hopper. In another aspect, the method can comprise effecting vibration of the hopper. In a further aspect, the method can comprise sequentially receiving the plurality of corn kernels from the outlet of the hopper within the channel of the trough. Optionally, the method can further comprise using a sensor to produce an output indicative of the presence or absence of a corn kernel within the trough, and communicating the output to a first actuator that is configured to effect vibration of the hopper. In response to receiving the output, the first actuator can cease vibration of the hopper. Optionally, in a further aspect, the method can further comprise effecting vibration of the trough. After the kernels are received within the trough, the kernels can move within the channel of the trough toward an indexing assembly as further disclosed herein.

ii. Singulation Assembly (Wet)

Figure 17A:
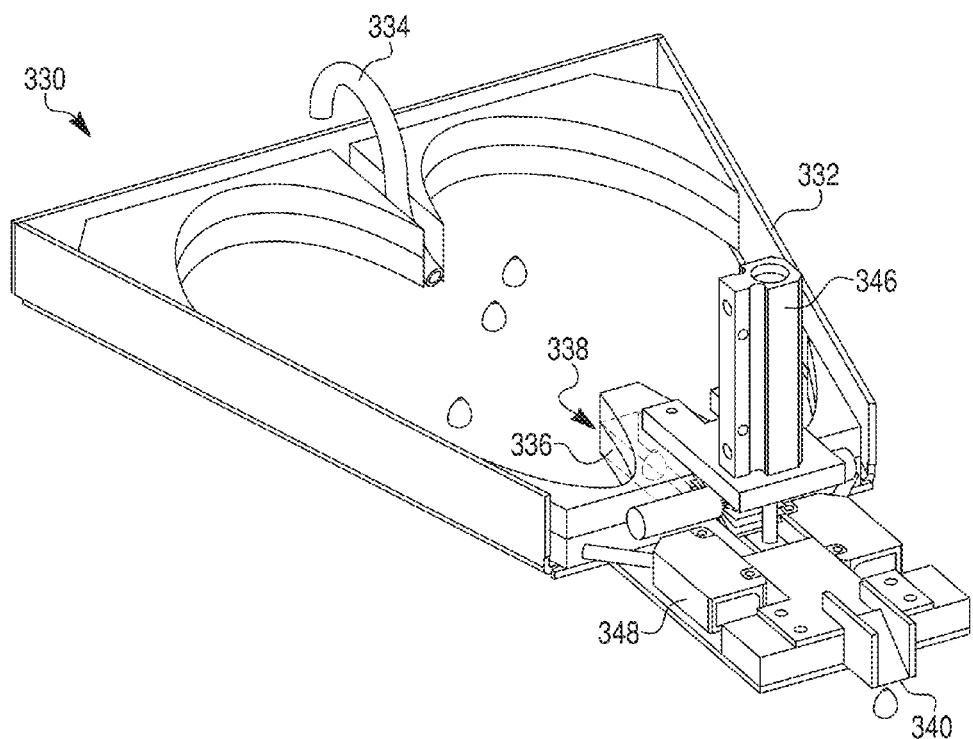
FIG. 17A is a perspective view of an exemplary singulation assembly for singulating corn kernels using fluid flow, as disclosed herein.
Figure 17B:
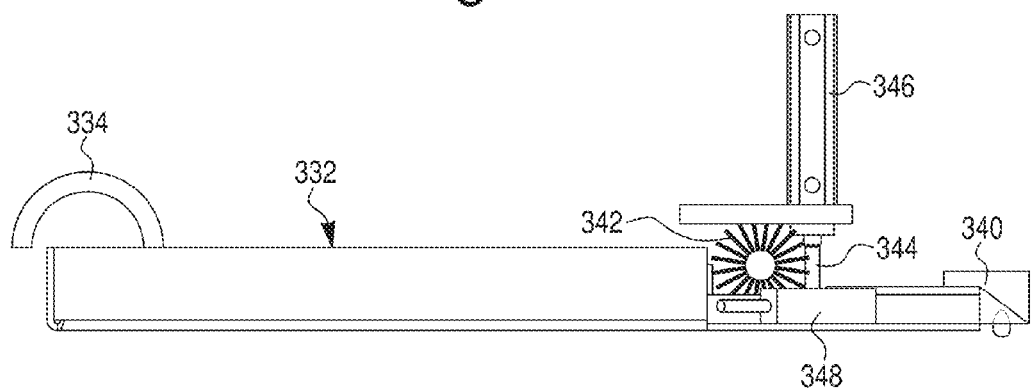
FIG. 17B is a side perspective view of the singulation assembly of FIG. 17A.
Figure 17C:
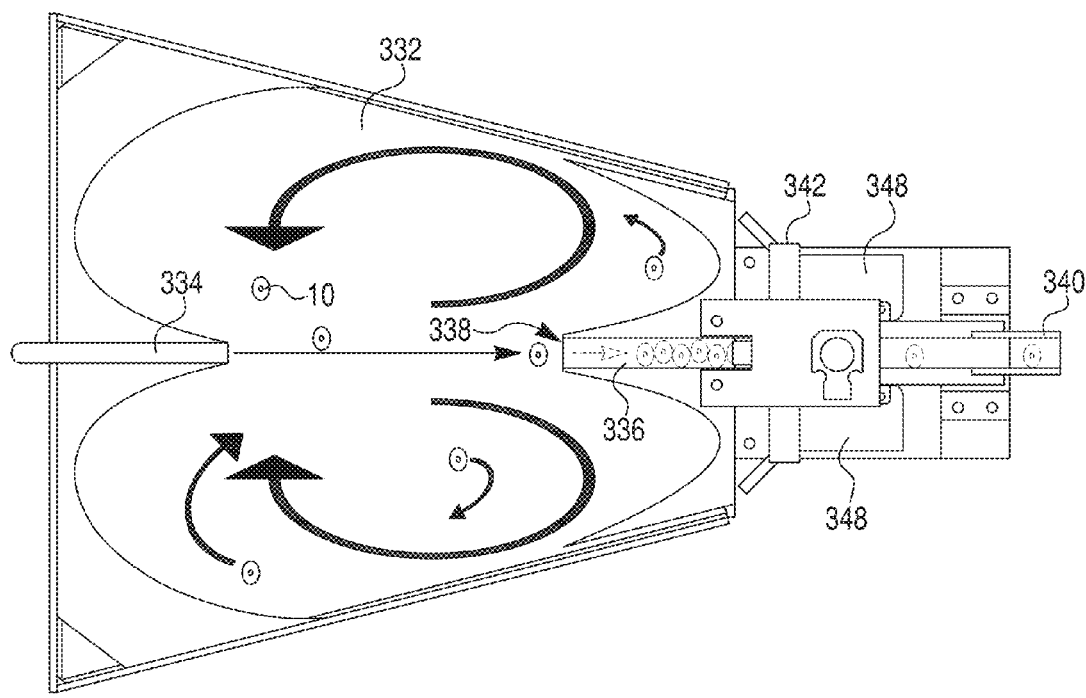
FIG. 17C is a schematic top perspective view of the singulation assembly of FIG. 17A.

An exemplary singulation assembly that singulates seeds with the use of liquid flow is depicted in FIGS. 17A-17C. In one aspect, the singulation assembly 330 comprises a hopper as disclosed with respect to singulation assembly 310. In another aspect, the singulation assembly 330 comprises a circulation trough 332 that receives water or another selected liquid. A liquid conduit 334 is positioned in communication with the circulation trough 332 to permit selective delivery of liquid to the circulation trough. In use, the outlet of the hopper is positioned in communication with the circulation trough 332, and the circulation trough receives corn kernels from outlet of the hopper. The liquid conduit 334 can be positioned in communication with a liquid source, which can selectively deliver liquid to the liquid conduit to provide circulation and flow to the corn kernels within the circulation trough.

In another aspect, the singulation assembly 330 can comprise a track portion 336 having an inlet 338 and an outlet 340. The inlet 338 of the track portion 336 can be positioned in fluid communication with the circulation trough 332 at a position substantially opposed from the liquid conduit 334. In operation, the inlet 338 of the track portion 336 can be configured to receive corn kernels as the seeds are circulated within the circulation trough 332.

In a further aspect, the singulation assembly 330 can comprise a gate assembly positioned along the track portion 336 at a position intermediate the inlet 338 and the outlet 340. As shown, the gate assembly can have a brush 342 (optionally, a bristle brush), a gate 344, an actuator 346, and an optical sensor 348. The brush 342 can be configured for rotational movement relative to an axis that is substantially perpendicular to a direction of liquid flow within the track 336 such that the brush (e.g., the bristles of the brush) forces kernels within the track portion 336 toward the outlet 340. The actuator 346 can be operatively coupled to the gate 344 and configured to move the gate 344 about and between an open position and a blocking position. The optical sensor 348 can be positioned to detect the presence or absence of a corn kernel within the track and proximate the gate. With the gate in the blocking position, upon detecting the presence of a corn kernel, the optical sensor 348 can be configured to communicate an output to the actuator 346, thereby effecting movement of the gate from the blocking position to the open position to permit passage of the corn kernel. Optionally, the output can be communicated to a rotational actuator (not shown) positioned in operative communication with the brush such that, upon detecting the presence of a corn kernel, the rotational actuator can be configured to cease rotation of the brush. After the liquid flow (alone or in combination with the brush) pushes the corn kernel through the open gate, the corn kernel reaches the outlet 340 of the track 336, which serves as the outlet of the singulation assembly 330.

In one exemplary aspect, it is contemplated that intact kernels can be placed in a hopper as disclosed herein. It is further contemplated that the hopper can vibrate to feed the intact kernels to the circulating trough. In this aspect, a fluid jet/supply in communication with the liquid source can provide circulation and flow to the kernels within the circulating trough. The liquid flow can catch a kernel and can sequentially feed the track. In operation, the bristle brush can rotate until a kernel blocks the optical sensor. Once the optical sensor is blocked, the gate can open, and the kernel can advance with the flow to the outlet of the track.

iii. Other Exemplary Singulation Assemblies

In an exemplary aspect, it is contemplated that monocot seeds can be singulated from other monocot seeds by first positioning the monocot seeds in a liquid bath. In this aspect, the liquid bath can be positioned within a container, and the container can define an outlet opening or passageway configured to receive a single monocot seed at a given time. The container can be configured to promote flow of liquid through the outlet opening or passageway such that an individual monocot seed passes through the opening or passageway, thereby ensuring singulation of each respective monocot seed from the other monocot seeds within the container. Optionally, mechanical means can be provided for effecting movement of the monocot seeds toward the outlet opening or passageway. The outlet opening or passageway can be positioned in fluid communication with a force application assembly as further disclosed herein.

In other exemplary aspects, it is contemplated that any conventional means for singulating monocot seeds from other monocot seeds can be employed. For example, it is contemplated that the means for singulating monocot seeds can comprise a hopper that is configured to permit exit of only a single monocot seed at a time.

c. Automated Extraction Systems

In exemplary aspects, the automated system can be further configured to apply force to the corn kernels (or other monocot seeds) to extract the corn embryos of the corn kernels without damage to the corn embryos. It is contemplated that any conventional force application means can be employed to form an opening or hole in the proximal end of a corn kernel as described herein. In exemplary aspects, it is contemplated that the force application means can be a cutting means, such as, for example and without limitation, a knife or blade assembly as is known in the art. However, it is contemplated that the force application means can be any conventional mechanism for creating a hole or opening, including, for example and without limitation, pinching means, ripping means, tearing means, squeezing means, and crushing means. In various aspects, it is contemplated that the force application means can be incorporated into an automated system for forming an opening or hole in at least one corn kernel as disclosed herein.

i. Automated Extraction System Having Integrated Indexing Transport and Cutting Assemblies As discussed above, an automated embryo processing system 300 can be provided. In exemplary aspects, and as further described herein, the embryo processing system 300 can have a longitudinal axis 302, a transverse axis 304, and a vertical axis 306. In exemplary aspects, the system 300 can comprise a liquid bath 305, an indexing assembly 350, a belt assembly 380, a force application assembly 420, and an embryo collection tube 480 as further disclosed herein. Optionally, the system 300 can further comprise a singulation assembly (e.g., singulation assembly 310 or singulation assembly 330). Optionally, the system 300 can further comprise a chaff removal system 300 and/or a kernel removal system 100 as further disclosed herein. In exemplary aspects, the system 300 can comprise a housing 308 that is configured to receive the various actuators and portions of the drive shafts disclosed herein. It is contemplated that all electronic components of the system 300 can be securely received within housing 308, which, in operation, can be axially spaced from the fluid bath 305 relative to the vertical axis 306. In exemplary aspects, it is contemplated the housing 308 can be selectively detached from the remaining portions of the system 300 to permit cleaning of the various non-electrical components of the system without exposure to electrical components. Although disclosed below as being part of an integrated system, it is contemplated that the indexing assembly 350, belt assembly 380, and force application assembly 420 can be provided as independent and/or freestanding systems.

1. Indexing Assembly

An exemplary indexing assembly is depicted in FIGS. 14A-15B. As shown, the indexing assembly 350 can be at least partially positioned within the liquid bath 305 and configured to receive a single corn kernel (optionally, from the singulation assembly 310, 330) and to transport the single corn kernel to the belt assembly 380 in a desired orientation. In exemplary aspects, the indexing assembly 350 can have an inlet 351 that is positioned in fluid communication with the outlet 325, 340 of the singulation assembly 310, 330.

In exemplary aspects, the indexing assembly 350 can comprise a wheel 360 having a circumference and being configured for rotation about a rotational axis 363 that is substantially parallel to the transverse axis 304 of the system 300. The wheel 360 can define a plurality of receptacles 362 about its circumference. In one exemplary aspect, each respective receptacle 362 can be configured to receive a single immature corn kernel when the receptacle is at a first rotational position 365a relative to the rotational axis 363. In this aspect, it is contemplated that each receptacle 362 can be configured to permit the corn kernel to exit the receptacle when the receptacle is positioned in a second rotational position 365b relative to the rotational axis. In another exemplary aspect, the first rotational position 365a of the receptacle is proximate the inlet 351 of the indexing assembly 350, and the second rotational position 365b of the receptacle is within the liquid bath 305.

In an additional aspect, the indexing assembly 350 can comprise a wheel actuator/drive shaft 361 that is operatively coupled to the wheel. In this aspect, the wheel actuator/drive shaft 361 can be configured to effect rotation of the wheel 360 about the rotational axis 363. In exemplary aspects, a portion of the wheel actuator 361 (including all electrical components of the wheel actuator) can be positioned in an operative position within or above housing 308, with the shaft extending through an opening defined by the housing.

In a further aspect, the indexing assembly 350 can further comprise a sensor 352 configured to produce an output indicative of the presence or absence of a corn kernel within the inlet 351 of the indexing assembly. In this aspect, the sensor 352 can be positioned in operative communication with the wheel actuator 361 and configured to communicate the output to the wheel actuator. In response to receiving an output indicative of the presence of a corn kernel at the inlet 351 of the indexing assembly 350, the wheel actuator 361 can be configured to effect rotation of the wheel 360. In exemplary aspects, the sensor 352 can be an optical sensor.

In exemplary aspects, the wheel 360 can comprise first and second outer plates 367a, 367b that are spaced apart relative to the rotational axis 363 (and the transverse axis 304 of the system). In these aspects, the wheel 360 can further comprise a kernel releaser 364 that is positioned between the first and second outer plates and fixedly secured to a frame portion 355 of the wheel. That is, the kernel releaser 364 can be stationary as the wheel 360 rotates relative to the frame 355. The kernel releaser 364 can be secured to the frame of the wheel 360 such that at least a portion of the kernel releaser projects into a receptacle 362 as the receptacle approaches the second rotational position 365b. In use, as the receptacle 362 continues its rotation, the kernel releaser 364 can increasingly project into the receptacle until any kernels within the receptacle (e.g., stuck kernels) are forced out of the receptacle. The presence of the kernel releaser 364 thereby ensures that all kernels exit their receptacle before the receptacle completes a full rotation.

In exemplary aspects, the indexing assembly 350 can further comprise a guard element 366 that is secured to the frame portion 355 of the wheel 360 and radially spaced from the circumference of the wheel 360, with the guard element 366 extending at least partially around the circumference of the wheel. In these aspects, it is contemplated that the guard element 366 can be configured to guide any corn kernel that exits a receptacle during rotation of the wheel. It is contemplated that the guard element can be configured to direct such corn kernel toward the liquid bath, thereby ensuring that no corn kernel is lost or contaminated. Optionally, in exemplary aspects, the indexing assembly 350 can comprise a liquid dispenser (not shown) that is positioned proximate an upper attachment point of the guard element 366, where the guard element is secured to the frame portion of the wheel. In these aspects, the liquid dispenser can be configured to dispense liquid in a downward direction relative to the vertical axis 306 as the wheel 360 rotates. It is contemplated that the liquid dispenser can be positioned such that the liquid dispensed by the dispenser keeps kernels within receptacles when the receptacles are at a rotational position near the top of the wheel and flushes kernels out of their receptacles as they approach the second rotational position 365b. It is further contemplated that the liquid dispensed by the dispenser can help reduce the surface tension of the kernels, causing them to more readily sink within the liquid bath.

In use, once the sensor detects a kernel in a receptacle at the first rotational position, the wheel can be rotated such that the next sequential receptacle is positioned at the first rotational position, thereby permitting entry of the next corn kernel delivered by the singulation assembly. The corn kernel remains with a given receptacle until the receptacle reaches the second rotational position (within the liquid bath), at which point the corn kernel can fall out of the receptacle into the liquid bath.

Thus, in exemplary aspects, and with reference to FIG. 25A, the indexing assembly 350 can be used to sequentially deliver corn kernels to a liquid bath. In one aspect, a method of using the indexing assembly can comprise positioning an immature corn kernel within a receptacle defined about the circumference of the wheel, with the immature corn kernel being positioned within the receptacle when the receptacle is at the first rotational position relative to the rotational axis. In another aspect, the method can comprise rotating the wheel about the rotational axis to position the receptacle at the second rotational position. In the second rotational position, the corn kernel can exit the receptacle into the liquid bath. Optionally, during rotation of the receptacle from the first rotational position to the second rotational position, the receptacle can enter the liquid bath.

2. Kernel Orientation

Figure 15A:
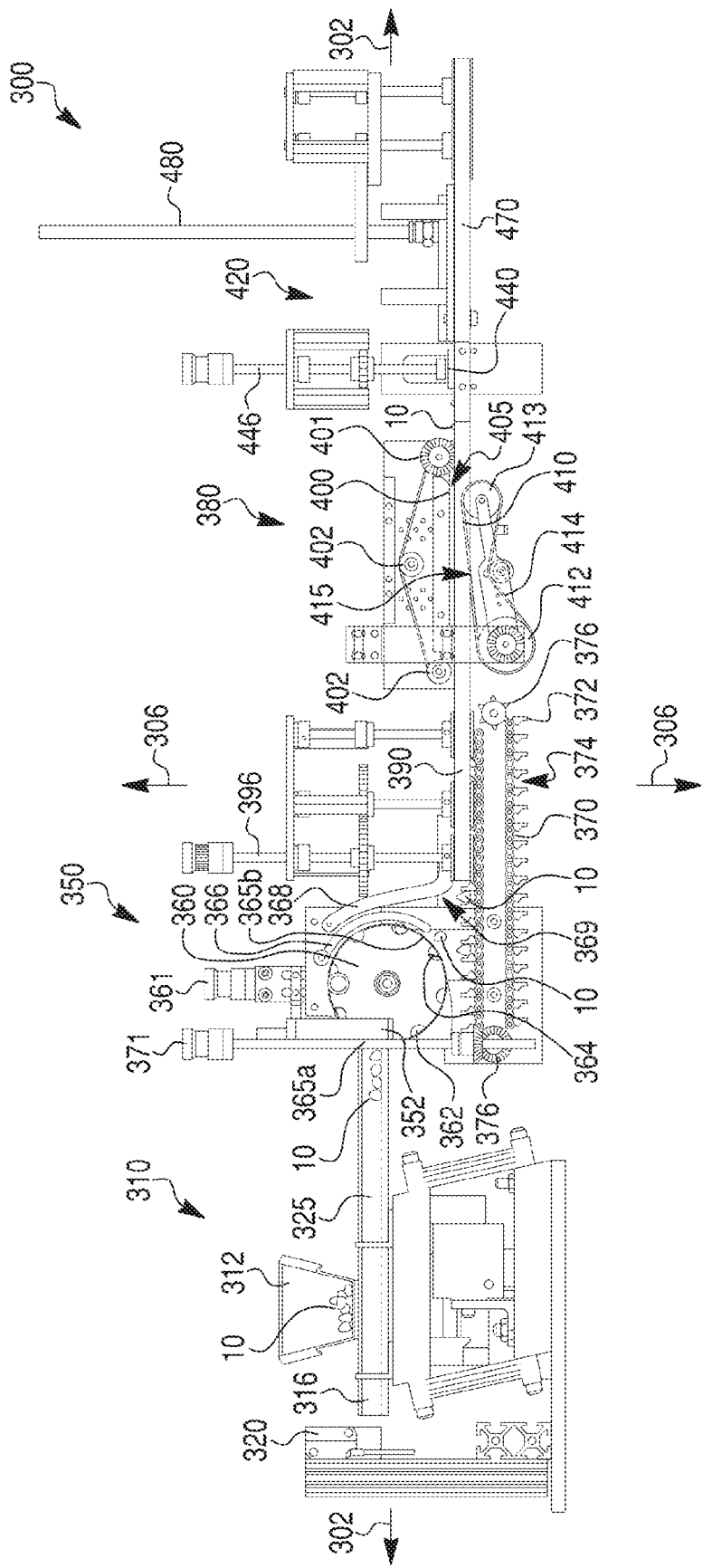
FIG. 15A is an isolated side perspective view of the embryo extraction system of FIG. 14A.
Figure 15B:
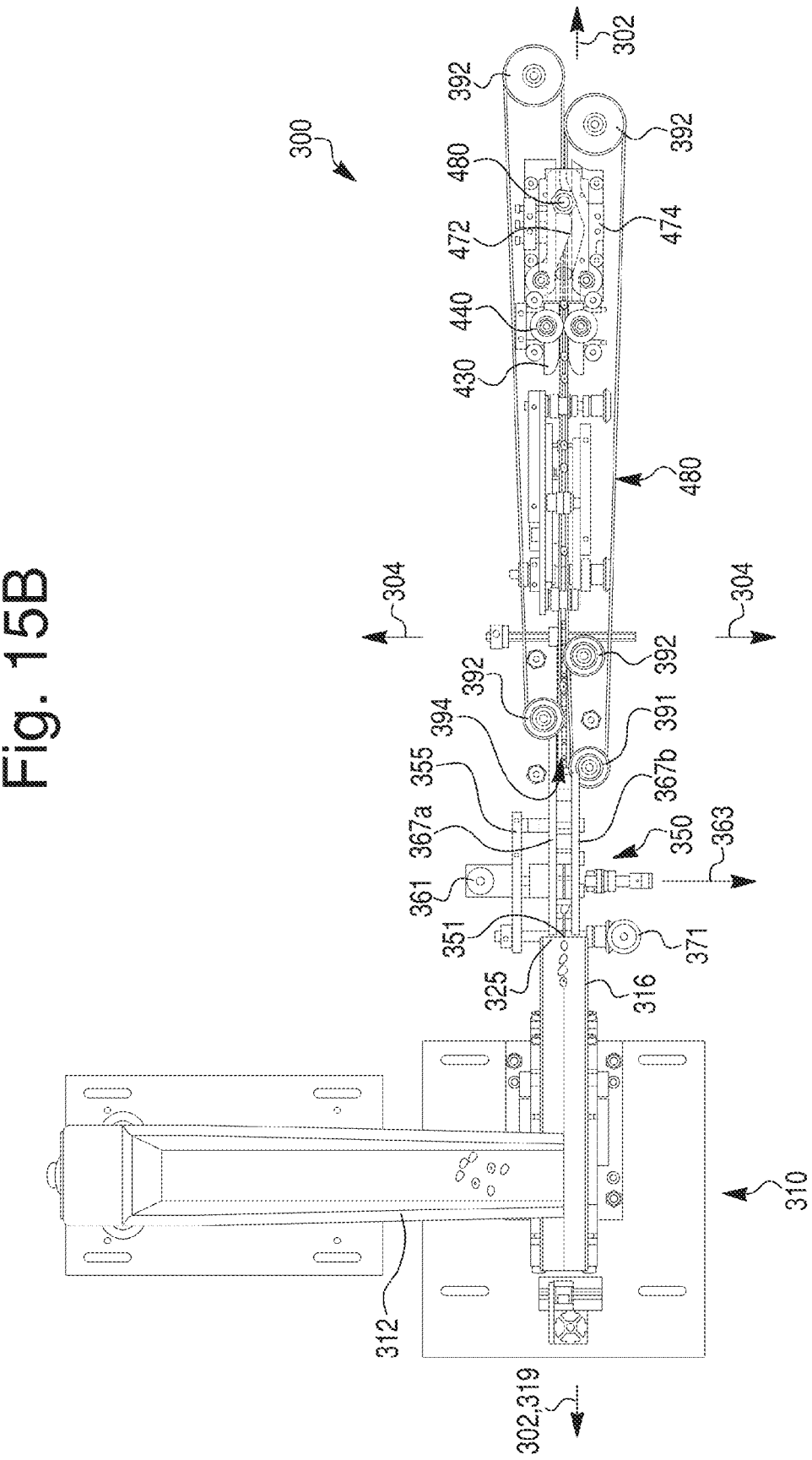
FIG. 15B is an isolated top perspective view of the embryo extraction system of FIG. 14A.
Figure 16A:
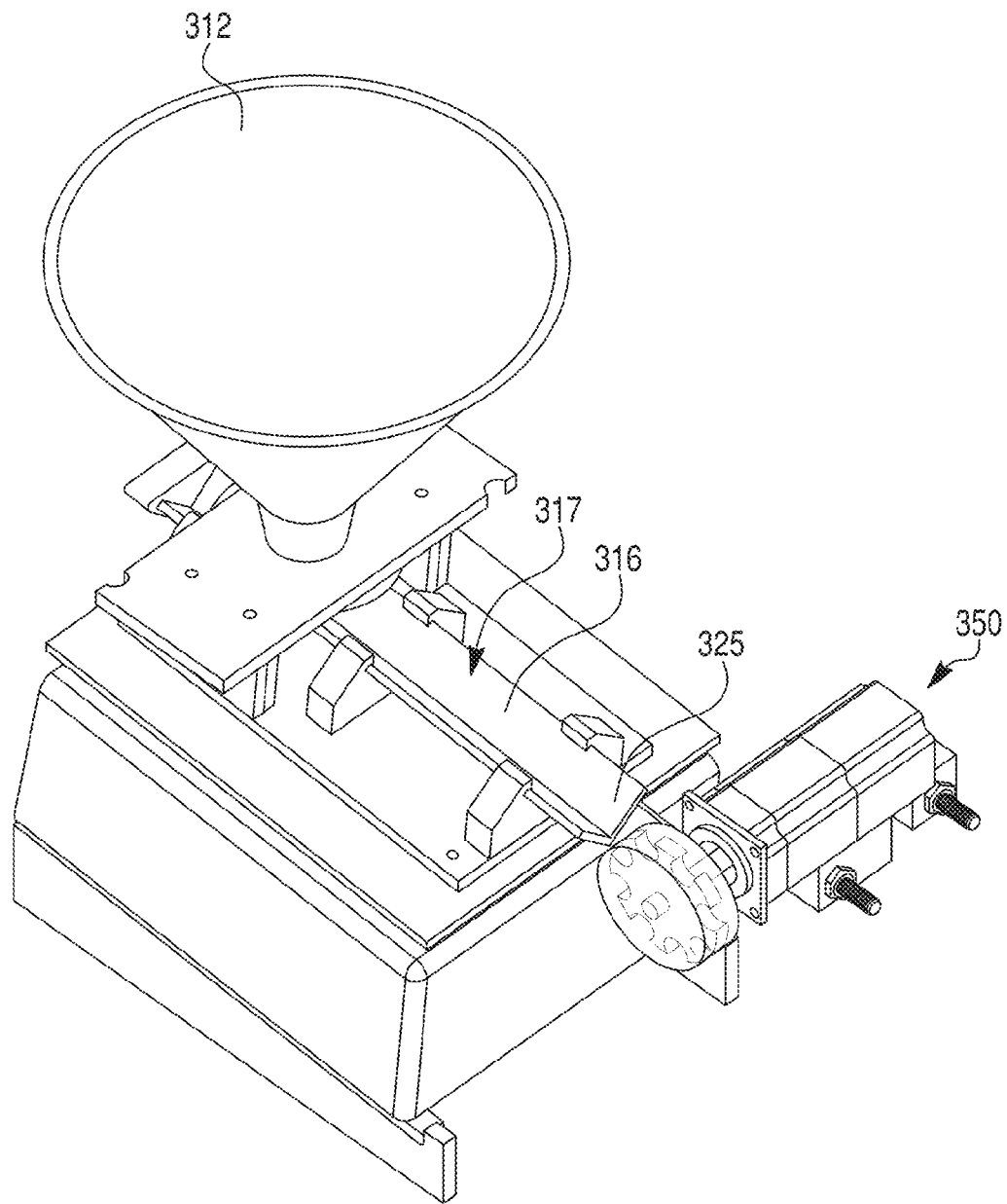
FIG. 16A is a perspective view of an exemplary singulation assembly as disclosed herein.
Figure 16B:
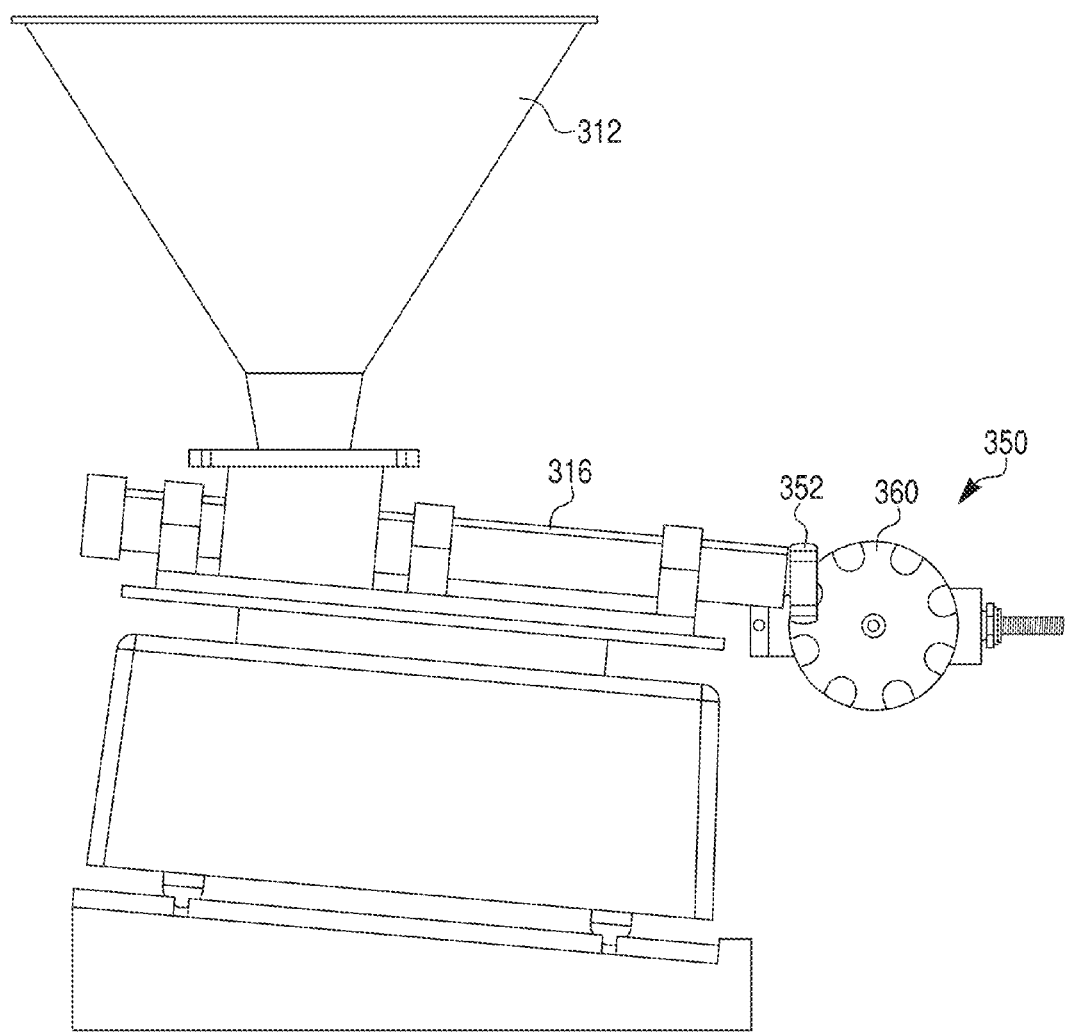
FIG. 16B is a side perspective view of the singulation assembly of FIG. 16A.

In exemplary aspects, as shown in FIGS. 15A-15B, the indexing assembly 350 can further comprise a feed chain 370 positioned within the liquid bath 305 and defining a plurality of receptacles 374. In these aspects, the feed chain 370 can be configured for axial movement relative to the longitudinal axis 302 of the system 300. It is contemplated that each receptacle of the feed chain 370 can be configured to receive a single corn kernel and transport the corn kernel relative to the longitudinal axis 302 of the system 300.

In exemplary aspects, the receptacles 374 can be defined by a plurality of spaced paddles 372 that are secured to and project outwardly from the chain 370. In further exemplary aspects, the chain 370 can be operatively coupled to wheels 376, which, in turn, are operatively coupled to a drive shaft/actuator 371 that is configured to effect movement of the chain. In these aspects, it is contemplated that a portion of the drive shaft/actuator 371 (including all electrical components of the actuator) can be positioned in an operative position within or above housing 308, with the shaft extending through an opening defined by the housing.

In further exemplary aspects, and with reference to FIG. 15A, the wheel 360 of the indexing assembly can further comprise a kernel sinker 368 that is secured to a frame portion of the wheel and radially spaced from the circumference of the wheel. The kernel sinker 368 can define a guide surface 369 that is spaced a selected distance above the chain 370 relative to the vertical axis 306. In one aspect, the guide surface 369 can be configured to ensure that no floating kernels are allowed to enter into the belt transport assembly as further disclosed herein; in other words, the guide surface 369 is positioned and shaped to force (e.g., knock down) any semi-buoyant corn kernel to enter a respective receptacle 374.

Figure 19:
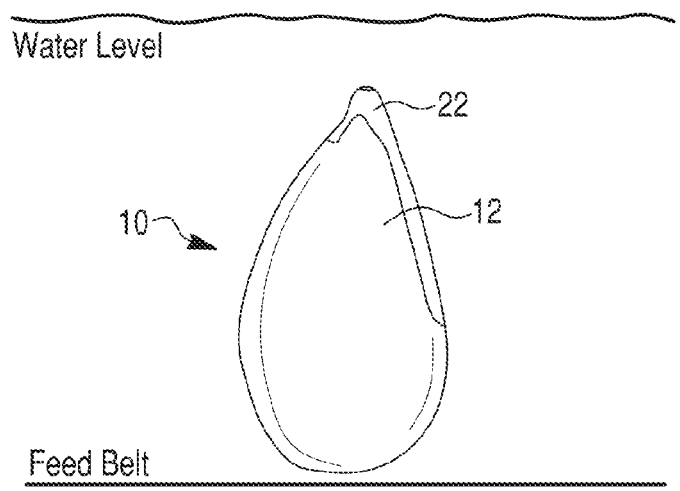
FIG. 19 is a schematic diagram depicting the orientation of a corn kernel within a liquid bath as disclosed herein.
Figure 20:
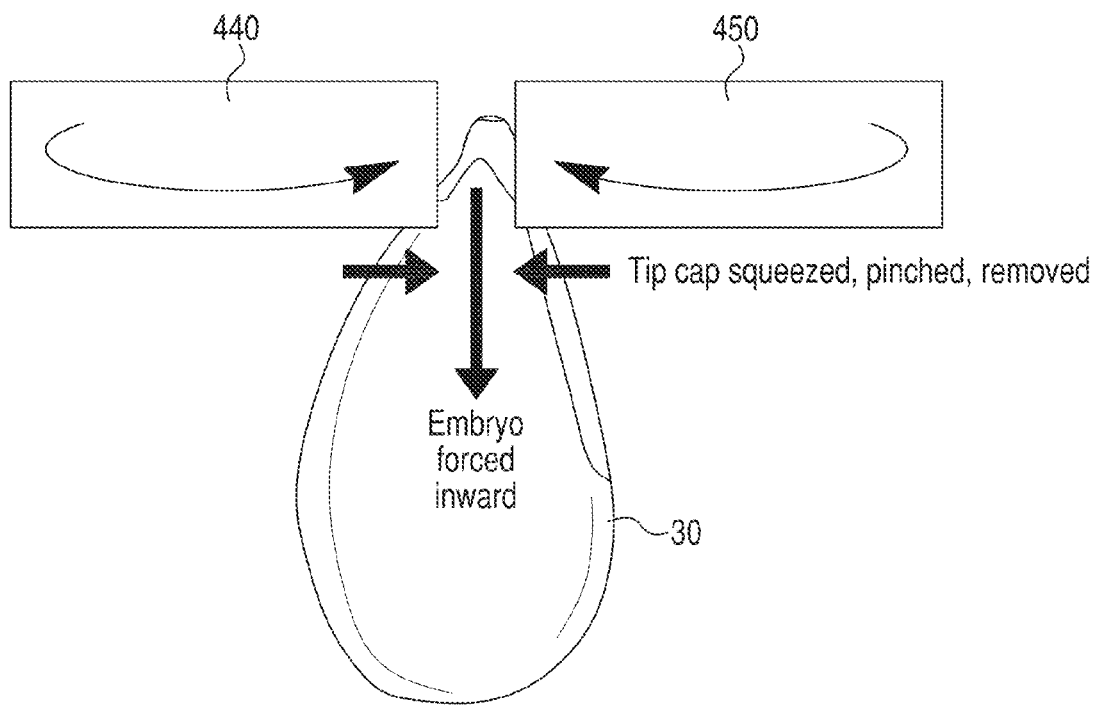
FIG. 20 is a schematic diagram depicting an exemplary force application assembly of the embryo extraction system applying force to a corn kernel as disclosed herein.

In exemplary aspects, and with reference to FIG. 19, it is contemplated that the fluid within the fluid bath can cause the kernels within the liquid bath to sink with their tips upward so that the receptacles 374 of the chain 370 receive the kernels in this orientation. Thus, in exemplary aspects, the desired orientation can be an orientation in which the tip caps of the kernels are oriented in an upward direction relative to the vertical axis 306.

In exemplary aspects, and with reference to FIG. 25A, a method of using the indexing assembly 350 can comprise receiving a corn kernel within a receptacle defined by the feed chain, with the feed chain positioned within the liquid bath. In another aspect, the method can comprise effecting axial movement of the feed chain relative to the longitudinal axis 302 of the system 300 to transport the corn kernel relative to the longitudinal axis.

3. Belt Transport

In exemplary aspects, the belt assembly 380 can be positioned within the liquid bath 305 and configured to sequentially advance a plurality of corn kernels relative to the longitudinal axis 302 of the system 300.

In one exemplary aspect, the belt assembly 380 can comprise first and second side transport belts 390a, 390b that are spaced apart relative to the transverse axis 304 of the system 300 to define a transport channel 394 that extends substantially parallel to the longitudinal axis 302 of the system. In this aspect, the transport channel 394 can be positioned in communication with the feed chain 370 and configured to receive a corn kernel from a receptacle 374 of the feed chain. In another aspect, the first and second side transport belts 390a, 390b can be configured to drive movement of the corn kernel relative to the longitudinal axis 302 of the system 300. In exemplary aspects, the side transport belts 390a, 390b can comprise urethane. However, it is contemplated that any material capable of engaging and driving axial movement of a kernel as disclosed herein can be used.

In exemplary aspects, the belt assembly 380 can further comprise a ceiling belt 400 positioned above the transport channel 394 relative to the vertical axis 306. In these aspects, the ceiling belt 400 can have a lower surface 405 that has a consistent height relative to the vertical axis 306. In additional aspects, the belt assembly can further comprise a lifter belt 410 positioned below the transport channel 394 and the ceiling belt 400 relative to the vertical axis 306. That is, the transport channel 394 can be positioned between the ceiling belt 400 and the lifter belt 410 relative to the vertical axis 306. In these aspects, the lifter belt can have an upper surface 415 that is configured to engage a corn kernel within the transport channel 394 and drive upward movement of the corn kernel relative to the vertical axis 306 until the corn kernel contacts the lower surface 405 of the ceiling belt 400.

In exemplary aspects, the side transport belts 390a, 390b can be operatively coupled to an actuator (not shown) through a combination of wheels 391 and/or pulleys 392, which are operatively coupled to drive shaft 396 to impart movement to the belts. In further exemplary aspects, the ceiling belt 400 can be operatively coupled to an actuator (not shown) through wheel 401 and pulley 402, which are operatively coupled to a drive shaft 404 to impart movement to the ceiling belt. In still further exemplary aspects, the lifter belt 410 can be operatively coupled to an actuator (not shown) through wheel 412 and pulley 413, which are operatively coupled to a drive shaft 416 to impart movement to the lifter belt. In exemplary aspects, the lifter belt 410 can comprise a lifter arm 414 that extends between and is coupled to the wheel 412 and the pulley 413. In exemplary aspects, at least a portion of the drive shafts 396, 404, 416 and their associated actuators (not shown), including all electrical components of the actuators, can be positioned in an operative position within or above housing 308, with the shafts extending through corresponding openings defined by the housing.

In operation, after a kernel is pulled into the side transport belts, the belt lifter can make contact with the bottom of the kernel. The kernel can then be lifted to make contact with the ceiling belt. In this aspect, the kernels can continue to move with the side transport belts and can enter the force application assembly 420 at a consistent tip height.

Thus, in exemplary aspects, and with reference to FIG. 25A, a method of using the belt assembly 380 can comprise delivering an immature corn kernel from a receptacle of the feed chain to the transport channel. In these aspects, the method can further comprise driving movement of the immature corn kernel relative to the longitudinal axis using the side transport belts of the belt assembly. In another aspect, the method can further comprise using the lifter belt to engage the immature corn kernel within the transport channel and drive upward movement of the corn kernel relative to the vertical axis until the corn kernel contacts the lower surface of the ceiling belt.

4. Tip Cap Removal

In exemplary aspects, and with reference to FIGS. 14A-15B, 18A-18D, and 20, the force application assembly 420 can optionally be positioned within the liquid bath 305. In other aspects, it is contemplated that the force application assembly 420 can be operated in dry conditions, external or separate from the liquid bath. In one aspect, the force application assembly 420 can comprise a kernel stabilizing portion 430 that defines a receiving channel 436 that is configured to receive and support an individual corn kernel in a desired position as the corn kernel is advanced relative to the longitudinal axis 302 of the system 300. In the desired position, it is contemplated that at least a portion of a proximal end of the corn kernel extends upwardly from the kernel stabilizing portion 430 relative to the vertical axis 306. In a further aspect, the cutting assembly 420 can comprise at least one wheel 440 operatively positioned relative to (e.g., operatively positioned above) the kernel stabilizing portion 430, with the at least one wheel 440 optionally being coupled to the kernel stabilizing portion 430. In this aspect, the at least one wheel 440 can be selectively rotatable to apply a force to the proximal end of the corn kernel as the corn kernel is advanced through the receiving channel 436 of the kernel stabilizing portion 430 relative to the longitudinal axis 302 of the system 300. It is contemplated that the force applied by the at least one wheel 440 can be at least one of a squeezing force, a pinching force, a crushing force, a cutting force, a ripping force, or a tearing force. In exemplary aspects, the kernel stabilizing portion 430 can have a first arm 432 and a second arm 434 that are spaced apart relative to the transverse axis 304 and that cooperate to define the receiving channel 436.

In one exemplary aspect, and as shown in FIG. 18B-18C, the at least one wheel 440 of the force application assembly comprises first and second wheels 440, 450 positioned on opposing sides of the receiving channel 436 of the kernel stabilizing portion 430. Optionally, in this aspect, and as shown in FIG. 18B, the first and second wheels 440, 450 can comprise first and second wheels having respective opposing geared surfaces, which can optionally comprise rubber (e.g., neoprene rubber). Optionally, it is contemplated that the first wheel 440 can be configured for rotation in a first direction about its rotational axis, while the second wheel 450 can be configured for rotation in a second direction opposite the first direction such that the first and second wheels 440, 450 counter-rotate relative to one another. It is further contemplated that, within the receiving channel 436, the opposing first and second directions of rotation can generally correspond to rotation of the first and second wheels 440, 450 toward the squeezing portion 470 of the force application assembly. In further exemplary aspects, at least a portion of an outer surface of the first wheel 440 can be configured to contact a portion of an outer surface of the second wheel 450 as the two wheels rotate in opposing directions.

Figure 18A:
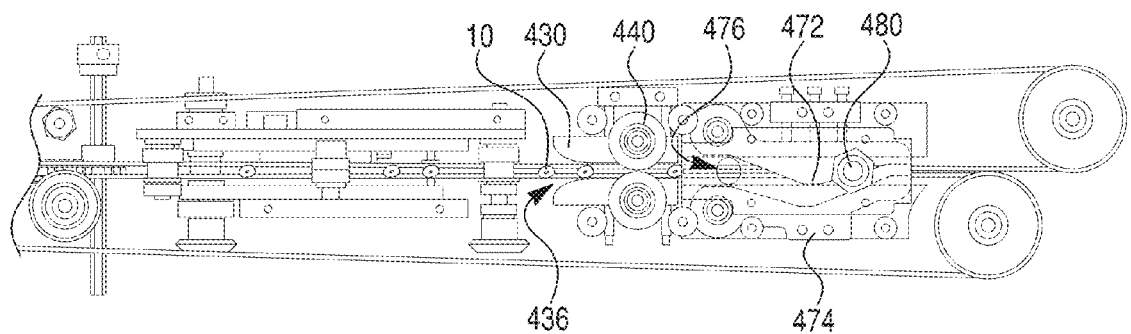
FIG. 18A is an isolated top view of an exemplary force application assembly of the embryo extraction system of FIG. 14A.
Figure 18D:
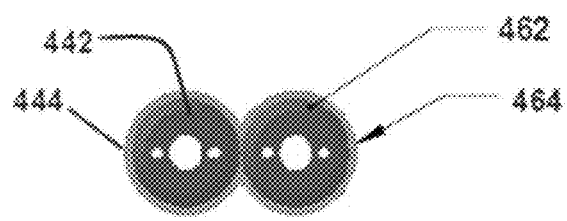
FIG. 18D is a bottom perspective view of the first and second wheels of FIG. 18C.

Optionally, in an alternative aspect, and as shown in FIGS. 18C-18D, the first and second wheels 440, 450 can have respective base portions 444, 464 (e.g., rubber base portions) and cutting portions 442, 462. In this aspect, the cutting portion 442, 462 of each respective wheel 440, 450 can be positioned below the base portion 444, 464 of the wheel relative to the vertical axis 306. As shown in FIG. 18D, it is contemplated that the cutting portion 442, 462 of each respective wheel 440, 450 can define a circumferential blade. Optionally, it is contemplated that the first wheel 440 can be configured for rotation in a first direction about its rotational axis, while the second wheel 450 can be configured for rotation in a second direction opposite the first direction such that the first and second wheels 440, 450 counter-rotate relative to one another. It is further contemplated that, within the receiving channel 436, the opposing first and second directions of rotation can generally correspond to rotation of the first and second wheels 440, 450 toward the squeezing portion 470 of the force application assembly. Optionally, in further exemplary aspects, at least a portion of an outer surface of the rubber base portion 444 of the first wheel 440 can be configured to contact a portion of an outer surface of the rubber base portion 464 of the second wheel 450 as the two wheels rotate in opposing directions.

In a further alternative aspect, and as shown in FIG. 18E, the at least one wheel of the force application assembly 420 can comprise a single wheel 440. In this aspect, it is contemplated that the wheel 440 can have a diameter that extends over the receiving channel 436 relative to the transverse axis 304. It is further contemplated that the increased diameter of the wheel can be configured to apply a lateral pushing force to the tip cap of the kernel, thereby tearing a portion of the tip cap from the kernel. Optionally, it is contemplated that the single wheel 440 can have a geared surface.

In exemplary aspects, the disclosed remover wheels 440, 450 can be operatively coupled to drive shafts 446, 452, which are in turn coupled to actuators that are configured to effect selective rotational movement of the wheels. In these aspects, a portion of the drive shafts 446, 452 and their associated actuators (including all electrical components of the actuators) can be positioned in an operative position within or above housing 308, with the shafts extending through corresponding openings defined by the housing.

In one aspect, it is contemplated that the tip of each kernel can approach the squeezing portion 470 of the force application assembly 420 at a consistent height relative to the vertical axis. In exemplary aspects, the at least one wheel 440, 450 can rotate at a fixed height, in substantial alignment with the tip caps of the approaching kernels. It is contemplated that as the kernel begins to contact the removal wheels, the embryo can be pushed deeper into the kernel (away from the tip cap). It is further contemplated that the kernel can continue to move through the removal wheels relative to the longitudinal axis of the system, and force (e.g., tearing, pinching, cutting, crushing, ripping, squeezing) can be applied to the tip cap to form the hole or opening. Optionally, the application of force can remove at least a portion of the tip cap from the kernel, and the removed portion of the tip cap can then be flushed and/or vacuumed away.

Figure 25B:
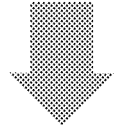
FIG. 25B is a flowchart depicting an exemplary method of removing at least a portion of the proximal end of a corn kernel to form an opening in the corn kernel, as disclosed herein.

In exemplary aspects, and with reference to FIG. 25B, a method of using the force application assembly 420 can comprise positioning an individual corn kernel within the receiving channel defined by the kernel stabilizing portion. In these aspects, the kernel stabilizing portion can support the corn kernel in a desired position as the corn kernel is advanced relative to a longitudinal axis. In the desired position, at least a portion of the proximal end of the corn kernel can extend upwardly from the kernel stabilizing portion relative to the vertical axis. In another aspect, the method can further comprise rotating at least one wheel to apply a force to the proximal end of the corn kernel as the corn kernel is advanced through the receiving channel of the kernel stabilizing portion relative to the longitudinal axis.

5. Kernel Squeezing and Embryo Collection

In exemplary aspects, and with reference to FIGS. 14A-15B and 18A-18E, the force application assembly 420 can further comprise a squeezing portion 470 having first and second opposed squeeze bars 472, 474 that are spaced apart relative to the transverse axis 304. In these aspects, the opposed squeeze bars 472, 474 can cooperate to define a channel 476 that is configured to receive a corn kernel from the kernel stabilizing portion 430 as the corn kernel is advanced relative to the longitudinal axis 302 of the system 300. In exemplary aspects, the squeeze bars 472, 474 can optionally be positioned radially outwardly of the side transport belts 390a, 390b of the belt assembly 380 (relative to the longitudinal axis 302), and the squeeze bars 472, 474 can cooperate with the side transport belts to define the channel 476. In these aspects, it is contemplated that the shape and profile of the side transport belts 390a, 390b relative to the longitudinal axis 302 of the system 300 can conform to the profile defined by the respective squeeze bars 472, 474, as further disclosed herein. In exemplary aspects, it is contemplated that at least a portion of the squeeze bars 472, 474 can project over the side transport belts 390a, 390b. Optionally, it is contemplated that the squeeze bars 472, 474 can comprise plastic or other acrylic materials; however, it is contemplated that any suitable material capable of applying a squeezing force as disclosed herein can be used.

In one aspect, at least one of the opposed squeeze bars 472, 474 is biased toward the other squeeze bar relative to the transverse axis 304. Optionally, in this aspect, it is contemplated that both the squeeze bars 472, 474 can be biased toward one another. Any conventional biasing means can be used; however, in exemplary aspects, at least one of the squeeze bars 472, 474 can be spring-loaded toward the other squeeze bar. In operation, the opposed squeeze bars 472, 474 can be configured to apply a radial squeezing force to the corn kernel as it moves through the channel 476 of the squeezing portion 470 relative to the longitudinal axis 302.

Although disclosed herein as being biased radially inwardly, it is contemplated that other means for effecting radial movement of the squeeze bars can be employed. For example, it is contemplated that at least one squeeze bar 472, 474 can be operatively coupled to an actuator that is configured to effect movement of the squeeze bar toward the other squeeze bar.

In exemplary aspects, the system 300 can further comprise an embryo collection tube 480 that is positioned in fluid communication with the liquid bath 305 and configured to receive liquid containing an embryo extracted from a corn kernel in response to application of the radial squeezing force by the squeezing portion 470 of the system.

In one exemplary aspect, the first squeeze bar 472 of the squeezing portion 470 can be biased inwardly toward the second squeeze bar 474, and the second squeeze bar can have a fixed position. Optionally, in this aspect, the first squeeze bar 472 can have a convex profile relative to the longitudinal axis 302 of the system 300, and the second squeeze bar 474 can have a concave profile relative to the longitudinal axis of the system. It is contemplated that this profile can apply radial force to the seed in different directions to force the embryo to exit the seed. In further exemplary aspects, it is contemplated that at least one of the first squeeze bar 472 and the second squeeze bar 474 can have a consistent arcuate profile relative to the longitudinal axis 302 of the system 300. For example, the first squeeze bar 472 can optionally have a convex, consistent arcuate profile, while the second squeeze bar 474 can optionally have a concave, consistent arcuate profile. Alternatively, the first squeeze bar 472 can have a convex, consistent arcuate profile, while the second squeeze bar 474 can have a smooth (straight) profile. In still further exemplary aspects, it is contemplated that at least one of the first squeeze bar 472 and the second squeeze bar 474 can have a wavy profile that varies relative to the longitudinal axis 302 of the system 300. For example, the first squeeze bar 472 can optionally have a first wavy profile that is substantially complementary to a second wavy profile of the second squeeze bar 474. Alternatively, the first squeeze bar 472 can have a wavy profile, while the second squeeze bar 474 can have a consistent arcuate profile or a smooth (straight) profile.

In an exemplary aspect, it is contemplated that a de-capped kernel that exits the wheels 440, 450 can continue to move toward the squeezing portion 470 relative to the longitudinal axis 302. In this aspect, the squeezing portion 470 (first and second squeeze bars 472, 474) can gradually apply increasing pressure to the sides of the kernel through the side belts 390a, 390b. The embryo can then be released from the kernel, and the embryo can be captured by a flow of liquid into the embryo collection tube 480. The remaining kernel material can continue to move with the side belts 390a, 390b until it reaches a waste collection basket 490. The embryo can be carried via liquid flow through the embryo collection tube 480 to a collection container. Once the embryo reaches the collection container, the embryo can be plated onto a Petri dish or otherwise prepared for further processing.

In exemplary aspects, and with reference to FIG. 25C, a method of using the force application assembly 420 can comprise delivering an immature corn kernel from the kernel stabilizing portion to the channel defined by the opposed squeeze bars as the corn kernel is advanced relative to the longitudinal axis. In another aspect, the method can comprise using the opposed squeeze bars to apply a radial squeezing force to the immature corn kernel as it moves through the channel of the squeezing portion relative to the longitudinal axis. In a further aspect, the method can comprise positioning the embryo collection tube in fluid communication with the liquid bath. Following extraction of the embryo from the immature corn kernel in response to application of the radial squeezing force by the opposed squeeze bars, liquid flow can be used to transport the embryo through the embryo collection tube.

ii. Automated Extraction Device

Figure 21A:
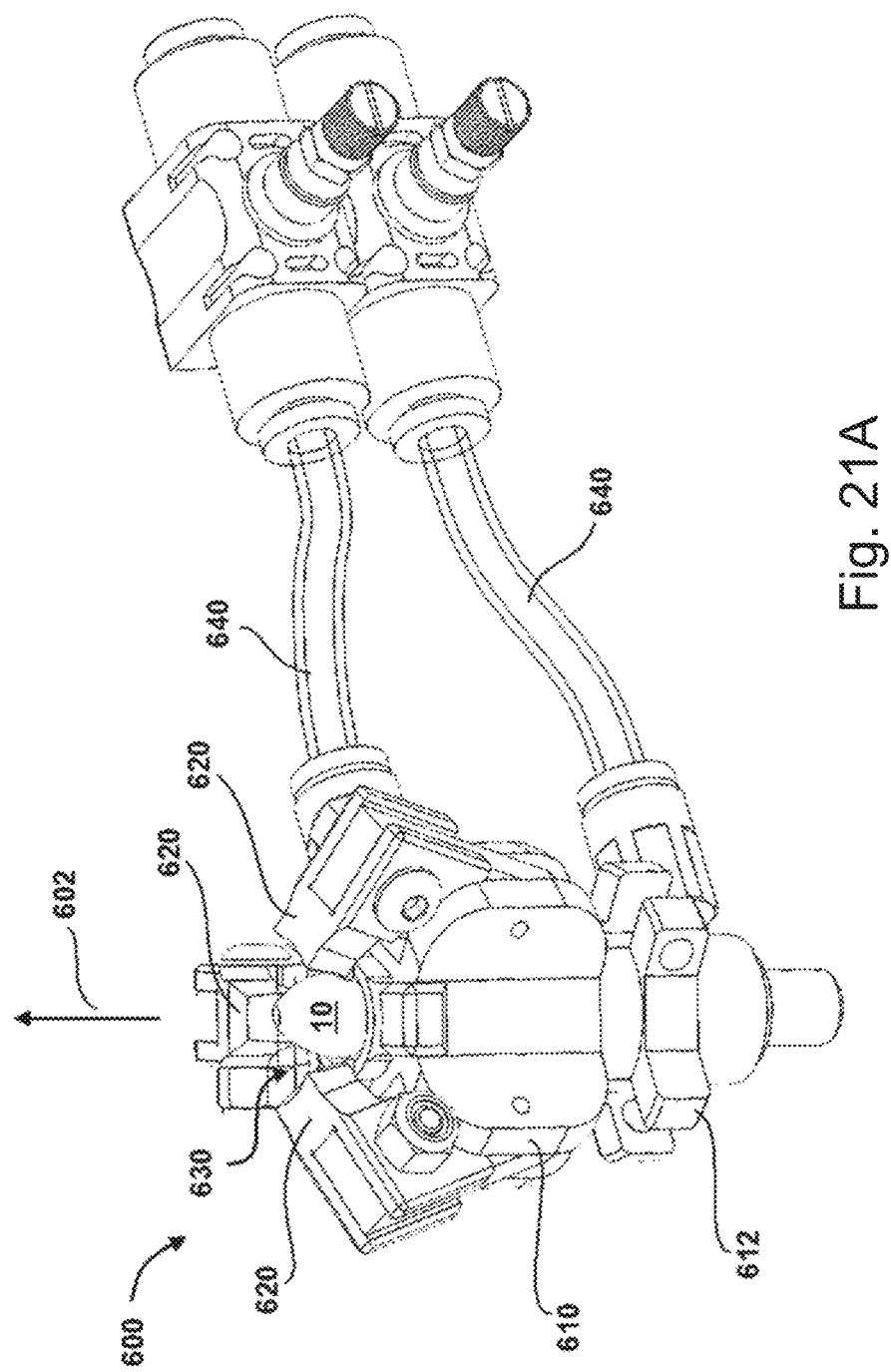
FIG. 21A is a perspective view of an automated extraction device as disclosed herein.
Figure 21B:
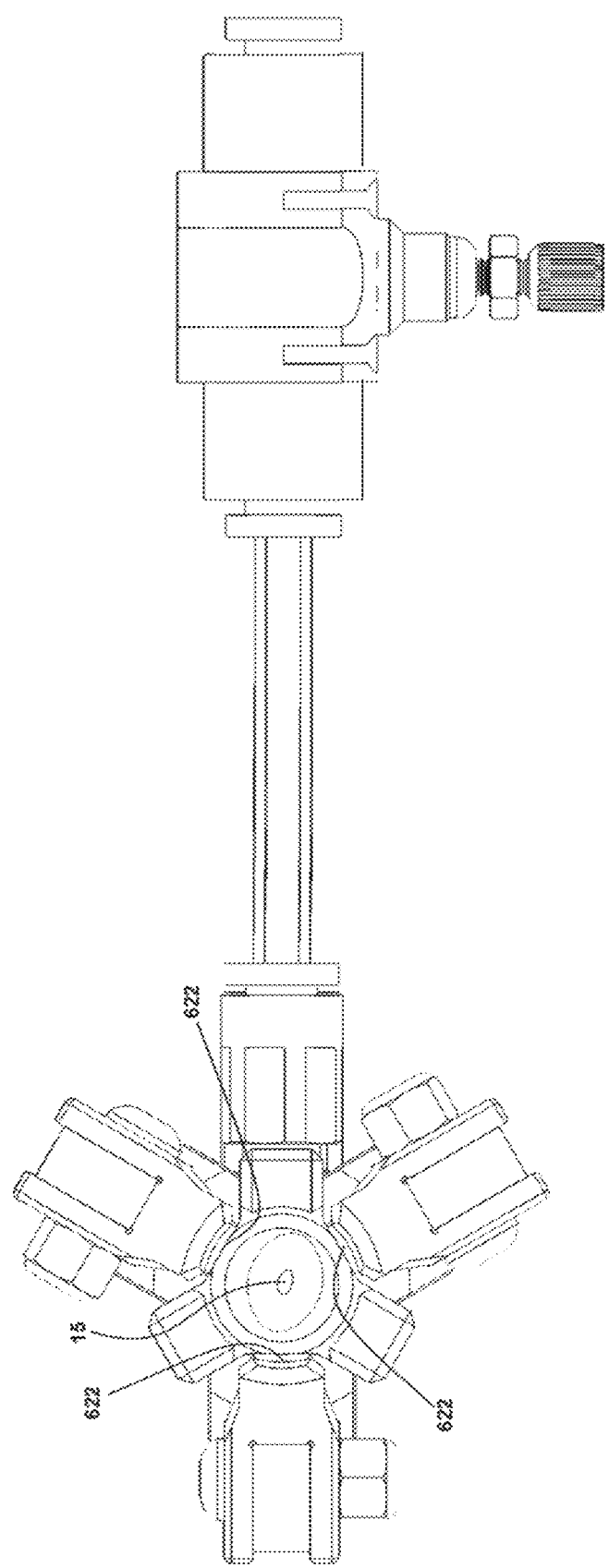
FIG. 21B is a top view of the automated extraction device of FIG. 21A.

In an exemplary aspect, and as shown in FIGS. 21A-21B, an automated extraction device 600 for extracting a corn embryo from a corn kernel is provided. In this aspect, it is contemplated that the automated extraction device 600 can be provided as part of an automated embryo extraction system. However, it is further contemplated that the automated extraction device 600 can be used independently in a manual process in which individual corn kernels are selectively positioned within the extraction device. In one aspect, the extraction device 600 can have a support base 610 operatively coupled to a bottom portion 612 of the device. The support base 610 can be configured to support a corn kernel in a desired orientation as disclosed herein. The extraction device 600 can further comprise a plurality of circumferentially spaced fingers 620 that cooperate with the support base 610 to define a central receiving space 630 for receiving a corn kernel. The plurality of circumferentially spaced fingers 620 can have respective gripping surfaces 622 that are oriented toward a central axis 602 of the device 600 that is substantially aligned with a center point 15 of the corn kernel 10. The plurality of circumferentially spaced fingers 620 can be configured for selective radial movement between an open position and a gripping position. The plurality of circumferentially spaced fingers 620, through their gripping surfaces 622, can be configured to selectively apply a radial force to the corn kernel 10. In exemplary aspects, the plurality of fingers 620 can be configured to apply a force of a first magnitude sufficient to support the corn kernel during formation of an opening or hole in the corn kernel 10 as disclosed herein. In these aspects, the plurality of fingers 620 can be further configured to apply a second force of a second magnitude sufficient to force the corn embryo of the corn kernel through the hole of the corn kernel without damaging the embryo. It is contemplated that the plurality of fingers 620 can optionally be activated using pneumatic means, such as, for example and without limitation, pneumatic hoses 640. In exemplary aspects, the plurality of fingers 620 can comprise three fingers. Generally, it is contemplated that an odd number of gripping surfaces 622 can provide advantageous centering. It is further contemplated that angling of the fingers 620 as shown can produce an advantageous in-and-down squeezing profile (relative to a vertical axis). In exemplary aspects, the plurality of fingers 620 can be configured to apply a radial extraction force in a pulsed manner. It is still further contemplated that gripping surfaces 622 of the fingers 620 can have a curvature that generally matches the curvature of a corn kernel. In further exemplary aspects, it is contemplated that the automated extraction device 600 can comprise a 3-jaw robotic manipulator, with each jaw being coupled to a respective finger 620 and the support base 610 being mounted to a top surface of the robotic manipulator. In still further exemplary aspects, it is contemplated that the automated extraction device 600 can be configured for underwater usage. Alternatively, the automated extraction device 600 can be positioned above a liquid bath such that an embryo exiting a kernel within the extraction device is received within the liquid bath.

d. Monocot Embryo Transport Assembly

Following extraction of a monocot embryo from a monocot seed as disclosed herein, the monocot embryo can be collected from a container, such as, for example and without limitation, a container containing a liquid bath as described herein. It is contemplated that the monocot embryo can be collected by any mechanical means that avoids damage to the monocot embryo. In exemplary aspects, it is contemplated that the monocot embryo can be collected through a tube positioned in fluid communication with the container. In these aspects, it is contemplated that the tube can be configured to sequentially receive individual monocot embryos and transport the monocot embryos to at least one selected receptacle. Optionally, in additional exemplary aspects, it is contemplated that the tube and the at least one selected receptacle can be operatively coupled to a positive pressure source or a negative pressure source, such as, for example and without limitation, a suction pump as is known in the art.

e. Analysis Systems

In exemplary aspects, it is contemplated that the analysis steps of the disclosed methods can be performed using conventional genetic analysis equipment, conventional chemical analysis equipment, and/or conventional spectral analysis equipment, and/or automated systems combining any number of these steps, including, for example and without limitation, extraction, dilution, and the like.

The following examples are offered by way of illustration and not by way of limitation.

EXPERIMENTAL

Example 1

Comparison of the Condition and Quality of immature Corn Embryos Extracted Using Five Different Methods Immature corn embryos were extracted using five different methods: hand extraction; high-pressure water; suction; hand squeezing; and semi-automated squeezing. The condition and quality of extracted embryos was evaluated for each respective method.

One ear of immature corn was used for each extraction method. The embryos were 2.0-3.5 mm long and were extracted 12-18 days post-pollination (corresponding to 340-380 Growing Degree Units (GDUs)). The embryos were substantially the same size as those used in typical Doubled Haploid production methods.

a. Sterilization and Cleaning

Initially, the husks and silks were removed from four ears of immature corn. After removal of the husks and silks, each ear was secured to an ear holder. The ears were then positioned within an empty pitcher. The pitcher was then filled with a solution containing 20%-50% CLOROX Bleach, one drop of TWEEN® 20, and tap water. The ears were soaked in the sterilizing solution, with the ears being rotated occasionally using the ear holders. After 15-20 minutes of soaking, the ears were removed from solution and then rinsed three times with tap water.

b. Seed Preparation

For the hand, high-pressure water, and suction extraction methods, the ear was held using the ear holder, and a scalpel was used to slice off the kernel caps of each corn kernel on the ear.

For the hand-squeezing extraction method, the ear was held using the ear holder, and a fingertip was used to remove whole seeds from the cob. A scalpel was then used to slice off the individual kernel tips of the seeds.

For the semi-automated squeezing extraction method, the ear was held using the ear holder, and a fingertip was used to remove whole seeds from the cob.

c. Embryo Extraction

For the hand extraction method, a spatula was used to remove 30 embryos from an ear (with the seed caps removed).

For the high-pressure water extraction method, an ear (with the seed caps removed) was selectively positioned, and a hand-pressure nozzle was used to wash the embryos out of the seeds and into catch pans (dishes). Tap water was used to wash the embryo debris through mesh sieves of decreasing size until the embryos could be clearly identified. A spatula was used to remove 30 embryos from the sieve.

For the vacuum extraction method, a vacuum pump was used to remove embryos from an ear (with the seed caps removed) via tubing. The tubing was positioned in fluid communication with an Erlenmeyer flask such that the extracted embryos were delivered to the flask. The embryos within the flask were washed with tap water through mesh sieves of decreasing size to separate the embryos from embryo debris until the embryos could be clearly identified. A spatula was used to remove 30 embryos from the sieve.

For the hand-squeezing extraction method, each seed (with its tip removed) was positioned between the thumb and forefinger of an operator, and pressure was gently applied until the embryo popped out of the seed into a clean container. A spatula was used to remove 30 embryos from the container.

For the semi-automated squeezing extraction method, an automated extraction device as disclosed herein and depicted in FIGS. 21A-21B was set with its fingers in an open position. An individual kernel was positioned within the central receiving space defined between the open fingers and the support base of the extraction device. The kernel was positioned with its tip facing up, and the fingers of the extraction device were advanced to a gripping position to hold the kernel in the desired orientation. In a first trial, a scalpel was used to remove a portion of the tips of some kernels (without damaging the embryo) while the kernels were gripped by the fingers of the extraction device, while the tips of other kernels were removed prior to positioning of the kernels within the extraction device. In a second trial, the tips of all kernels were removed prior to positioning of the kernels within the extraction device. With each kernel gripped by the fingers of the extraction device, the fingers were radially advanced to apply an extraction force to the sides of the kernel. The extraction force was pulsed as necessary until the embryo exited the hole formed in the tip of the kernel. The fingers were then returned to the open position, and the extracted embryo was collected. This process was repeated until 30 embryos were extracted and collected.

d. Embryo Plating

Five petri dishes were filled with 605J Resting Media, and one petri dish was filled with 272X Resting Media. With the lid of each petri dish removed, 30 extracted embryos for each respective extraction method were evenly distributed on the resting media (to ensure adequate separation between the embryos) in a corresponding petri dish using a spatula. The embryos extracted using the hand extraction, high-pressure water, suction, and hand-squeezing methods were positioned within the 605J Resting Media, and the embryos extracted using the semi-automated squeezing method were positioned within the 272X Resting Media. The lids were replaced on each petri dish, and a marker was used to label each petri dish in accordance with the method used to extract the embryos within the petri dish and the position of the petri dish relative to the other petri dishes.

e. Embryo Analysis

Each embryo was analyzed under a microscope, and a score of the condition and quality of each embryo was independently recorded by two different analysts. The analysts looked for damage, defects, or other stress issues that may have an adverse effect on the growth and/or vigor of the embryo. Each embryo was rated on a general condition scale of 1-3, with 1=Excellent Condition, 2=Minor Defects or Damage (still capable of normal growth), and 3=Major Defects or Damage (unlikely to grow or grow normally). Any explanations or comments about each embryo's condition or quality were recorded. A digital record of each petri dish and its contents was prepared.

f. Results

Figure 26:
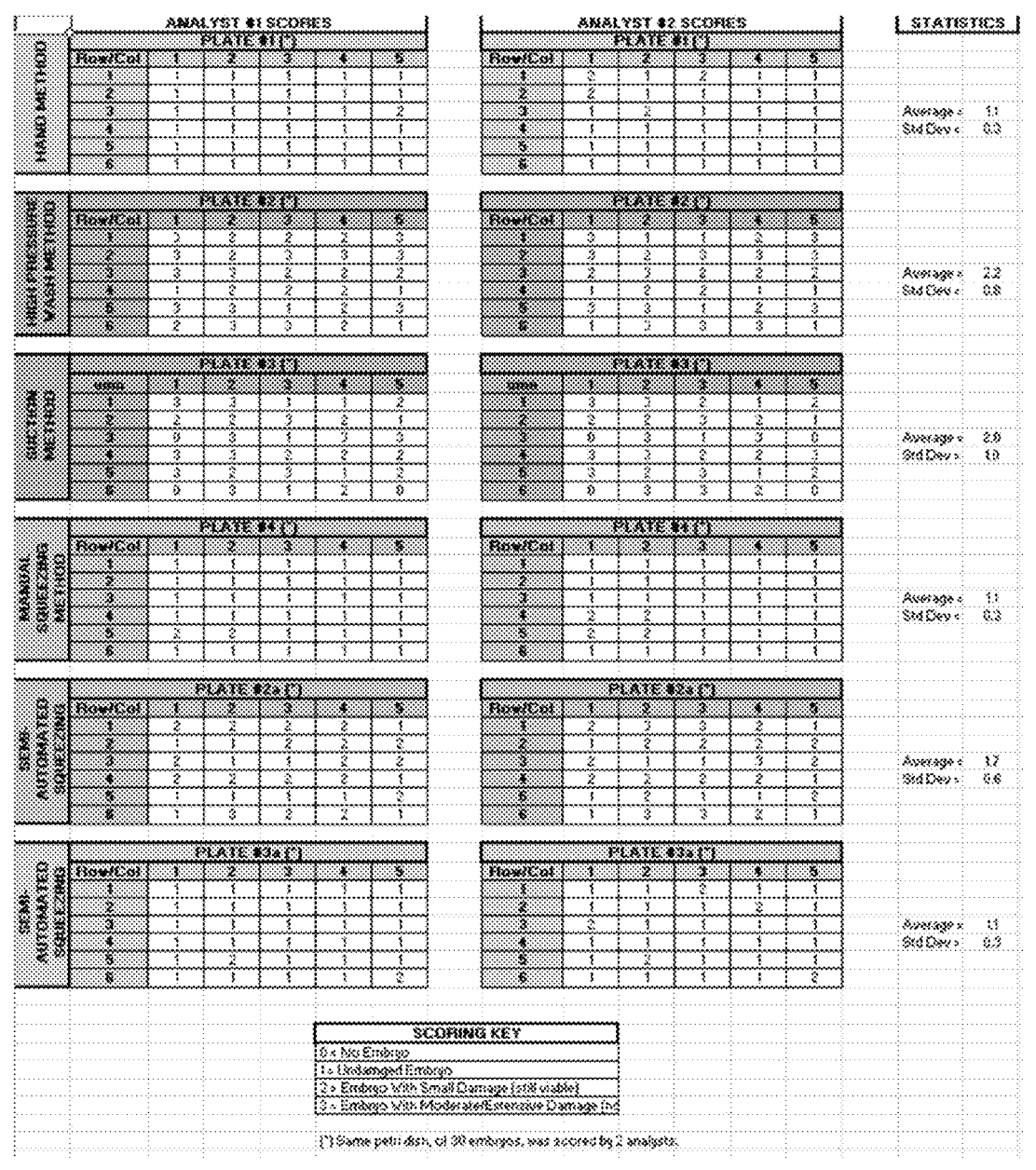

The embryo condition and quality scores are shown in the table provided as FIG. 26. As indicated in the table, the condition and quality of the embryos extracted by manual hand-squeezing and hand methods were very good and substantially the same. The condition and quality of the embryos extracted by the semi-automated extraction method were slightly below that of the embryos extracted by the manual hand-squeezing and hand extraction methods. The condition and quality of the embryos extracted by suction or high-pressure washing methods were poor compared to the hand-squeezing, hand, and semi-automated extraction methods.

Exemplary Methods of Processing Monocot Seeds

In one exemplary aspect, disclosed herein is a method of automatically isolating a monocot embryo from an immature monocot seed having a proximal end and an opposed distal end, wherein, prior to removal of the immature monocot seed from its biological carrier, the proximal end of the immature monocot seed is attached to the biological carrier and the distal end of the immature monocot seed is spaced from the biological carrier, the method comprising: (a) providing an isolated immature monocot seed having an opening or hole in the proximal end of the monocot seed, wherein the isolated immature monocot seed is provided following removal of the immature monocot seed from the biological carrier; and (b) extracting the monocot embryo through the opening or hole in the proximal end of the isolated immature monocot seed, wherein the monocot embryo is undamaged following extraction.

In another exemplary aspect, following extraction of the monocot embryo, the monocot embryo retains an ability to grow with full viability and vigor.

In another exemplary aspect, the step of providing the monocot seed comprises removing at least a portion of the proximal end of the monocot seed without damage to the monocot embryo.

In another exemplary aspect, the immature monocot seed is a corn kernel.

In another exemplary aspect, the immature monocot seed is a sorghum seed, wheat seed or rice seed.

In another exemplary aspect, the immature monocot seed comprises side portions extending between its proximal and distal ends, wherein the step of extracting the monocot embryo through the hole comprises applying pressure to at least one side portion of the monocot seed to force the monocot embryo through the hole in the proximal end of the monocot seed.

In another exemplary aspect, the method further comprises forming the opening or hole in the proximal end of the monocot seed.

In another exemplary aspect, the extracted monocot embryo is released into a liquid bath and generally all other contents of the seed are not released into the liquid bath.

In another exemplary aspect, the method further comprises automatically collecting the extracted monocot embryo. In another exemplary aspect, the method further comprises positioning the extracted monocot embryo within or onto a medium. In one aspect, the medium is a growth medium In another aspect, the medium is a medium containing a selective agent. In another aspect, the medium comprises an antimitotic or chromosome doubling agent.

In another exemplary aspect, the extracted monocot embryo comprises a scutellum section and a meristematic section, wherein the method further comprises removing a sample portion of the scutellum section of the extracted monocot embryo. In another exemplary aspect, the sample portion of the monocot embryo and the remaining viable portion of the monocot embryo are tracked 1 to 1 for future identification and retrieval. In another exemplary aspect, following removal of the sample portion of the scutellum section of the extracted monocot embryo, the monocot embryo retains an ability to grow with full viability and vigor. In another exemplary aspect, the method further comprises using an imaging or measurement system to characterize the extracted monocot embryo to permit identification of the scutellum and meristematic sections of the extracted monocot embryo. In another exemplary aspect, the sample portion of the scutellum section of the extracted monocot embryo is removed by laser. In one aspect, the laser is selected from the group consisting of a cold cutting laser, a Q-switched $CO_2$ laser, a femtosecond laser, a picosecond laser, and a nanosecond laser.

In another exemplary aspect, the method further comprises analyzing the sample portion of the scutellum section of the extracted monocot embryo. In one aspect, the analyzing comprises genetic analysis of the sample. In another exemplary aspect, the method further comprises selecting or discarding remaining portions of the extracted monocot embryo on the basis of the genetic analysis of the sample portion of the scutellum section of the extracted monocot embryo. In another exemplary aspect, the method further comprises germinating the remaining viable portions of the selected monocot embryo. In another exemplary aspect, the selected monocot embryo is used in a monocot breeding program.

In another exemplary aspect, the immature monocot seed is a maize seed obtained at a predetermined time after pollination.

In various exemplary aspects, disclosed herein is a method of regenerating a plant from an immature monocot seed, the method comprising: (a) automatically extracting a monocot embryo from a monocot seed, the extracted monocot embryo comprising a meristematic section and a scutellum section, wherein the extracted monocot embryo is undamaged following extraction, (b) removing a sample portion of the scutellum section of the monocot embryo without damage to the extracted monocot embryo, (c) identifying and associating the sample to viable embryo portion for tracking in a 1 to 1 relationship; (d) genetically analyzing the sample portion of the scutellum section of the monocot embryo, and (e) generating a plantlet from remaining portions of the extracted monocot embryo, wherein the remaining portions of the extracted monocot embryo comprise the meristematic section of the extracted monocot embryo.

In another exemplary aspect, following extraction of the monocot embryo and removal of the sample portion of the scutellum section of the monocot embryo, the monocot embryo retains an ability to grow with full viability and vigor.

In another exemplary aspect, the immature monocot seed has a proximal end and an opposed distal end, wherein, prior to removal of the immature monocot seed from a biological carrier, the proximal end of the immature monocot seed is attached to the biological carrier and the distal end of the immature monocot seed is spaced from the biological carrier, wherein the monocot embryo is extracted from the monocot seed following removal of the monocot seed from the biological carrier, and wherein an opening or hole is formed in the proximal end of the monocot seed without damage to the monocot embryo. In another exemplary aspect, the opening or hole is formed in the proximal end of the monocot seed using a cutting blade, pinching and tearing, poking, scraping, chemically degrading, using a a laser or other cutting elements.

In another exemplary aspect, the sample portion of the scutellum section of the monocot embryo is removed by laser, poking, scraping, or sloughing. In another exemplary aspect, the laser is selected and configured to minimize a heat affected zone of the monocot embryo.

In additional exemplary aspects disclosed herein is a method of extracting a corn embryo, comprising: (a) obtaining an isolated corn kernel removed from a cob; (b) placing the corn kernel in a desired orientation; and (c) removing the tip cap of the corn kernel; (d) applying force to extract the corn embryo from the corn kernel; and (e) collecting the embryo. Optionally, the corn kernel is an immature corn kernel.

In another exemplary aspect, the step of positioning the corn kernel in the desired orientation comprises placing the corn kernel in a liquid bath, wherein upon positioning of the corn kernel in the liquid bath, the corn kernel achieves the desired orientation.

In another exemplary aspect, the immature corn kernel has a proximal end and an opposed distal end, wherein, prior to removal of the immature corn kernel from the cob, the proximal end of the immature corn kernel is attached to the cob and the distal end of the immature corn kernel is spaced from the cob, wherein the immature corn kernel has an opening or hole in the proximal end before it is placed in the liquid bath in step (b), or an opening or hole in the proximal end is formed after the step of placing the corn kernel in the liquid bath in step (b).

In another exemplary aspect, following extraction of the corn embryo, the corn embryo retains an ability to grow with full viability and vigor.

In another exemplary aspect, the method further comprises genotyping the corn embryo. In another aspect, the method further comprises selecting or discarding the corn embryo on the basis of the genotyping. In another aspect, the method further comprises germinating remaining portions of the selected corn embryo.

In another exemplary aspect, a portion of a scutellum section of the corn embryo is cut to extract a sample portion of the scutellum section. In another exemplary aspect, the scutellum section is cut by laser. In another exemplary aspect, the sample portion of the scutellum section is genetically analyzed. In another exemplary aspect, the method further comprises selecting or discarding the corn embryo on the basis of an analysis of the sample portion of the scutellum section. In another exemplary aspect, the method further comprises germinating remaining portions of the selected monocot embryo.

In another exemplary aspect, the liquid bath is filled with at least one of water, sterile solution, buffer, or liquid gel.

In another exemplary aspect, the immature corn kernel is obtained at a predetermined time after pollination.

In another exemplary aspect, the step of obtaining an isolated immature corn kernel comprises: positioning an ear of immature corn within a receiving space defined between opposed engagement elements of at least one clamp assembly, the ear being removed from a stalk and having a proximal end, a distal end, a cob having a pith, and at least one immature corn kernel attached to the cob, wherein, prior to removal of the ear from the stalk, the proximal end of the ear is attached to the stalk; selectively adjusting a position of the opposed engagements elements relative to a translation axis to securely engage the ear in an orientation that is substantially perpendicular to the translation axis; and inserting a threaded portion of a spindle through at least a portion of the pith of the cob of the ear, the spindle extending substantially perpendicularly to the translation axis, the spindle having a base portion that abuts a proximal end of the ear.

In another exemplary aspect, the step of inserting the threaded portion of the spindle through at least a portion of the pith comprises operatively coupling the base portion of the spindle to at least one spindle actuator and selectively activating the at least one spindle actuator to rotate and axially advance the threaded portion of the spindle through at least a portion of the pith.

In another exemplary aspect, the step of obtaining an isolated immature corn kernel further comprises: selectively adjusting the position of the opposed engagements elements relative to the translation axis to disengage the ear; operatively coupling the base portion of the spindle to at least one actuator; and selectively activating the at least one actuator to effect axial and rotational movement of the spindle and the ear relative to an orientation axis, wherein the at least one actuator is selectively activated to advance the spindle and the ear through a cutting assembly.

In another exemplary aspect, the cutting assembly removes immature corn kernel from the cob of the ear, and wherein the method further comprises collecting immature corn kernel that has been removed from the cob.

In another exemplary aspect, the step of obtaining an isolated immature corn kernel comprises: inserting a spindle through the cob of an ear of corn, wherein a base portion of the spindle abuts a proximal end of the ear and a threaded portion of the spindle extends through the cob of the ear of corn, and wherein a distal end of the threaded portion of the spindle projects from a distal end of the ear; axially advancing and rotating the spindle and the ear of corn relative to an orientation axis, wherein the ear of corn is axially advanced through a cutting assembly having at least one cutting arm; and pivoting at least one cutting arm of the cutting assembly to move a cutting portion of the at least one cutting arm relative to a desired arcuate profile that intersects the orientation axis, wherein during pivotal movement of the at least one cutting arm, the cutting portion of the at least one cutting arm removes intact immature corn kernels from the cob of the ear.

In another exemplary aspect, each cutting arm of the at least one cutting arm has a grinding portion that is angularly oriented relative to the cutting portion, and wherein the grinding portion removes softer outer structures of the ear as the cutting arm moves radially inwardly toward the orientation axis.

In another exemplary aspect, the step of pivoting the at least one cutting arm comprises selectively applying pressure to the at least one cutting arm using at least one air cylinder, and wherein the at least one air cylinder effects movement of the cutting portion of each respective cutting arm toward the orientation axis.

In another exemplary aspect, the method further comprises securely engaging the distal end of the spindle with a support element to stabilize the ear during operation of the at least one cutting arm, wherein the at least one cutting arm is positioned between at least one spindle actuator and the support element relative to the orientation axis.

In another exemplary aspect, the step of obtaining an isolated immature corn kernel comprises: inserting a spindle through the cob of an ear of corn, wherein a base portion of the spindle abuts a proximal end of the ear and a threaded portion of the spindle extends through the cob of the ear of corn, and wherein a distal end of the threaded portion of the spindle projects from a distal end of the ear; and axially advancing and rotating the spindle and the ear of corn relative to an orientation axis, wherein the ear of corn is axially advanced through a cutting assembly having a cutting head, the cutting head having a body portion, a support arm that is pivotally coupled to the body portion and biased radially inwardly toward the orientation axis, and a cutting member that is secured to the body portion and radially biased toward the orientation axis, wherein the body portion and the support arm cooperate to engage the ear of corn, and wherein the cutting member of the cutting head removes intact immature corn kernels from the cob of the ear positioned on the spindle as the ear is advanced relative to the orientation axis.

In another exemplary aspect, the method further comprises pivotally coupling the cutting head to a frame to permit pivotal movement of the cutting head about the orientation axis.

In another exemplary aspect, the method further comprises selectively adjusting a position of the cutting head relative to a vertical axis that is substantially perpendicular to the orientation axis.

In another exemplary aspect, the method further comprises selectively adjusting a position of the cutting member relative to a vertical axis that is substantially perpendicular to the orientation axis.

In another exemplary aspect, the method further comprises selectively applying pressure to the cutting member using at least one air cylinder, wherein the at least one air cylinder effects radial movement of the cutting member toward the orientation axis.

In another exemplary aspect, the method further comprises securely engaging the distal end of the spindle with a support element to stabilize the ear during operation of the cutting head, wherein the cutting head is positioned between at least one spindle actuator and the support element relative to the orientation axis.

In another exemplary aspect, the cutting member of the cutting head has a cutting element and a grinding element, wherein the grinding element is angularly oriented relative to the cutting element, and wherein the grinding element removes softer outer structures of the ear as the cutting member moves radially inwardly toward the orientation axis.

In another exemplary aspect, the step of obtaining an isolated immature corn kernel comprises: inserting a distal end of an ear of corn through an opening defined by a feed block assembly, the feed block assembly being axially spaced from a base portion relative to a vertical axis, wherein at least one feed wheel is positioned on a first side of the opening of the feed block assembly and at least one feed wheel are positioned on a second side of the opening of the feed block assembly, wherein the feed wheels positioned on the first side of the opening are spaced apart from the feed wheels positioned on the second side of the opening relative to a first axis that is substantially perpendicular to the vertical axis; selectively rotating a plurality of shafts, each shaft having a proximal portion positioned within a corresponding bore defined by a base element and a distal portion operatively coupled to at least one feed wheel of the plurality of feed wheels, wherein rotation of the plurality of shafts effects a corresponding rotation of the plurality of feed wheels; and effecting oscillating movement of a cutting arm relative to the vertical axis, the cutting arm having a proximal portion and a distal portion, the distal portion defining a cutting element and a grinding element, wherein the cutting arm extends substantially parallel to the second axis, and wherein the distal portion of the cutting arm is positioned over the opening of the feed block assembly relative to the vertical axis, wherein the cutting element of the cutting assembly removes intact immature corn kernels from the cob of the ear as the ear is advanced into the opening of the feed block assembly relative to the vertical axis.

In another exemplary aspect, the feed block assembly comprises a fixed portion and a moveable portion that cooperate to define the opening of the feed block assembly, wherein the at least one feed wheel positioned on the first side of the opening is coupled to the fixed portion, wherein the at least one feed wheel positioned on the second side of the opening is coupled to the moveable portion, and wherein the method further comprises selectively axially moving the moveable portion of the feed block assembly relative to the first axis to selectively adjust a diameter of the opening of the feed block assembly.

In another exemplary aspect, the step of obtaining an isolated immature corn kernel comprises removing chaff from at least one immature corn kernel, the removal of the chaff from the at least one immature corn kernel comprising: positioning at least one immature corn kernel within an inlet portion of a receiving channel defined by a plate assembly having at least one guide plate and a perforated plate, the perforated plate having a first surface and an opposed second surface and defining a plurality of bores that extend from the first surface to the second surface relative to a first axis, the at least one guide plate and the first surface of a perforated plate cooperating to define the receiving channel, the receiving channel extending parallel to a second axis, the second axis being substantially perpendicular to the first axis, the first surface of the perforated plate having a desired surface roughness; effecting selective oscillating movement of the perforated plate relative to a third axis that is substantially perpendicular to both the first and second axes; and selectively activating a pulley assembly to engage and effect movement of the at least one immature corn kernel relative to the second axis from the inlet portion of the receiving channel of the plate assembly to the outlet portion of the receiving channel of the plate assembly, wherein the at least one guide plate of the plate assembly restricts movement of the at least one immature corn kernel relative to the third axis, and wherein, during oscillating movement of the perforated plate, the perforated plate pulls chaff away from the at least one immature corn kernel as the corn kernel moves relative to the second axis within the receiving channel of the plate assembly.

In another exemplary aspect, the step of effecting selective oscillating movement of the perforated plate relative to the third axis comprises effecting selective oscillating movement of the perforated plate relative to a third axis at a selected oscillation rate, and wherein the selected oscillation rate ranges from about 20 strokes per minute to about 150 strokes per minute.

In another exemplary aspect, each stroke corresponds to a selected stroke distance relative to the third axis, and wherein the selected stroke distance ranges from about 1 inch to about 3 inches.

In another exemplary aspect, the pulley assembly effects movement of the at least one immature corn kernel relative to the second axis at a belt speed ranging from about 50 inches per minute to about 200 inches per minute.

In another exemplary aspect, the step of obtaining an isolated immature corn kernel comprises: positioning a plurality of immature corn kernels within a hopper having a longitudinal axis, the hopper defining an outlet; effecting vibration of the hopper; and sequentially receiving the plurality of immature corn kernels from the outlet of the hopper within a channel of a trough, the channel of the trough extending substantially parallel to a longitudinal axis of the trough.

In another exemplary aspect, the method further comprises: using a sensor to produce an output indicative of the presence or absence of an immature corn kernel within the trough using a sensor; and communicating the output to a first actuator, the first actuator configured to effect vibration of the hopper, wherein, in response to receiving an output indicative of the presence of an immature corn kernel within the trough, the first actuator ceases vibration of the hopper.

In another exemplary aspect, the method further comprises effecting vibration of the trough.

In another exemplary aspect, the step of placing the immature corn kernel in a liquid bath comprises: positioning the immature corn kernel within a receptacle defined about a circumference of a wheel, the wheel being configured for rotation about a rotational axis, wherein the immature corn kernel is positioned within the receptacle when the receptacle is at a first rotational position relative to the rotational axis; and rotating the wheel about the rotational axis to position the receptacle at a second rotational position, wherein, in the second rotational position, the corn kernel exits the receptacle into the liquid bath, and wherein, during rotation of the receptacle from the first rotational postion to the second rotational position, the receptacle enters the liquid bath.

In another exemplary aspect, the method further comprises: receiving the corn kernel within a receptacle defined by a feed chain positioned within the liquid bath; and effecting axial movement of the feed chain relative to a longitudinal axis that is substantially perpendicular to the rotational axis of the wheel to transport the corn kernel relative to the longitudinal axis.

In another exemplary aspect, the belt assembly comprises first and second side transport belts that are spaced apart relative to a transverse axis that is substantially perpendicular to the longitudinal axis and a vertical axis, wherein the first and second transport belts define a transport channel that extends substantially parallel to the longitudinal axis, wherein the transport channel is positioned in communication with the feed chain, and wherein the method further comprises: delivering an immature corn kernel from a receptacle of the feed chain to the transport channel; and driving movement of the immature corn kernel relative to the longitudinal axis using the side transport belts.

In another exemplary aspect, the method further comprises using a lifter belt positioned below the transport channel to engage the immature corn kernel within the transport channel and drive upward movement of the corn kernel relative to a vertical axis until the corn kernel contacts a lower surface of a ceiling belt positioned above the transport channel relative to the vertical axis, wherein the ceiling belt has a lower surface that has a consistent height relative to the vertical axis.

In another exemplary aspect, the step of removing at least a portion of the proximal end of the immature corn kernel to form an opening in the corn kernel comprises: positioning an individual corn kernel within a receiving channel defined by a kernel stabilizing portion, wherein the kernel stabilizing portion supports the corn kernel in a desired position as the corn kernel is advanced relative to a longitudinal axis, wherein in the desired position, at least a portion of the proximal end of the corn kernel extends upwardly from the kernel stabilizing portion relative to a vertical axis that is substantially perpendicular to the longitudinal axis; and rotating at least one wheel to apply a force to the proximal end of the corn kernel as the corn kernel is advanced through the receiving channel of the kernel stabilizing portion relative to the longitudinal axis.

In another exemplary aspect, the force applied to the proximal end of the corn kernel can be at least one of a ripping force, a tearing force, a squeezing force, a pinching force, a crushing force, or a cutting force.

In another exemplary aspect, the step of rotating at least one wheel to apply a force to the proximal end of the corn comprises counter-rotating opposed first and second wheels to apply a pinching force to the proximal end of the corn kernel to remove at least a portion of the proximal end of the immature corn kernel.

In another exemplary aspect, the step of applying force to extract the corn embryo through the opening of the corn kernel comprises: delivering the immature corn kernel from the kernel stabilizing portion to a channel defined by opposed squeeze bars as the corn kernel is advanced relative to the longitudinal axis, the first and second opposed squeeze bars being spaced apart relative to a transverse axis that is substantially perpendicular to the vertical axis and the longitudinal axis, wherein at least one of the opposed squeeze bars is biased inwardly toward the other squeeze bar; and using the opposed squeeze bars to apply a radial squeezing force to the immature corn kernel as it moves through the channel of the squeezing portion relative to the longitudinal axis.

In another exemplary aspect, the step of collecting the corn embryo comprises: positioning an embryo collection tube in fluid communication with the liquid bath; and following extraction of an embryo from an immature corn kernel in response to application of the radial squeezing force by the opposed squeeze bars, using water flow to transport the embryo through the embryo collection tube.

In further exemplary aspects, disclosed herein is a method of regenerating a plant from an immature monocot seed, the method comprising: (a) automatically extracting a monocot embryo from each respective monocot seed of a plurality of monocot seeds, each extracted monocot embryo comprising a meristematic section and a scutellum section, wherein the extracted monocot embryo of each respective monocot seed is undamaged following extraction, (b) removing a sample portion of the scutellum section of the monocot embryo of each respective monocot seed without damage to the monocot embryo and identifying and associating the embryo and the sample for tracking the sample portion and the monocot embryo in 1 to 1 relationship, (c) genetically analyzing the sample portion of the scutellum section of the monocot embryo of each respective monocot seed, and (d) selecting or discarding remaining portions of the monocot embryo of each respective monocot seed on the basis of the genetic analysis of the sample portion of the scutellum section of the monocot embryo of each respective monocot seed, wherein the remaining portions of the monocot embryo of at least one monocot seed of the plurality of monocot seeds is selected; and (e) regenerating a plant from the remaining portions of the monocot embryo of each respective selected monocot seed.

In another exemplary aspect, following extraction of the monocot embryo of each respective monocot seed and removal of the sample portion of the scutellum section of the monocot embryo of each respective monocot seed, the monocot embryo of each respective monocot seed retains an ability to grow with full viability and vigor.

In another exemplary aspect, each respective monocot seed has a proximal end and an opposed distal end, wherein, prior to removal of each immature monocot seed. from a biological carrier, the proximal end of the immature monocot seed is attached to the carrier and the distal end of the immature monocot seed is spaced from the carrier, wherein the monocot embryo of each respective immature monocot seed is extracted from the monocot seed following removal of the monocot seed from the carrier, and wherein an opening or hole is formed in the proximal end of each respective monocot seed without damage to the monocot embryo of the monocot seed.

In another exemplary aspect, the method does not comprise sieving material extracted from each monocot seed to separate the monocot embryo of each respective monocot seed from other extracted material.

In another exemplary aspect, the method further comprises: assigning the extracted monocot embryo of each respective monocot seed at least one identifier, each identifier being indicative of at least one of a variety of the monocot seed from which the monocot embryo was obtained; (ii) associating at least one identifier to each respective extracted monocot embryo; and (iii) tracking a location of at least one extracted monocot embryo using the at least one identifier associated with the at least one extracted monocot embryo.

In another exemplary aspect, at least one of the steps of (b) removing a sample portion of the scutellum section of the monocot embryo of each respective monocot seed, (c) genetically analyzing the sample portion of the scutellum section of the monocot embryo of each respective monocot seed, (d) selecting or discarding remaining portions of the monocot embryo of each respective monocot seed on the basis of the genetic analysis of the sample portion of the scutellum section of the monocot embryo of each respective monocot seed, and (e) regenerating a plant from the remaining portions of the monocot embryo of each respective selected monocot seed is performed automatically.

Exemplary Seed Processing Systems

In exemplary aspects, disclosed herein is a system for removing chaff from immature corn kernel, comprising: a plate assembly having at least one guide plate and a perforated plate, the perforated plate having a first surface and an opposed second surface and defining a plurality of bores that extend from the first surface to the second surface relative to a first axis, the at least one guide plate and the first surface of the perforated plate cooperating to define a receiving channel, the receiving channel extending parallel to a second axis and having an inlet portion and an outlet portion, the second axis being substantially perpendicular to the first axis, the inlet portion of the receiving channel being configured to receive at least one immature corn kernel, the perforated plate being configured fir selective oscillating movement relative to a third axis that is substantially perpendicular to both the first and second axes, the first surface of the perforated plate having a desired surface roughness; and a pulley assembly configured to effect movement of the at least one kernel relative to the second axis from the inlet portion of the receiving channel of the plate assembly to the outlet portion of the receiving channel of the plate assembly, wherein the at least one guide plate of the plate assembly is configured to restrict movement of the at least one corn kernel relative to the third axis, and wherein, during oscillating movement of the perforated plate, the perforated plate is configured to pull chaff away from the at least one corn kernel as the corn kernel moves relative to the second axis within the receiving channel of the plate assembly.

In another exemplary aspect, the pulley assembly comprises a belt pulley and a belt roll that is operatively coupled to the belt pulley, wherein the belt roll is configured for engagement with the at least one corn kernel within the receiving channel of the plate assembly. In another exemplary aspect, the belt roll comprises foam.

In further exemplary aspects, disclosed herein is a system for extracting an embryo from an immature corn kernel, the system having a longitudinal axis and comprising: a liquid bath; a belt assembly positioned within the liquid bath and configured to sequentially advance a plurality of corn kernels relative to the longitudinal axis of the system; a force application assembly comprising: a kernel stabilizing portion defining a receiving channel that is configured to receive and support an individual corn kernel in a desired position as the corn kernel is advanced relative to the longitudinal axis of the system, wherein in the desired position, at least a portion of a proximal end of the corn kernel extends upwardly from the kernel stabilizing portion relative to a vertical axis that is substantially perpendicular to the longitudinal axis of the system; at least one wheel operatively positioned relative to the kernel stabilizing portion, wherein the at least one wheel is selectively rotatable to apply a force to the proximal end of the corn kernel as the corn kernel is advanced through the receiving channel of the kernel stabilizing portion relative to the longitudinal axis of the system; a squeezing portion having first and second opposed squeeze bars that are spaced apart relative to a transverse axis that is substantially perpendicular to the vertical axis and the longitudinal axis of the system, wherein the opposed squeeze bars cooperate to define a channel, the channel being configured to receive an immature corn kernel from the kernel stabilizing portion as the corn kernel is advanced relative to the longitudinal axis of the system, wherein at least one of the opposed squeeze bars is biased toward the other squeeze bar relative to the transverse axis, and wherein the opposed squeeze bars are configured to apply a radial squeezing force to the immature corn kernel as it moves through the channel of the squeezing portion relative to the longitudinal axis; and an embryo collection tube positioned in fluid communication with the liquid bath and configured to receive liquid containing an embryo extracted from an immature corn kernel in response to application of the radial squeezing force by the squeezing portion of the system.

In another exemplary aspect, the first squeeze bar of the squeezing portion is biased inwardly toward the second squeeze bar, and the second squeeze bar has a fixed position.

In another exemplary aspect, the first squeeze bar has a convex profile relative to the longitudinal axis of the system, and the second squeeze bar has a concave profile relative to the longitudinal axis of the system.

In another exemplary aspect, the at least one wheel of the force application assembly comprises first and second wheels positioned on opposing sides of the receiving channel of the kernel stabilizing portion.

In another exemplary aspect, the at least one wheel of the force application assembly comprises a single wheel.

In another exemplary aspect, the system further comprises: a singulation assembly configured to receive a plurality of immature corn kernels and separate a single immature corn kernel from the remaining immature corn kernels of the plurality of immature corn kernels; and an indexing assembly at least partially positioned within the liquid bath and configured to receive a single immature corn kernel from the singulation assembly and to transport the single immature corn kernel to the belt assembly in a desired orientation, wherein the singulation assembly has an outlet, wherein the indexing assembly has an inlet, and wherein the outlet of the singulation assembly is positioned in communication with the inlet of the indexing assembly.

In another exemplary aspect, the singulation assembly comprises: a hopper configured to receive a plurality of immature monocot kernels, the hopper having a longitudinal axis and defining a outlet; a trough having a longitudinal axis and being configured to sequentially receive the plurality of immature monocot kernels from the outlet of the hopper, the longitudinal axis of the trough being substantially parallel to the longitudinal axis of the system, the trough defining a channel that extends substantially parallel to the longitudinal axis of the trough, wherein the channel defines the outlet of the singulation assembly; and a first actuator operatively coupled to the hopper, wherein the first actuator is configured to effect vibration of the hopper.

In another exemplary aspect, the system further comprises a sensor configured to produce an output indicative of the presence or absence of an immature monocot kernel within the trough, wherein the sensor is positioned in operative communication with the first actuator and configured to communicate the output to the first actuator, and wherein, in response to receiving an output indicative of the presence of an immature monocot kernel within the trough, the first actuator is configured to cease vibration of the hopper.

In another exemplary aspect, the indexing assembly comprises: a wheel having a circumference and being configured for rotation about a rotational axis that is substantially parallel to the transverse axis, the wheel defining a plurality of receptacles about its circumference, wherein each respective receptacle is configured to receive a single immature corn kernel when the receptacle is at a first rotational position relative to the rotational axis, and wherein each receptacle is configured to permit the corn kernel to exit the receptacle when the receptacle is positioned in a second rotational position relative to the rotational axis; a wheel actuator operatively coupled to the wheel, wherein the actuator is configured to effect rotation of the wheel about the rotational axis; a feed chain positioned within the liquid bath and defining a plurality of receptacles, wherein the feed chain is configured for axial movement relative to the longitudinal axis of the system, and wherein each receptacle of the feed chain is configured to receive a single immature monocot kernel and transport the monocot kernel relative to the longitudinal axis of the system.

In another exemplary aspect, the system further comprises a sensor configured to produce an output indicative of the presence or absence of an immature monocot kernel within the inlet of the indexing assembly, wherein the sensor is positioned in operative communication with the wheel actuator and configured to communicate the output to the wheel actuator, and wherein, in response to receiving an output indicative of the presence of an immature monocot kernel at the inlet of the indexing assembly, the wheel actuator is configured to effect rotation of the hopper.

In another exemplary aspect, the belt assembly comprises first and second side transport belts that are spaced apart relative to the transverse axis of the system to define a transport channel that extends substantially parallel to the longitudinal axis of the system, wherein the transport channel is positioned in communication with the feed chain and configured to receive an immature corn kernel from a receptacle of the feed chain, wherein the first and second side transport belts are configured to drive movement of the immature corn kernel relative to the longitudinal axis of the system.

In another exemplary aspect, the belt assembly further comprises: a ceiling belt positioned above the transport channel relative to the vertical axis, wherein the ceiling belt has a lower surface that has a consistent height relative to the vertical axis; and a lifter belt positioned below the transport channel and the ceiling belt relative to the vertical axis, wherein the lifter belt has an upper surface that is configured to engage an immature corn kernel within the transport channel and drive upward movement of the immature corn kernel relative to the vertical axis until the immature corn kernel contacts the lower surface of the ceiling belt.

In another exemplary aspect, the system further comprises a chaff removal system defining a receiving channel having an inlet portion and an outlet portion, the inlet portion of the receiving channel being configured to receive at least one immature corn kernel, wherein the chaff removal system is configured to remove chaff from immature corn kernels within the receiving channel and transport the immature corn kernels from the inlet portion of the receiving channel to the outlet portion of the receiving channel. In another exemplary aspect, the chaff removal system comprises: a plate assembly having at least one guide plate and a perforated plate, the perforated plate having a first surface and an opposed second surface and defining a plurality of bores that extend from the first surface to the second surface relative to a first axis, the at least one guide plate and the first surface of the perforated plate cooperating to define the receiving channel, the receiving channel extending parallel to a second axis, the second axis being substantially perpendicular to the first axis, the inlet portion of the receiving channel being configured to receive at least one immature corn kernel, the perforated plate being configured for selective oscillating movement relative to a third axis that is substantially perpendicular to both the first and second axes, the first surface of the perforated plate having a desired surface roughness; and a pulley assembly configured to effect movement of the at least one kernel relative to the second axis from the inlet portion of the receiving channel of the plate assembly to the outlet portion of the receiving channel of the plate assembly, wherein the at least one guide plate of the plate assembly is configured to restrict movement of the at least one corn kernel relative to the third axis, and wherein, during oscillating movement of the perforated plate, the perforated plate is configured to pull chaff away from the at least one corn kernel as the corn kernel moves relative to the second axis within the receiving channel of the plate assembly.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

The invention claimed is:

1. A system for extracting an embryo from an immature corn kernel, the system having a longitudinal axis and comprising:
   a. a liquid bath;
   b. a belt assembly positioned within the liquid bath and configured to sequentially advance a plurality of corn kernels relative to the longitudinal axis of the system;
   c. a force application assembly comprising:
      i. a kernel stabilizing portion defining a receiving channel that is configured to receive and support an individual corn kernel in a desired position as the corn kernel is advanced relative to the longitudinal axis of the system, wherein in the desired position, at least a portion of a proximal end of the corn kernel extends upwardly from the kernel stabilizing portion relative to a vertical axis that is substantially perpendicular to the longitudinal axis of the system;
      ii. at least one wheel operatively positioned relative to the kernel stabilizing portion, wherein the at least one wheel is selectively rotatable to apply a force to the proximal end of the corn kernel as the corn kernel is advanced through the receiving channel of the kernel stabilizing portion relative to the longitudinal axis of the system;
      iii. a squeezing portion having first and second opposed squeeze bars that are spaced apart relative to a transverse axis that is substantially perpendicular to the vertical axis and the longitudinal axis of the system, wherein the opposed squeeze bars cooperate to define a channel, the channel being configured to receive an immature corn kernel from the kernel stabilizing portion as the corn kernel is advanced relative to the longitudinal axis of the system, wherein at least one of the opposed squeeze bars is biased toward the other squeeze bar relative to the transverse axis, and wherein the opposed squeeze bars are configured to apply a radial squeezing force to the immature corn kernel as it moves through the channel of the squeezing portion relative to the longitudinal axis; and
   d. an embryo collection tube positioned in fluid communication with the liquid bath and configured to receive liquid containing an embryo extracted from an immature corn kernel in response to application of the radial squeezing force by the squeezing portion of the system wherein the system is configured to perform a process comprising:
   obtaining an intact immature corn kernel by mechanically cutting from a cob and removing any attached chaff or beeswings from the kernel; placing the intact immature corn kernel in a liquid bath to achieve a natural orientation, in which the portion formerly attached to the cob is oriented upward; transporting the corn kernel with a transport assembly which is positioned to receive and horizontally transport the oriented immature corn kernel through the remainder of the process; positioning the kernel with a lifer assembly which is configured to vertically position the oriented immature corn kernel such that the uppermost point of the oriented immature kernel is located at the consistent height relative to the vertical axis; using a tip remover which is configured to remove about 0.1 to about 3 mm of corn material from the uppermost end to the oriented immature corn kernel to form an opening in the corn kernel and to maintain and intact and undamaged immature corn embryo within; applying opposing forces to the oriented immature corn kernel perpendicular to the vertical axis of the corn kernel, wherein the intact and undamaged immature corn embryo is extracted through the opening of the immature corn kernel; and collecting the isolated, intact and undamaged immature corn embryo into a specified container for use in plant breeding.

2. The system of claim 1, wherein the first squeeze bar of the squeezing portion is biased inwardly toward the second squeeze bar, and wherein the second squeeze bar has a fixed position.

3. The system of claim 2, wherein the first squeeze bar has a convex profile relative to the longitudinal axis of the system, and wherein the second squeeze bar has a concave profile relative to the longitudinal axis of the system.

4. The system of claim 1, wherein the at least one wheel of the force application assembly comprises first and second wheels positioned on opposing sides of the receiving channel of the kernel stabilizing portion.

5. The system of claim 1, further comprising:
 a. a singulation assembly configured to receive a plurality of immature corn kernels and separate a single immature corn kernel from the remaining immature corn kernels of the plurality of immature corn kernels; and
 b. an indexing assembly at least partially positioned within the liquid bath and configured to receive a single immature corn kernel from the singulation assembly and to transport the single immature corn kernel to the belt assembly in a desired orientation,
 wherein the singulation assembly has an outlet, wherein the indexing assembly has an inlet, and wherein the outlet of the singulation assembly is positioned in communication with the inlet of the indexing assembly.

6. The system of claim 5, wherein the singulation assembly comprises:
 a. a hopper configured to receive a plurality of immature corn kernels, the hopper having a longitudinal axis and defining a outlet;
 b. a trough having a longitudinal axis and being configured to sequentially receive the plurality of immature corn kernels from the outlet of the hopper, the longitudinal axis of the trough being substantially parallel to the longitudinal axis of the system, the trough defining a channel that extends substantially parallel to the longitudinal axis of the trough, wherein the channel defines the outlet of the singulation assembly; and
 c. a first actuator operatively coupled to the hopper, wherein the first actuator is configured to effect vibration of the hopper.

7. The system of claim 6, further comprising a sensor configured to produce an output indicative of the presence or absence of an immature corn kernel within the trough, wherein the sensor is positioned in operative communication with the first actuator and configured to communicate the output to the first actuator, and wherein, in response to receiving an output indicative of the presence of an immature corn kernel within the trough, the first actuator is configured to cease vibration of the hopper.

8. The system of claim 5, wherein the indexing assembly comprises:
 a. a wheel having a circumference and being configured for rotation about a rotational axis that is substantially parallel to the transverse axis, the wheel defining a plurality of receptacles about its circumference, wherein each respective receptacle is configured to receive a single immature corn kernel when the receptacle is at a first rotational position relative to the rotational axis, and wherein each receptacle is configured to permit the corn kernel to exit the receptacle when the receptacle is positioned in a second rotational position relative to the rotational axis;
 b. a wheel actuator operatively coupled to the wheel, wherein the actuator is configured to effect rotation of the wheel about the rotational axis;
 c. a feed chain positioned within the liquid bath and defining a plurality of receptacles, wherein the feed chain is configured for axial movement relative to the longitudinal axis of the system, and wherein each receptacle of the feed chain is configured to receive a single immature corn kernel and transport the corn kernel relative to the longitudinal axis of the system.

9. The system of claim 8, further comprising a sensor configured to produce an output indicative of the presence or absence of an immature corn kernel within the inlet of the indexing assembly, wherein the sensor is positioned in operative communication with the wheel actuator and configured to communicate the output to the wheel actuator, and wherein, in response to receiving an output indicative of the presence of an immature corn kernel at the inlet of the indexing assembly, the wheel actuator is configured to effect rotation of the hopper.

10. The system of claim 8, wherein the belt assembly comprises first and second side transport belts that are spaced apart relative to the transverse axis of the system to define a transport channel that extends substantially parallel to the longitudinal axis of the system, wherein the transport channel is positioned in communication with the feed chain and configured to receive an immature corn kernel from a receptacle of the feed chain, wherein the first and second side transport belts are configured to drive movement of the immature corn kernel relative to the longitudinal axis of the system.

11. The system of claim 10, wherein the belt assembly further comprises:
 a. a ceiling belt positioned above the transport channel relative to the vertical axis, wherein the ceiling belt has a lower surface that has a consistent height relative to the vertical axis; and
 b. a lifter belt positioned below the transport channel and the ceiling belt relative to the vertical axis, wherein the lifter belt has an upper surface that is configured to engage an immature corn kernel within the transport channel and drive upward movement of the immature corn kernel relative to the vertical axis until the immature corn kernel contacts the lower surface of the ceiling belt.

12. The system of claim 1, further comprising a chaff removal system defining a receiving channel having an inlet portion and an outlet portion, the inlet portion of the receiving channel being configured to receive at least one immature corn kernel, wherein the chaff removal system is configured to remove chaff from immature corn kernels within the receiving channel and transport the immature corn kernels from the inlet portion of the receiving channel to the outlet portion of the receiving channel.

13. The system of claim 12, wherein the chaff removal system comprises:
   a. a plate assembly having at least one guide plate and a perforated plate, the perforated plate having a first surface and an opposed second surface and defining a plurality of bores that extend from the first surface to the second surface relative to a first axis, the at least one guide plate and the first surface of the perforated plate cooperating to define the receiving channel, the receiving channel extending parallel to a second axis, the second axis being substantially perpendicular to the first axis, the inlet portion of the receiving channel being configured to receive at least one immature corn kernel, the perforated plate being configured for selective oscillating movement relative to a third axis that is substantially perpendicular to both the first and second axes, the first surface of the perforated plate having a desired surface roughness; and
   b. a pulley assembly configured to effect movement of the at least one kernel relative to the second axis from the inlet portion of the receiving channel of the plate assembly to the outlet portion of the receiving channel of the plate assembly,
wherein the at least one guide plate of the plate assembly is configured to restrict movement of the at least one corn kernel relative to the third axis and
wherein, during oscillating movement of the perforated plate, the perforated plate is configured to pull chaff away from the at least one corn kernel as the corn kernel moves relative to the second axis within the receiving channel of the plate assembly.

* * * * *